(12) United States Patent
Blaney

(10) Patent No.: US 8,916,148 B2
(45) Date of Patent: Dec. 23, 2014

(54) TISSUE PLASMINOGEN ACTIVATOR VARIANT USES

(75) Inventor: Martha E. Blaney, El Granada, CA (US)

(73) Assignee: Genentech, Inc., South San Francisco, CA (US)

( * ) Notice: Subject to any disclaimer, the term of this patent is extended or adjusted under 35 U.S.C. 154(b) by 1062 days.

(21) Appl. No.: 12/447,838

(22) PCT Filed: Oct. 30, 2007

(86) PCT No.: PCT/US2007/082933
§ 371 (c)(1),
(2), (4) Date: Oct. 14, 2010

(87) PCT Pub. No.: WO2008/070353
PCT Pub. Date: Jun. 12, 2008

(65) Prior Publication Data
US 2012/0270299 A1  Oct. 25, 2012

Related U.S. Application Data

(60) Provisional application No. 60/864,758, filed on Nov. 7, 2006, provisional application No. 60/983,489, filed on Oct. 29, 2007.

(51) Int. Cl.
*A61K 38/49* (2006.01)
*C12N 9/72* (2006.01)
*A61L 29/16* (2006.01)
*A61M 1/28* (2006.01)
*A61M 25/00* (2006.01)

(52) U.S. Cl.
CPC ........... *A61L 29/16* (2013.01); *A61L 2300/254* (2013.01); *A61K 38/49* (2013.01); *A61M 1/285* (2013.01); *A61M 2025/0019* (2013.01); *C12Y 304/21069* (2013.01); *C12N 9/6459* (2013.01); *A61L 2300/42* (2013.01)
USPC ..................................................... 424/94.64

(58) Field of Classification Search
USPC .................................................... 424/93.64
See application file for complete search history.

(56) References Cited

U.S. PATENT DOCUMENTS

| | | | |
|---|---|---|---|
| 5,019,096 A | 5/1991 | Fox, Jr. et al. | |
| 5,091,442 A | 2/1992 | Milner | |
| 5,362,754 A | 11/1994 | Raad et al. | |
| 5,363,754 A | 11/1994 | Coles | |
| 5,385,732 A | 1/1995 | Anderson et al. | |
| 5,399,158 A | 3/1995 | Lauer et al. | |
| 5,447,724 A | 9/1995 | Helmus et al. | |
| 5,509,896 A | 4/1996 | Carter | |
| 5,556,380 A | 9/1996 | Ridinger et al. | |
| 5,612,029 A | 3/1997 | Bennett et al. | |
| 5,688,516 A | 11/1997 | Raad et al. | |
| 5,772,640 A | 6/1998 | Modak et al. | |
| 5,824,049 A | 10/1998 | Ragheb et al. | |
| 5,837,688 A | 11/1998 | Gelfand | |
| 5,849,736 A | 12/1998 | Wityak et al. | |
| 5,865,178 A | 2/1999 | Yock | |
| 5,932,299 A | 8/1999 | Katoot | |
| 6,087,375 A | 7/2000 | Bridon et al. | |
| 6,124,277 A | 9/2000 | Schacht et al. | |
| 6,166,007 A | 12/2000 | Sodemann | |
| 6,174,537 B1 | 1/2001 | Khan | |
| 6,187,768 B1 | 2/2001 | Welle et al. | |
| 6,206,914 B1 | 3/2001 | Soykan et al. | |
| 6,231,605 B1 | 5/2001 | Ku | |
| 6,258,797 B1 | 7/2001 | Lehner | |
| 6,284,247 B1 | 9/2001 | Goeddel et al. | |
| 6,346,517 B1 | 2/2002 | Wong et al. | |
| 6,350,251 B1 | 2/2002 | Prosl et al. | |
| 7,829,082 B2 | 11/2010 | Semba | |
| 2001/0021811 A1 | 9/2001 | Yock | |
| 2001/0031981 A1 | 10/2001 | Evans et al. | |
| 2002/0051779 A1 | 5/2002 | Gage et al. | |
| 2002/0082582 A1 | 6/2002 | Finch et al. | |
| 2003/0206906 A1* | 11/2003 | Semba | 424/145.1 |
| 2005/0215978 A1 | 9/2005 | Ash | |
| 2006/0246050 A1 | 11/2006 | Semba | |
| 2006/0257390 A1 | 11/2006 | Semba | |
| 2007/0014779 A1 | 1/2007 | Semba | |
| 2010/0330083 A1 | 12/2010 | Semba | |

FOREIGN PATENT DOCUMENTS

| | | |
|---|---|---|
| AU | 42810/89 B | 10/1992 |
| EP | 0 882 461 A2 | 12/1998 |
| EP | 0 882 461 A3 | 12/1998 |
| EP | 1 040 841 A1 | 10/2000 |
| EP | 1 060 747 A2 | 12/2000 |
| EP | 1 442 753 A1 | 8/2004 |

(Continued)

OTHER PUBLICATIONS

Anonymous "TNKase, Tenecteplase Recombinant", Product Brochure by: Genetech, Inc., South San Francisco, CA, May 2000.*
Abbas,Aa.E. et al. (Sep. 6, 2005). "Intracoronary Fibrin-Specific Thrombolytic Infusion Facilities Percutaneous Recanalization of Chronic Total Occlusion," *Journal of the American College of Cardiology* 46(5):793-798.
Allie, D. et al. (Sep. 24, 2002). "Novel Combination Thrombolytic Therapy in Limb Salvage: Mechanical Thrombectomy (Rheolytic Thrombectomy with Angiojet) and Chemical Thrombolysis (Tenecteplase) 'Power-Pulse Spray' Technique," *Am. J. Cardiol.* 90:108H, Poster Abstract No. TCT-270.

(Continued)

*Primary Examiner* — Allison Fox
(74) *Attorney, Agent, or Firm* — Morrison & Foerster LLP

(57) ABSTRACT

A method is disclosed for using tenecteplase to restore function in dysfunctional hemodialysis catheters, which have a blood flow rate of less than 300 mL/minute. Kits are also provided with instructions to direct the user to administer tenecteplase in a total dose of about 3 to 4 mg locally into all catheter lumens and allow the tenecteplase to dwell in the catheter for from about one hour to about 72 hours.

15 Claims, No Drawings

(56) References Cited

FOREIGN PATENT DOCUMENTS

| EP | 1 688 154 A1 | 8/2006 |
|---|---|---|
| JP | 08-503400 T | 4/1996 |
| WO | WO-94/10838 A1 | 5/1994 |
| WO | WO-95/14683 A1 | 6/1995 |
| WO | WO-98/23151 A1 | 6/1998 |
| WO | WO-98/28326 A1 | 7/1998 |
| WO | WO-00/53264 A1 | 9/2000 |
| WO | WO-01/85249 A1 | 11/2001 |
| WO | WO-03/045466 A1 | 6/2003 |
| WO | WO-03/045466 C1 | 6/2003 |
| WO | WO-2006/049813 A2 | 5/2006 |
| WO | WO-2006/049813 A3 | 5/2006 |
| WO | WO-2008/070353 A2 | 6/2008 |
| WO | WO-2008/070353 A3 | 6/2008 |

OTHER PUBLICATIONS

Allie, D.E. et al. (Mar. 2003). "Tenecteplase in Peripheral Thrombolysis: Initial Safety and Feasibility Experience," presented at *Society of Intervention Radiology*, p. S17, Abstract No. 48.

Allwood, M.C. (1999). "Problems With Lines and the Pharmacist's Role," *Nutrition* 15(3):252-253.

Anonymous. (2002). "Cathflo Activase®. Full Prescribing Information," in *2002 Physicians Desk Reference*, Thomas Medical Economics Co.: Montvale, NJ, p. 3611-3612.

Anonymous. (2002). "Retavase®. Full Prescribing Information," in *2002 Physicians Desk Reference*, Thomas Medical Economics Co.: Montvale, NJ, pp. 1182-1184.

Anonymous. (2002). "Streptase®. Full Prescribing Information," in *2002 Physicians Desk Reference*, Thomas Medical Economics Co.: Montvale, NJ, pp. 647-649.

Anonymous. (2002). "TNKase™. Full Prescribing Information," in *2002 Physicians Desk Reference*, Thomas Medical Economics Co.: Montvale, NJ, three pages.

Anonymous. (2005). U.S. Renal Data System, USRDS 2005 Annual Data Report: Atlas of End-Stage Renal Disease in the United States, *National Institutes of Health, National Institute of Diabetes and Digestive and Kidney Diseases*, Bethesda, MD, 6-parts, 282 pages.

Antani, M.R. (Jul. 2001). "Catheter-Directed Thrombolysis for the Treatment of Acute Deep Venous Thrombosis," *Supplement to Applied Radiology* pp. 29-35. (Y Ref.).

Arepally, A. et al. (Jan. 2002). "Weight-Based rt-PA Thrombolysis Protocol for Acute Native Arterial and Bypass Graft Occlusions," *J. Vasc. Interv. Radiol.* 13(1):45-50.

Ashton, J. et al. (Nov. 1990). "Effects of Heparin versus Saline Solution on Intermittent Infusion Device Irrigation," *Heart & Lung: Journal of Critical Care* 19(6):608-612. (Y Ref.).

ASSENT-2 Investigators. (Aug. 28, 1999). "Single-Bolus Tenecteplase Compared with Front-Loaded Alteplase in Acute Myocardial Infarction: The ASSENT-2 Double-Blind Randomised Trial. Assessment of the Safety and Efficacy of a New Thrombolytic Investigators," *Lancet* 354:716-722.

Azmi-Ghadimi, H. et al. (Feb. 2002). "Use of Intraventricular Tissue Plasminogen Activator and Guglielmi Detachable Coiling for the Acute Tratment of Casted Ventricles from Cerebral Aneurysm Hemorrhage: Two Technical Case Reports," *Neurosurgery* 50(2):421-424.

Benedict, C.R. et al. (Nov. 15, 1995). "New Variant of Human Tissue Plasminogen Activator (TPA) with Enhanced Efficacy and Lower Incidence of Bleeding Compared with Recombinant Human TPA," *Circulation* 92(10):3032-3040.

Bookstein, J.J. et al. (Mar. 2000). "Augmented Experimental Pulse-Spray Thrombolysis with Tissue Plasminogen Activator, Enabling Dose Reduction by One or More Orders of Magnitude," *J. Vasc. Interv. Radiol.* 11(3):299-303.

Bookstein, J.J. et al. (Nov.-Dec. 2000). "Plasminogen-Enriched Pulse-Spray Thrombolysis with tPA: Further Developments," *J. Vasc. Interv. Radiol.* 11(10):1353-1362.

Boorgu, R. et al. (Nov. 2000). "Adjunctive Antibiotic/Anticoagulant Lock Therapy in the Treatment of Bacteremia Associated with the Use of a Subcutaneously Implanted Hemodialysis Access Device," *ASAIO J.* 46:767-770.

Buchman, A.L. et al. (Jan. 2001). "Complications of Long-Term Home Total Parenteral Nutrition," *Digestive Diseases and Sciences* 46(1):1-18.

Budavari, S. et al. eds. (1996). *The Merck Index*, Merck & Co., Inc.: Whitehouse Station,. NJ, p. 189.

Burkart, D.J. et al. (Nov. 2002). "Thrombolysis of Occluded Peripheral Arteries and Veins with Tenecteplase: A Pilot Study," *J. Vasc. Interv. Radiol.* 13(11):1099-1102.

Burkart, D.J. et al. (Jun. 2003). "Thrombolysis of Acute Peripheral Arterial and Venous Occlusions with Tenecteplase and Eptifibatide: A Pilot Study," *J. Vasc. Interv. Radiol.* 14(6):729-733.

Buturović, J. et al. (1998). "Filling Hemodialysis Catheters in the Interdialytic Period: Heparin Versus Citrate Versus Polygeline: A Prospective Randomized Study," *Artificial Organs* 22(11):945-947.

Cairoli, O.M. (Mar. 2002). "Practical Application: Using Tissue Plasminogen Activator Overnight in Catheter Clearance on Tunnel Catheters Used for Hemodialysis," *Proceedings of the 22$^{nd}$ Annual Conference on Dialysis* 22(Suppl. 1):556.

Calis, K.A. et al. (Oct. 15, 1999). "Bioactivity of Cryopreserved Alteplase Solutions," *Am. J. Health-Syst. Pharm.* 56:2056-2057.

Cannon, C.P. et al. (1997). "TNK—Tissue Plasminogen Activator in Acute Myocardial Infarction," *Circulation* 95:351-356.

Cannon, C.P. et al. (1998). "TNK—Tissue Plasminogen Activator Compared With Front-Loaded Alteplase in Acute Myocardial Infarction Results of the TIMI 10B Trial," *Circulation* 98:2805-2814.

Casteneda, F. et al. (Jun. 2002). "Catheter-Directed Thrombolysis in Deep Venous Thrombosis with Use of Reteplase: Immediate Results and Complications from a Pilot Study," *J. Vasc. Interv. Radiol.* 13(6):577-580.

Chang, R. et al. (Feb. 2001). "Daily Catheter-Directed Single Dosing of t-PA in Treatment of Acute Deep Venous Thrombosis of the Lower Extremity," *J. Vasc. Interv. Radiol.* 12(2):247-252.

Collen, D. et al. (1994). "Comparative Thrombolytic Properties of Tissue-Type Plasminogen Activator and of a Plasminogen Activator Inhibitor-1-Resistant Glycosylation Variant, in a Combined Arterial and Venous Thrombosis Model in the Dog," *Thromb. Haemost.* 72(1):98-104.

Cornelius, R.M. et al. (2000). "Adsorption of Proteins from Infant and Adult Plasma to Biomaterial Surfaces," *J. Biomed. Meter. Res.* 15:622-632.

Daeihagh, P. et al. (Jul. 2000). "Efficacy of Tissue Plasminogen Activator Administration on Patency of Hemodialysis Access Catheters," *American Journal of Kidney Diseases* 36(1):75-79.

Dariouche, R.O. et al. (1997). "Prevention of Catheter-Related Infections: The Skin," *Nutrition (Suppl.)* 13(4):26S-29S.

Davidian, M.M. et al. (Mar. 2000). "Initial Results of Reteplase in the Treatment of Acute Lower Extremity Arterial Occlusions," *J. Vasc. Interv. Radiol.* 11(3):289-294.

Dawson, K.M. et al. (Jun. 10, 1994). "Plasminogen Mutants Activated by Thrombin. Potential Thrombus-Selective Thrombolytic Agents," *J. Biol. Chem.* 269(23):15989-15992.

Decrinis, M. et al. (1993). "A Simplified Procedure for Intra-arterial Thrombolysis with Tissue-Type Plasminogen Activator in Peripheral Arterial Occlusive Disease: Primary and Long-Term Results," *European Heart Journal* 14:297-305.

Dowling, K. et al. (Mar.-Apr. 2004). "The Use of Tissue Plasminogen Activator Infusion to Re-establish Function of Tunneled Hemodialysis Catheters," *Nephrology Nursing Journal* 31(2):199-200.

Drescher, P. et al. (Jan. 2002). "Initial Experience with the Combination of Reteplase and Abciximab for Thrombolytic Therapy in Peripheral Arterial Occlusive Disease: A Pilot Study," *J. Vasc. Interv. Radiol.* 13(1):37-43.

Drugbank Accession No. BTD00019 "Tenecteplase," last updated Feb. 1, 2007, located at <http//redpoll.pharmacy.ualberta.ca/drugbank/cgi-bin/getCard.cgi?CARD=BTD00019.txt>, last visited Feb. 15, 2007, six pages.

(56) References Cited

OTHER PUBLICATIONS

El-Kassimi, F.A. et al. (Oct. 1986). "Adult Respiratory Distress Syndrome and Disseminated Intravascular Coagulation Complicating Heat Stroke," *Chest* 90(4):571-574.

Elsharawy, M. et al. (Sep. 2002). "Early Results of Thrombolysis vs Anticoagulation in Iliofemoral Venous Thrombosis. A Randomized Clinical Trial," *Eur. J. Vasc. Endovasc. Surg.* 24:209-214.

Eyrich, H. et al. (Aug. 1, 2002). "Alteplase Versus Urokinase in Restoring Blood Flow in Hemodialysis-Catheter Thrombosis," *Am. J. Health-Syst. Pharm.* 59:1437-1440.

Falk, A. et al. (Jun. 30, 2005). "Tenecteplase in the Treatment of Thrombosed Hemodialysis Grafts," *Cardiovascular and Interventional Radiology* 28(4):472-475.

Final Office Action mailed Mar. 31, 2006, for U.S. Appl. No. 10/304,666, filed Nov. 25, 2002, seven pages.

Findlay, J.M. et al. (May 1991). "Lysis of Intraventricular Hematoma with Tissue Plasminogen Activator," *J. Neurosurg.* 74:803-807.

Food and Drug Administration. (Apr. 14, 2000). "FDA Issues Warning on Tricitrasol Dialysis Catheter Anticoagulant," *FDA Talk Paper T00-16*, two pages.

Garrelts, J.C. et al. (Jan. 1989). "Comparison of Heparin and 0.9% Sodium Chloride Injection in the Maintenance of Indwelling Intermittent I.V. Devices," *Clinical Pharmacy* 8:34-39.

Gibson, S.P. et al. (1991). "Five Years Experience with the Quinton Permcath for Vascular Access," *Nephrology Dialysis Transplantation* 6:269-274.

Graul, A. et al. (1997). "Xemilifiban" *Drugs of the Future* 22(5):508-517.

Greco, R.S. et al. (1995). "Patency of a Small Vessel Prosthesis Bonded to Tissue Plasminogen Activator and Iloprost," *Ann. Vac. Surg.* 9(2):140-145.

Habowski, S.R. et al. (2000). "Use of Tissue Plasminogen Activator (t-PA) for Hemodialysis Catheter Malfunction," *J. Am. Soc. Nephrol*, 11:185A, Abstract No. A0988, Poster SA571 (PS).

Haire, W.D. et al. (1994). "Urokinase Versus Recombinant Tissue Plasminogen Activator in Thrombosed Central Venous Catheters: A Double-Blinded, Randomized Trial," *Thromb. Haemost.* 72(4):543-547.

Hammes, M.S. et al. (2001). "Intraluminal Alteplase (t-PA) Is an Effective Means to Treat Occluded Hemodialysis (HD) Catheters," *J. Am. Soc. Nephrol.* 12:290A, Abstract No. A1487, Poster SU1-0723 (PS).

Hara, T. et al. (1994). "DX-9065a; A New Synthetic, Potent Anticoagulant and Selective Inhibitor for Factor Xa," *Thromb. Haemost.* 71(3):314-319.

Hardaway, R.M. et al. (Oct. 2001). "A Shock Toxin That Produces Disseminated Intravascular Coagulation and Multiple Organ Failure," *The American Journal of the Medical Sciences* 322(4):222-228.

Henrickson, K.J. et al. (Mar. 2000). "Prevention of Central Venous Catheter-Related Infections and Thrombotic Events in Immunocompromised Children by the Use of Vancomycin/Ciprofloxacin/Heparin Flush Solution: A Randomized, Multicenter, Double-Blind Trial," *J. Clin. Oncol.* 18(6):1269-1278.

Hofmann, L.V. et al. (2001, e-pub. Nov. 8, 2001). "GPIIb-IIa Receptor Inhibitors: What the Interventional Radiologist Needs to Know," *Cardiovasc. Interv. Radiol.* 24:361-367.

International Search Report mailed Aug. 4, 2003, for PCT/US02/37878, filed Nov. 25, 2002, one page.

International Search Report mailed Jun. 25, 2008, for PCT/US2007/082933, filed Oct. 30, 2007, five pages.

Kaiser, B. (1998). "Thromblin and Factor Xa Inhibitors," *Drugs of the Future* 23(4):423-436.

Kamal, G.D. et al. (May 8, 1991). "Reduced Intravascular Catheter Infection by Antibiotic Bonding: A Prospective, Randomized, Controlled Trial," *J. Amer. Med. Assn.* 265(18):2364-2368.

Karaaslan, H. et al. (2001). "Risk of Heparin Lock-Related Bleeding when using Indwelling Venous Catheter in Haemodialysis," *Nephrol. Dial. Transplant* 16:2072-2074.

Karabit, M.S. et al. (Aug. 1986). Studies on the Evaluation of Preservative Efficacy—II. The Determination of Antimicrobial Characteristics of Benzylalcohol, *J Clin Hosp Pharm* 11(4):281-289.

Karnes, H.T. et al. (1987). "Benzyl Alcohol Interference from Heparin Lock Flush Solutions in a High Pressure Liquid Chromatographic Procedure for Mezlocillin," *Therapeutic Drug Monitoring*, Raven Press Ltd.: New York, NY vol. 9(4):456-460.

Kawasaki, T. et al. (1998). "Effect of a Synthetic Factor Xa Inhibitor, YM-60828, on Blood Vessel Patency in Combination with a Thrombolytic Agent and on Blood Loss from the Operation Site in a Rat Model of Arterial Thrombosis," *Thromb. Haemost.* 79:859-864.

Keyt, B.A. et al. (Apr. 1994). "A Faster-Acting and More Potent Form of Tissue Plasminogen Activator," *Proc. Natl. Acad. Sci. USA* 91:3670-3674.

Leblang, S.D. et al. (Aug. 1992). "Low-Dose Urokinase Regimen for the Treatment of Lower Extremity Arterial and Graft Occlusions: Experience in 132 Cases," *J. Vasc. Interv. Radiol.* 3(3):475-483.

Little, M.A. et al. (Jan. 2002). "A Longitudinal Study of the Repeated Use of Alteplase as Therapy for Tunneled Hemodialysis Catheter Dysfunction," *American Journal of Kidney Diseases* 39(1):86-91.

Lokich, J.J. et al. (May 1985). "Complications and Management of Implanted Venous Access Catheters," *J. Clin. Oncol.* 3(5):710-717.

McNamara, T.O. et al. (Apr. 1985). "Thrombolysis of Peripheral Arterial and Graft Occlusions: Improved Results Using High-Dose Urokinase," *Am. J. Radiol.* 144:769-775.

McNamara, T.O. et al. (Sep. 22, 1999). "Bleeding Associated with Intrathrombus Infusions of r-tPA for Peripheral Arterial and Venous Occlusions," *Am. J. Cardiol.* 84:37P, Abstract No. TCT-92.

Merriam-Webster (2007). OnLine Definition of "Dwell" located at http://mwl.merriam-webster.com/dictionary/dwell, last visited Aug. 13, 2007, one page.

Merriam-Webster (2009). OnLine Definition of "Expose" located at <http://mwl.merriam-webster.com/dictionary/expose>, last visited Dec. 7, 2009, one page.

Mewissen, M.W. et al. (Apr. 1999). "Catheter-Directed Thrombolysis for Lower Extremity Deep Venous Thrombosis: Report of a National Multicenter Registry," *Radiology* 211(1):39-49.

Meyer, B.K. et al. (Dec. 2007). "Antimicrobial Preservative Use in Parenteral Products: Past and Present," *J. Pharm. Sci.* 96(12):3153-3167.

Modi, N.B. et al. (May 2000). "Pharmacokinetics and Pharmacodynamics of Tenecteplase: Result From a Phase II Study in Patients with Acute Myocardial Infarction," *J Clin Pharmacol.* 40(5):508-515.

Moss, A.H. et al. (Dec. 1988). "Use of a Silicone Catheter With a Dacron Cuff for Dialysis Short-Term Vascular Access," *American Journal of Kidney Diseases* XII(6):492-498.

National Kidney Foundation. (2001). "K/DOQI Clinical Practice Guidelines for Vascular Access, 2000," *Am. J. Kidney Dis.* 37(Suppl. 1):S137-S181.

Nehme, T.N. et al. (2002). "Tenecteplase for the Lyse and Wait Technique in Recnalization of Thrombosed PTFE Hemodialysis Grafts," Poster No. 320, *J. Vasc. Interv. Radiol.* 13:S109.

Non-Final Office Action mailed Aug. 24, 2005, for U.S. Appl. No. 10/304,666, filed Nov. 25, 2002, nine pages.

Non-Final Office Action mailed Nov. 6, 2008, for U.S. Appl. No. 11/426,263, filed Jun. 23, 2006, six pages.

Non-Final Office Action mailed Feb. 11, 2009, for U.S. Appl. No. 11/426,283, filed Jun. 23, 2006, seven pages.

Notice of Allowance mailed Jun. 11, 2009, for U.S. Appl. No. 11/426,263, filed Jun. 23, 2006, nine pages.

Notice of Allowance mailed Dec. 15, 2009, for U.S. Appl. No. 11/426,263, filed Jun. 23, 2006, six pages.

Notice of Allowance mailed Jun. 1, 2010, for U.S. Appl. No. 11/426,263, filed Jun. 23, 2006, seven pages.

O'Mara, N.B. et al. (2000). "tPA for Central Vein Dialysis Catheter Patency," *J. Am. Soc. Nephrol.* 11:292A, Abstract No. A1530.

Ouriel, K. et al. (Nov. 1995). "Comparison of Streptokinase, Urokinase, and Recombinant Tissue Plasminogen Activator in an in vitro Model of Venous Thrombolysis," *Journal of Vascular Surgery* 22(5):593-597.

(56) References Cited

OTHER PUBLICATIONS

Ouriel, K. et al. (Apr. 16, 1998). "A Comparison of Recombinant Urokinase with Vascular Surgery as Initial Treatment for Acute Arterial Occlusion of the Legs," *New England J. of Medicine* 338(16):1105-1111.
Ouriel, K. et al. (Mar. 2000). "Complications Associated with the Use of Urokinase and Recombinant Tissue Plasminogen Activator for Catheter-Directed Peripheral Arterial and Venous Thrombolysis," *J. Vasc. Interv. Radiol.* 11(3):295-298.
Ouriel, K. et al. (Jul.-Aug. 2000). "Reteplase in the Treatment of Peripheral Arterial and Venous Occlusions: A Pilot Study," *J. Vasc. Interv. Radiol.* 11(7):849-854.
Patel, N. et al. (May 2001). "SCVIR Reporting Standards for the Treatment of Acute Limb Ischemia with Use of Transluminal Removal of Arterial Thrombus," *J. Vasc. Interv. Radiol.* 12(5):559-570.
Patel, V.B. et al. (1999). "Successful Use of Low Dose r-Hirudin (Refludan®) for Recurrent Dialysis Catheter Thrombosis in a Patient with Heparin Induced Thrombocytopenia," *Thromb. Haemost.* 82:1205-1206.
Ponec, D. et al. (Aug. 2001). "Recombinant Tissue Plasminogen Activator (Alteplase) for Restoration of Flow in Occluded Central Venous Access Devices: A Double-Blind Placebo-Controlled Trial—The Cardiovascular Thrombolytic to Open Occluded Lines (COOL) Efficacy Trial," *J. Vasc. Interv. Radiol.* 12:951-955.
Purchase, L. et al. (1991). "Hemodialysis with a Permcath Kept Open with Streptokinase and Later Citrate in a Heparin-Sensitive Patient," *Nephron* 58:119-120.
Razavi, M.K. et al. (2002). "Initial Clinical Results of Tenecteplase (TNK) in Catheter-Directed Thrombolytic Therapy," *J. Endovasc. Ther.* 9:593-598.
Razavi, M.K. et al. (Feb. 2002). "Initial Clinical Results of Tenecteplase (TNK) in Catheter-Directed Thrombolytic Therapy," presented Apr. 7, 2002, at the 27$^{th}$ Annual Meeting of the Society of Cardiovascular Interventional Radiology, *J. Vasc. Interv. Radiol.* 13(2-part 2):S11, Abstract No. 29.
Refino, C.J. et al. (1993). "A Variant of Tissue Plasminogen Activator (T103N, N117Q, KHRR 296-299 AAAA) With a Decreased Plasma Clearance Rate is Substantially More Potent Than Activase® rt-PA in a Rabbit Thrombolysis Model," *Thromb. Haemost Abstracts Edition* 69(6):841.
Refino, C.J. et al. (1993). "A Variant of t-PA (T103N, KHRRR 296-299 AAAA) that, by Bolus, Has Increased Potency and Decreased Systemic Activation of Plasminogen," *Thromb. Haemost.* 70(2):313-319.
Ricotta, J.J. et al. (Jul. 1987). "Use and Limitations of Thrombolytic Therapy in the Treatment of Peripheral Arterial Ischemia: Results of a Multi-Institutional Questionnaire," *J. Vasc. Surg.* 6(1):45-50.
Roberts, N.E. et al. (2000). "Outpatient Use of Alteplase (t-PA) in De-Clotting Dialysis Catheters," *J. Am. Soc. Neprol.* 11:195A, Abstract No. A1040.
Root, J.L. et al. (Nov. 1988). "Inhibitory Effect of Disodium EDTA Upon the Growth of *Staphylococcus epidermidis* In Vitro: Relation to Infection Prophylaxis of Hickman Catheters," *Antimicrob. Agents Chemother.* 32(11):1627-1631.
Rubin, R.N. (Sep. 1983). "Local Installation of Small Doses of Streptokinase for Treatment of Thrombotic Occlusions of Long-Term Access Catheters," *J. Clin. Oncol.* 1(9):572-573.
Sandbaek, G. et al. (1999). "Soluble, Thrombin-Related Material in Arterial Thrombi and Plasma Studied During Catheter-Directed Intra-Arterial Thrombolysis," *Blood Coagulation and Fibrinolysis* 10(2):87-91.
Scarborough, R.M. et al. (1998). "Eptifibatide," *Drugs of the Future* 23(6):585-590.
Schenk, P. et al. (Jan. 2000). "Recombinant Tissue Plasminogen Activator is a Useful Alternative to Heparin in Priming Quinton Permcath," *Amer. J. Kidney Diseases* 35(1):130-136.

Schwartz, C. et al. (Sep. 1990). "Prevention of Bacteremia Attributed to Luminal Colonization of Tunneled Central Venous Catheters with Vancomycin-Susceptible Organisms," *J. Clin. Oncology* 8(9):1591-1597.
Semba, C.P. et al. (May 1994). "Iliofemoral Deep Venous Thrombosis: Aggressive Therapy with Catheter-Directed Thrombolysis," *Radiology* 191(2):487-494.
Semba, C.P. et al. (Feb. 2000). "Thrombolytic Therapy with Use of Alteplase (rt-PA) in Peripheral Arterial Occlusive Disease: Review of the Clinical Literature," *J. Vasc. Interv. Radiol.* 11(2):149-161.
Semba, C.P. et al. (Mar. 2000). "Alteplase as an Alternative to Urokinase," *J. Vasc. Interv. Radiol.* 11(3):279-287.
Semba, C.P. et al. (Jun. 2001). "Alteplase and Tenecteplase: Applications in the Peripheral Circulation," *Tech. Vasc. Interv. Radiol.* 4(2):99-106.
Semba, C.P. et al. (Feb. 2002). "Alteplase Stability and Bioactivity After Thrombolysis-Facilitated Rheolytic or High-Speed Maceration Thrombectomy," presented Apr. 11, 2002, at the 27$^{th}$ Annual Meeting of the Society of Cardiovascular Interventional Radiology, *J. Vasc. Interv. Radiol.* 13(2-Part 2):S76.
Semba, C.P. et al. (Feb. 2002). "Tenecteplase (TNK): Protein Stability and Bioactivity of Thawed or Diluted Solutions Used in Peripheral Thrombolysis," presented Apr. 11, 2002, at the 27$^{th}$ Annual Meeting of the Society of Cardiovascular Interventional Radiology, *J. Vasc. Interv. Radiol.* 13(2-Part 2):575, Abstract No. 218.
Semba, C.P. et al. (Apr. 2003). "Tenecteplase: Stability and Bioactivity of Thawed or Diluted Solutions Used in Peripheral Thrombolysis," *J. Vasc. Interv. Radiol.* 14(4):475-479.
Shortell, C.K. et al. (Nov. 2001). "Safety and Efficacy of Limited-Dose Tissue Plasminogen Activator in Acute Vascular Occlusion," *J. Vasc. Surg.* 34(5):854-859.
Skrzydlewska, E. et al. (1984-1985). "Effect of Ethanol and Acetaldehyde on Fibrinolytic System in Vitro," *Roczniki Akademii Medyczne w Bialymstoku* 29-30:163-173.
Sodemann, K. et al. (Nov. 2-5, 1997). "Gentamicin/Sodium-Citrate Mixture as Antibiotic-Lock Technique for Salvage and Prevention of Catheter-Related Infections—A Four Year Trial," *30$^{th}$ Annual Meeting of American Society of Nephrology*, San Antonio, TX, (A0811, 5064(PS)) pp. 173A.
Sodemann, K. et al. (2001). "Two Years' Experience with Dialock® and CLS™ (A New Antimicrobial Lock Solution)," *Blood Purif.* 19:251-254.
Spry, L.A. et al. (Jan. 2001). "Low-Dose tPA for Hemodialysis Catheter Clearance," *Dialysis and Transplantation* 30(1):10-13.
Stas, K.J.F. et al. (2001). "Trisodium Citrate 30% vs Heparin 5% as Catheter Lock in the Interdialytic Period in Twin-or Double-Lumen Dialysis Catheters for Intermittent Haemodialysis," *Nephrol. Dial Transplant.* 16:1521-1522.
Stile Investigators. (Sep. 1994). "Results of a Prospective Randomized Trial Evaluating Surgery Versus Thrombolysis for Ischemia of the Lower Extremity, The STILE Trial," *Ann. Surg.* 220(3):251-268.
Suggs, W.D. et al. (Aug. 1999). "When is Urokinase Treatment an Effective Sole or Adjunctive Treatment for Acute Limb Ischemia Secondary to Native Artery Occlusion," *Am. J. Surg.* 178:103-106.
Suhocki, P.V. et al. (Sep. 1996). "Silastic Cuffed Catheters for Hemodialysis Vascular Access: Thrombolytic and Mechanical Correction of Malfunction," *American Journal of Kidney Diseases* 28(3):379-386.
Supplemental Partial European Search Report mailed Dec. 30, 2005, for EP Patent Application No. 02791318.5, four pages.
Swischuk, J.L. et al. (Apr. 2001). "Transcatheter Intraarterial Infusion of rt-PA for Acute Lower Limb Ischemia: Results and Complications," *J. Vasc. Interv. Radiol.* 12(4):423-430.
Sze, D.Y. et al. (Dec. 2001). "Treatment of Massive Pulmonary Embolus with Catheter-Directed Tenexteplase," *J. Vasc. Interv. Radiol.* 12(12):1456-1457.
Tang, M. (1993). "Bacteriostatic Saline Flush Interferes with Sodium Measurement on the Ektachem 700," *Clinical Chemistry* 39(9):2032.
Tanswell, P. et al. (Apr. 1992). "Pharmacokinetics and Fibrin Specificity of Alteplase During Accelerated Infusions in Acute Myocardial Infarction," *J. Am Coll Cardiol.* 19(5):1071-1075.
Thomas, S.M. et al. (1999). "Avoiding the Complications of Thrombolysis," *Br. J. Surg.* 86:710.

(56) References Cited

OTHER PUBLICATIONS

Valji, K. et al. (Jun. 1995). "Pulse-Spray Pharmacomechanical Thrombolysis of Thrombosed Hemodialysis Access Grafts: Long-Term Experience and Comparison of Original and Current Techniques," AJR 164:1495-1500.

Valji, K. et al. (Apr. 2000). "Evolving Strategies for Thrombolytic Therapy of Peripheral Vascular Occlusion," J. Vasc. Interv. Radiol. 11(4):411-420.

Vercaigne, L.M. et al. (Apr. 2000). "Antibiotic-Heparin Lock: In Vitro Antibiotic Stability Combined with Heparin in a Central Venous Catheter," Pharmacotherapy 2000 20(4):394-399.

Verstraete, M. (Jul. 2000). "Third-Generation Thrombolytic Drugs," Am. J. Med. 109:52-58.

Wiernikowski, J.T. et al. (1991). "Bacterial Colonization of Tunneled Right Atrial Catheters in Pediatric Oncology: A Comparison of Sterile Saline and Bacteriostatic Saline Flush Solutions," Am. J. Pediat. Hematol Oncol. 13(2):137-140.

Woodhouse, K.A. et al. (1996). "Lysis of Surface-Localized Fibrin Clots by Adsorbed Plasminogen in the Presence of Tissue Plasminogen Activator," Biomaterials 17(1):75-77.

Written Opinion mailed Nov. 7, 2003, for PCT/US02/37878, filed Nov. 25, 2002, six pages.

Written Opinion mailed Jun. 25, 2008, for PCT/US2007/082933, filed Oct. 30, 2007, seven pages.

Yamazaki, M. et al. (1994). "Effects of DX-9065a, an Orally Active, Newly Synthesized and Specific Inhibitor of Factor Xa, Against Experimental Disseminated Intravascular Coagulation in Rats," Thromb. Haemost.72(3):393-396.

Zacharias, J.M. et al. (Jan. 2003). "Alteplase Versus Urokinase for Occluded Hemodialysis Catheters," The Annals of Pharmaotherapy 37:27-33.

Zhou, T. et al. (1998). "Development of a Multiple-Drug Delivery Implant for Intraocular Management of Proliferative Vitreoretinopathy," J. Controlled Release 55:281-295.

Akers, M.J. (Nov. 2002). "Excipient-Drug Interactions in Parenteral Formulations," J. Pharm. Sci. 91(11):2283-2300.

Anonoymous. (Jul. 2006). "Guideline 7. Prevention and Treatment of Catheter and Port Complications," American Journal of Kidney Diseases 48(1)(Supp. 1):S248-S257.

Haymond, J. et al. (2005). "Efficacy of Low-Dose Alteplase for Treatment of Hemodialysis Catheter Occlusions," The Journal of Vascular Access 6:76-82.

Final Office Action mailed Aug. 24, 2007, for U.S. Appl. No. 10/697,142, filed Oct. 30, 2003, ten pages.

Final Office Action mailed Feb. 5, 2009, for U.S. Appl. No. 10/697,142, filed Oct. 30, 2003, ten pages.

Genentech "TNKase (Tenecteplase) Single Bolus" 4 pgs. Jun. 2000.

Merriam-Webster (2013). Online Definition of "Physiological Saline" located at <http://mwl.merriam-webster.com//medical/physiological/%20saline>, last visited Jun. 5, 2013, one page.

Non-Final Office Action mailed Mar. 13, 2007, for U.S. Appl. No. 10/697,142, filed Oct. 30, 2003, six pages.

Non-Final Office Action mailed Jun. 6, 2008, for U.S. Appl. No. 10/697,142, filed Oct. 30, 2003, nine pages.

Non-Final Office Action mailed Dec. 23, 2009, for U.S. Appl. No. 11/533,305, filed Sep. 19, 2006, nine pages.

Non-Final Office Action mailed Jun. 10, 2013, for U.S. Appl. No. 12/822,071, filed internationally Oct. 30, 2007, eight pages.

Tumlin, J. et al. (Apr. 2010, e-pub. Feb. 4, 2010). "A phase III, randomized, double-blind, placebo-controlled study of tenecteplase for improvement of hemodialysis catheter function: TROPICS 3," Clin. J. Am. Soc. Nephrol. 5(4):631 636.

Abbott Laboratories. (2002). "Abbokinase® UROKINASE," located at <http://www.fda.govdownloads/Drugs/DevelopmentApprovalProcess/HowDrugsareDevelopedandApproved/ApprovalApplications/TherapeuticBiologicApplications/ucm080776.pdf>, nine pages.

\* cited by examiner

TISSUE PLASMINOGEN ACTIVATOR VARIANT USES

BACKGROUND OF THE INVENTION

1. Field of the Invention

This invention relates to the use of a tissue-plasminogen activator variant for restoring function in dysfunctional hemodialysis catheters.

2. Description of Related Disclosures

Plasminogen activators are enzymes that cleave the peptide bond of plasminogen between amino acid residues 561 and 562, converting it to plasmin. Plasmin is an active serine proteinase that degrades various proteins, including fibrin.

Currently, five plasminogen activators are approved in the United States for treating coronary thromboses, but none are FDA-approved for catheter-directed thrombolysis. In the past three years, significant clinical research has been performed with use of recombinantly derived agents for catheter-directed therapy (CDT). Techniques have been refined and treatment of deep vein thrombosis (DVT) has been reported to be effective and safe with all available plasminogen activators in non-randomized, non-controlled observational studies (Elsharawy and Elzayat, *Eur. J Vasc. Endovasc. Surg.*, 24: 209-214 (2002); Semba and Dake, *Radiology*, 191: 487-494 (1994); Chang et al., *J. Vasc. Interv. Radiol.*, 12: 247-252 (2001); Castaneda et al., *J. Vasc. Interv. Radial.*, 13: 577-580 (2002); Semba et al., *Tech. Vasc. Interv. Radiol.*, 4: 99-106 (2001); Allie et al., *Am. J. Cardiol.*, 90 (suppl 6A): 108H (2002)). See Verstraete, *Am. J. Med.*, 109: 52-58 (2000) for an overview of third-generation thrombolytic drugs in general.

An early review of the literature suggested that the major complication rate undergoing thrombolysis with recombinant tissue-plasminogen activator (tPA) for peripheral arterial occlusive disease was 5.1% (Semba et al., *J. Vasc. Interv. Radiol.*, 11: 149-161 (2000); Swischuk et al., *J. Vasc. Interv. Radiol.*, 12: 423-430 (2001)). A tPA trial at a dose of 0.04 mg/kg/hr found major complications of 13% (Arepally et al., *J. Vasc. Interv. Radiol.*, 13: 45-50 (2002)).

Initial results of reteplase in the treatment of acute lower extremity arterial occlusions showed a mortality rate of 6% with a currently employed low-dose regimen of 0.5 u/hour (Davidian et al., *J. Vasc. Interv. Radiol.*, 11: 289-294 (2000)). More recently, a pilot study of reteplase employed for thrombolysis of deep venous thrombosis reported a major complication rate of 4% (Castaneda et al., supra).

Tenecteplase (TNK, TNKASE™, Genentech, Inc., South San Francisco, Calif.), a tissue-plasminogen activator, is a sterile, purified glycoprotein of 527 amino acids resulting from modifications of the complementary DNA for natural human tissue plasminogen activator. The modifications yielded a molecule with amino acid substitutions at three sites: the substitution of asparagine for threonine 103, the substitution of glutamine for asparagine 117, and a tetra-alanine substitution at amino acids 296-299 (lysine, histidine, arginine, and arginine). Tenecteplase is a serine protease that converts plasminogen to plasmin in the presence of fibrin, with limited conversion of plasminogen to plasmin in the absence of fibrin. Tenecteplase binds to fibrin in a thrombus and converts plasminogen to plasmin. This initiates local proteolysis of fibrin associated with the thrombus with limited proteolysis of systemic fibrinogen. Tenecteplase has the same mechanism of action as alteplase and has been shown to be potent and effective in promoting clot lysis in vitro (Refino et al., *Thromb Haemost*, 69(6):841 (1993); Keyt et al. *Proc Natl Acad Sci.* USA 91:3670-4 (1994).

In pre-clinical studies, tenecteplase has demonstrated increased potency, higher fibrin specificity, resistance to plasminogen activator inhibitor (PAI-1), and faster clot lysis, with less systemic fibrinolysis, plasminogenemia, and bleeding compared to alteplase (Refino et al., *Thromb. Haemost.*, 70: 313-319 (1993); Keyt et al., supra; Collen et al., *Thromb. Haemost.*, 72: 98-104 (1994); Patel et al., *J. Vasc. Interv. Radiol.*, 12: 559-570 (2001)); Benedict et al., *Circulation*, 92: 3032-3040 (1995)).

In human clinical trials for treatment of acute myocardial infarction (AMI), tenecteplase demonstrated similar efficacy to alteplase, but major blood loss was reduced by 22%, need for blood transfusion was reduced by 23%, and minor bleeding decreased by 16% (Assessment of the Safety and Efficacy of a New Thrombolytic Investigators (ASSENT-2). Single-bolus tenecteplase compared with front-loaded alteplase in acute myocardial infarction: the ASSENT-2 double blind randomized trial. *Lancet*, 354: 716-722 (1999)). There was no significant difference in the rate of intracranial hemorrhage (0.9%). Subjects with an AMI within 6 hours of symptom onset were eligible for this study. The primary objective was to compare the mortality of subjects 30 days after treatment. Safety endpoints included rates of stroke, in-hospital myocardial reinfarction or pulmonary edema/cardiogenic shock, intracranial hemorrhage (ICH), major bleeding (defined as bleeding requiring blood transfusion or leading to hemodynamic compromise), and serious bleeding events. In the group of 16,949 subjects with AMI who were evaluated, there was no difference in the mortality rate at 30 days between tenecteplase and alteplase. In addition, there was no difference in ICH rate between tenecteplase- and alteplase-treated subjects (0.93% vs. 0.94%, respectively). However, there were significantly fewer non-cerebral major bleeding events in tenecteplase- versus alteplase-treated subjects (4.66% vs. 5.94%, respectively; p-value=0.0002), and fewer transfusions (4.25% vs. 5.49%, respectively; p=0.0002). Allergic-type reactions (e.g., anaphylaxis, angioedema, laryngeal edema, rash, and urticaria) were reported in <1% of subjects treated with tenecteplase. Anaphylaxis was reported in <0.1% of subjects treated with tenecteplase; however, causality was not established.

As a result of this study, tenecteplase is currently approved for use in the reduction of mortality associated with acute myocardial infarction (AMI) in weight-tiered doses ranging from 30 to 50 mg and given as a single intravenous bolus. Because of the superior safety profile seen in AMI and its increased clot lysis efficiency, investigators have been exploring the use of tenecteplase in non-coronary applications as an alternative thrombolytic agent (Semba et al., *Tech. Vasc. Interv. Radiol.*, (2001), supra; Sze et al., *J. Vasc. Interv. Radiol.*, 12: 1456-1457 (2001); Razavi et al., *J. Vasc. Interv. Radiol.*, 13: (2), Part 2: S11 (February 2002); Nehme et al., *J. Vasc. Interv. Radiol.*, 13: S109 (2002)).

Allie et al., Tenecteplase in Peripheral Thrombolysis: Initial Safety and Feasibility Experience, abstract 48 of Society of Interventional Radiology, March 2003 (page S17) discloses that continuous tenecteplase infusion (0.25 to 0.50 mg/hour) is a safe and feasible treatment for peripheral chemical thrombolysis. Further, tenecteplase diluted to a 0.0125 mg/ml solution was found to be a feasible treatment for thrombolysing occluded peripheral arteries and veins, with only moderate effect on fibrinogen levels (Burkart et al., *J. Vasc. Interv. Radiol.*, 13: 1099-1102 (2002)), and when combined with eptifibatide, was found to be a feasible treatment for thrombolysing acute peripheral arterial and venous occlusions (Burkart et al., *J. Vasc. Interv. Radiol.*, 14: 729-733 (2003)). Nehme et al., *J. Vasc Intery Radiol*, 13:S109 (2002)

presented preliminary results of a study that evaluated the efficacy of tenecteplase in de-clotting 21 thrombosed arteriovenous polytetrafluoroethylene HD grafts in 14 subjects. Using a lyse-and-wait technique, tenecteplase at 2 mg and heparin at 3000 U were injected into the grafts via an angio-catheter. The duration of drug treatment was not published, but the authors stated that the mean procedural time was 65 minutes. Technical success, defined as complete graft recanalization, was 95% (20 of 21 grafts), and clinical success, defined as one successful HD after treatment, was 90% (19 of 21). Prior to additional mechanical thrombolysis, pulse was restored in 28% of the grafts (6 of 21). The authors reported one minor bleeding event at a previous graft puncture site.

Abbas et al. *J. Amer. Coll. Cardiol.*, 46: 793-8 (2005) evaluated the safety and efficacy of intracoronary thrombolysis in 85 subjects with chronic total occlusion for >3 months and in whom a prior attempt at recanalization with percutaneous coronary intervention (PCI) was unsuccessful. Subjects received either a weight-adjusted dose (2-5 mg/hr) of alteplase (n=61) or a standard dose (0.5 mg/hr) of tenecteplase (n=24) for 8 hours, followed by PCI; the total dose was divided between the guide catheter and a 3-French intracoronary infusion catheter. Following intracoronary thrombolysis, recanalization was achieved in 54% of all subjects (both treatment groups combined) on repeat PCI. By multivariate analysis, lesion tapering and lack of bridging collaterals were the only predictors of success. Adverse events included hematoma (8% of all subjects) and bleeding requiring transfusion (3.5% of all subjects).

Tenecteplase is available in a commercially supplied 50-mg vial and approved for a single-bolus administration in patients with AMI (TNKASE™. Full prescribing information, 2002 *Physicians Desk Reference*, Thomas Medical Economics Co., Montvale, N.J.). When used in approved indications, tenecteplase is reconstituted in sterile water to achieve a final concentration of 5 mg/mL and administered intravenously as a single weight-adjusted bolus.

CATHFLO®ACTIVASE® (alteplase) is indicated for the restoration of function to central venous access (CVA) devices as assessed by the ability to withdraw blood. Approval was based on two pivotal Genentech-sponsored clinical trials of alteplase for the restoration of catheter function in adult and pediatric subjects over the age of two. Subsequently, a third trial in pediatric subjects (<17 years of age, including some <2 years of age) was performed. All three studies, whether placebo-controlled, double-blind or open-label trials, demonstrated that alteplase, when given at a dose of up to 2 mg/2 mL for up to two administrations, each followed by a dwell time of up to 120 minutes, is a safe and effective treatment for the restoration of catheter function in both adult and pediatric patients with occluded CVA catheters. Following administration of the first dose of alteplase, the rate of restoration of function to dysfunctional catheters after a dwell time of up to 120 minutes was 73.9%-76.5% for subjects ≥2 years of age and 69.1% for subjects <2 years of age. The rate of restoration of function following administration of up to two doses of alteplase was 83.5%-89.9% for subjects ≥2 years of age and 80.0% for subjects <2 years of age. A total of 39 of 1454 subjects (2.7%) reported serious adverse events during the three studies. All serious adverse events except three were judged to be unrelated to the alteplase. No ICHs, embolic events, or alteplase-related major bleeding were reported during the trials. The most common serious adverse event in these trials was sepsis/bacteremia (18%).

For peripheral catheter-directed thrombolytic therapy, lyophilized tenecteplase is reconstituted in sterile water (5 mg/mL) and further diluted in normal saline (0.01 to 0.25 mg/mL) (Semba et al., *Tech. Vasc. Interv. Radiol.*, supra, (2001); Allie et al., *Am. J. Cardiol.*, supra); Razavi et al., supra; Semba et al., *J. Vasc. Interv. Radiol.*, 13: (2), Part 2: S75 (February 2002). Specifically, Razavi et al., supra, reports that using a 0.01 mg/mL dilution of tenecteplase in normal saline infused at 25 to 50 mL/hr (0.25-0.5 mg/hr) results in angiographic efficacy in arterial and venous clot lysis (Razavi et al., supra). Additionally, Razavi et al., *J. Endovasc. Ther.*, 9:593-598 (2002) disclose that such doses of tenecteplase are safe and effective in peripheral catheter-directed thrombolytic therapy of arterial occlusions and deep vein thrombosis.

According to the United States Renal Data System, there were over 440,000 persons in the United States with end-stage renal disease at the end of 2003 (National Institutes of Health, U.S. Renal Data System. USRDS 2005 annual data report: atlas of end-stage renal disease in the United States. Bethesda (Md.): National Institutes of Health, National Institute of Diabetes and Digestive and Kidney Diseases (2005)). Of these, the vast majority underwent regular hemodialysis (HD), generally three times per week. Many of these patients receive HD through tunneled central venous catheters. For these patients, low catheter flow rates due to thrombotic obstruction of the lumens remain a frequent complication and have been estimated to affect 3%-10% of all HD sessions and 87% of all catheters at some time prior to their removal (Moss et al., *Am J Kidney Dis;* 12:492-8 (1988); Gibson and Mosquera, *Nephrol Dial Transplant* 1991;6:269-74 (1991); Suhocki et al., *Am J Kidney Dis*, 28:379-86 (1996)).

The Kidney Dialysis Outcome Quality Initiative (KDOQI) Clinical Practice Guidelines for Vascular Access defines HD catheter dysfunction as the "failure to attain and maintain an extracorporeal blood flow (≥300 mL/min) sufficient to perform HD without significantly lengthening HD treatment" (National Kidney Foundation, K/DOQI clinical practice guidelines for vascular access: updated 2000. *Am J Kidney Dis* 37:S137-81 (2001)). The KDOQI guidelines for managing failing catheters recommend the use of thrombolytics as first-line therapy.

The use of alteplase as an intra-luminal dwell to treat HD catheter dysfunction has been reported, for example, in Daeihagh et al. *Am J Kidney Dis* 36:75-9 (2000); Habowski et al., *J Am Soc Nephrol* 11:185A (2000); O'Mara et al., *J Am Soc Nephrol.*, 11:292A (2000); Roberts et al., *J Am Soc Nephrol* 11:195A (2000); Zacharias et al., *Ann Pharmacother.*, 27-33 (2000); Hammes et al., *J Am Soc Nephol* 12:290A (2001); Spry and Miller, *Dial Transplant* 30:10-2 (2001); Cairoli O. Practical application: using t-PA (Cathflo™ Activase®) overnight in catheter clearance on tunnel catheters used for hemodialysis. *Proceedings of the 22nd Annual Conference on Dialysis;* Tampa (Fla.) (Mar. 4-6, 2002); Eyrich et al. *Am J Health Syst Pharm* 59:1437-40 (2002); Little and Walshe *Am J Kidney Dis* 39:86-91 (2002); and Dowling et al., *Nephrol Nurs J;* 31:199-200 (2004). Alteplase doses of 1 to 2 mg were given in varying volumes, with dwell times ranging from 20 minutes to 96 hours. Most of these studies have small numbers of patients, use different dosing regimens, have little safety information, and have varied definitions of efficacy. Thus, no thrombolytic has been studied in randomized, well-controlled clinical trials or been approved by the U.S. Food and Drug Administration (FDA) for treatment of occluded HD catheters.

U.S. patent application Ser. No. 10/697,142 filed 30 Oct. 2003 discloses using diluted solutions of tenecteplase to treat pathological collections of fibrin-rich fluids, for example, the fluids found to obstruct catheters, including HD catheters.

There is a need for using a fibrin-specific plasminogen activator efficaciously and uniformly to clear out HD catheters containing pathological collections of fluid. For example, there is a need for HD catheter-directed thrombolysis in a clinical setting that allows higher doses of tenecteplase than set forth in U.S. patent application Ser. No. 10/697,142 filed 30 Oct. 2003. Specifically, there is a need to administer a fibrin-specific plasminogen activator locally into the HD catheter lumen without systemic exposure to provide a way to salvage catheters with suboptimal flow rates while minimizing the risk of adverse events associated with systemic use of such agent. Because of the time constraints of HD sessions, there is a need for an agent such as tenecteplase, with high potency, high fibrin specificity, and efficiency to rapidly lyse clots. Furthermore, a continuing need exists for the prevention and removal of fibrin from such HD devices, as certain bacteria have binding sites that favor sticking to fibrin, in particular.

SUMMARY OF THE INVENTION

Accordingly, the invention is as claimed. In one embodiment of the invention herein, a method is provided for restoring function in a dysfunctional hemodialysis catheter indwelling in a mammal, which catheter has a blood flow rate (BFR) of less than 300 mL/minute, which method comprises administering tenecteplase in a total dose of about 3 to 4 mg locally into all catheter lumens and allowing the tenecteplase to dwell in the catheter for from about one hour to about 72 hours, such that the flow rate of the catheter is no longer obstructed.

In one embodiment, the dysfunctional hemodialysis catheter additionally has a BFR at least 25 mL/min below the prescribed BFR at an arterial pressure of −250 mmHg during the first 30 minutes of the hemodialysis.

Preferably, the tenecteplase is in a solution of sterile water for injection or bacteriostatic water for injection. Preferably, the tenecteplase dwells in the catheter until the BFR of the catheter is improved over the BFR before administration of tenecteplase and the improvement maintained for at least 48 hours. In other preferred embodiments, the tenecteplase is in sterile water for injection, and/or the tenecteplase is administered in a total dose of about 4 mg into all catheter lumens, wherein preferably about 2 mg/2 mL of tenecteplase is administered to each of two catheter lumens.

In other preferred aspects, the tenecteplase is instilled into the catheter for about one hour or as an extended dwell of from over about one hour to about 72 hours. Preferably, the dwell is from about 2 to about 48 hours. In another preferred aspect, the catheter is contacted with the solution for at least about five days to remove fibrin-bound blood clots.

In further preferred aspects, treatment may be repeated, i.e., the tenecteplase is administered more than once. One aspect of this procedure is that the tenecteplase is administered at each hemodialysis session that the mammal undergoes. In another preferred embodiment, no re-treatment is performed, i.e., the tenecteplase is administered only once or twice as an initial dose and then as an extended-dwell dose. Most preferably, the tenecteplase is administered only once, i.e., as one dose.

In other preferred aspects, the mammal undergoes hemodialysis after administration of the tenecteplase. In further embodiments, the mammal is a human.

In another aspect, a kit is provided comprising a container comprising a solution comprising tenecteplase, and instructions for using the solution to restore function in a dysfunctional hemodialysis catheter indwelling in a mammal, which catheter has a BFR of less than 300 mL/minute, which instructions direct the user to administer tenecteplase in a total dose of about 3 to 4 mg locally into all catheter lumens and allow the tenecteplase to dwell in the catheter for from about one hour to about 72 hours, such that the flow rate of the catheter is no longer obstructed.

In a further aspect, the invention concerns a method comprising manufacturing tenecteplase for restoring function in a dysfunctional hemodialysis catheter indwelling in a mammal, which catheter has a blood flow rate (BFR) of less than 300 mL/minute.

In a still further aspect, the invention concerns tenecteplase for use to restore function in a dysfunctional hemodialysis catheter indwelling in a mammal, which catheter has a blood flow rate (BFR) of less than 300 mL/minute.

The invention herein hence provides for using tenecteplase to treat hemodialysis catheters that are obstructed and become dysfunctional, particularly those that become dysfunctional due to pathological collections of fibrin-rich fluids residing in the catheter.

DESCRIPTION OF THE PREFERRED EMBODIMENTS

Definitions

As used herein, "hemodialysis catheter" or "HD catheter" refers to a dialysis catheter generally, but not necessarily, constructed of plastic polymers, e.g., polyurethane, silicone, or other polymers, that is useful in catheter-directed therapy (i.e., delivering medical therapy) to effect hemodialysis. The catheters herein are indwelling catheters, such as intravenous or arterial hemodialysis catheters, including those that are tunneled. The catheter preferably is not an implantable port, non-cuffed catheter, or non-tunneled catheter. The HD catheter is preferably not implanted in the jugular vein. Preferably, the HD catheter lumens doe not require flow reversal. Most preferred is a cuffed tunneled HD catheter. As used herein, a "dysfunctional" HD catheter is one that fails to attain and maintain an extracorporeal blood flow (≥300 mL/min) sufficient to perform HD without significantly lengthening HD treatment, as defined by the National Kidney Foundation, K/DOQI clinical practice guidelines for vascular access: updated 2000. *Am J Kidney Dis* 37:S137-81 (2001). Generally, such dysfunctional catheter has a BFR of less than 300 mL/minute typically at a maximum negative arterial pressure of 250 mmHg. Such dysfunctional catheters preferably show a demonstrated BFR of equal to or greater than 300 mL/minute in at least one HD session in the seven days prior to treatment by the method herein. HD catheters are not dysfunctional if they have a sustainable BFR of equal to or greater than 300 mL/minute following subject repositioning. The dysfunctional catheters herein preferably have no evidence of mechanical, non-thrombotic occlusion (e.g., a kink in the catheter or suture constricting the catheter), or occlusion caused by known fibrin sheath.

"Restoring function" means allowing HD to be carried out successfully at least once after treatment with the tenecteplase, that is, generally without obstruction and at the minimal flow rate to allow HD to proceed as prescribed by the physician. In generally, this means that function is restored when the catheter with suboptimal flow rates is salvaged and the BFR is restored to at least 300 mL/minute. While the subject must exhibit clinical treatment success at their first HD visit after treatment for restoration to occur, preferably the subject shows maintained catheter patency over a period of time beyond the first visit.

An indication of functional restoration beyond HD success is the percent improvement from baseline BFR at the end of HD administered at the first visit. The baseline BFR is the BFR measurement obtained to determine if the patient is eligible for treatment. In one preferred embodiment, after a dwell time of the tenecteplase in the patient's catheter of about one hour, the tenecteplase instillation is discontinued and all patients undergo full HD. BFR is then generally measured during the last 30 minutes of HD to assess catheter function. In this preferred mode, subjects with a BFR of ≥300 mL/min continuously sustained for at least the last about 30 minutes and an increase from baseline BFR of ≥25 mL/min at the end of HD are considered a treatment success, and subjects with a BFR of ≥300 mL/min and an increase from baseline BFR of <25 mL/min and subjects with a BFR of <300 mL/min are considered to have had treatment failure. Also, in a preferred embodiment such subjects have a urea reduction ratio (URR) of at least about 65% as assessed by pre- and post-HD BUN measurements at the first HD visit after treatment with tenecteplase.

In another embodiment of functional restoration, after a dwell time of the tenecteplase in the patient's catheter of about one hour, the patient undergoes full HD, and BFR is measured during the last 30 minutes of HD to assess catheter function. Subjects with a BFR of ≥200 mL/min but <300 mL/min at the end of HD at the first visit get a second dose instilled for an extended dwell time, until the start of the second visit (up to 72 hours). The extended-dwell dose of tenecteplase is withdrawn from the catheter at the beginning of the second visit, and BFR is measured at the beginning of HD. Patients undergo full HD, and BFR is again measured during the last 30 minutes of HD. In this second preferred mode, subjects with a BFR of ≥300 mL/min continuously sustained for at least the last about 30 minutes and an increase from baseline BFR of ≥25 mL/min at the end of HD at the first or second visit are considered to be a treatment success. Those who have re-occlusion of their HD catheter (BFR of <300 mL/min) within 21 days of the first visit exit the initial treatment course and enter the retreatment course, during which they receive another dose of tenecteplase. After a dwell time of 1 hour, patients undergo full HD, and BFR is measured during the last 30 minutes of HD. In that case, patients with a BFR of ≥300 mL/min and an increase from baseline BFR of <25 mL/min and subjects with a BFR of <300 mL/min are considered to have had treatment and re-treatment failure.

"Administering" means infusing or instilling the drug into the catheter. This generally means that the lumen of the catheter is flushed with the tenecteplase. Allowing the tenecteplase to "dwell" means that the tenecteplase stays in the catheter to perform its function of restoring flow rate; such "dwell" generally means an intra-luminal dwell.

As used herein, a "pathological collection of a fibrin-rich fluid" refers to gathered fluids containing an excess of fibrin that cause problems in a hemodialysis catheter. The fluids may be from any source, including blood, cerebrospinal fluid, urine, and fluid from the peritoneal, pleural, or pericardial cavity, and, due to their high fibrin content, can be treated with a thrombolytic drug. Hence, this collection includes intravascular as well as non-vascular collections of fluid. This collection of fluid is contained in a hemodialysis catheter. This fluid is pathological preferably because it causes the hemodialysis catheter to be dysfunctional, thereby limiting effective hemodialysis. Effective hemodialysis is hemodialysis that will function properly for the subject being treated.

The term "mammal" for the purposes of treatment refers to any animal classified as a mammal, including but not limited to, humans, sport, zoo, pet, and domestic or farm animals, such as dogs, cats, cattle, sheep, pigs, horses, and primates, such as monkeys or humans. Preferably the mammal is a human. The mammal herein must require HD, and preferably must have been prescribed at a BFR of equal to or greater than 300 mL/minute. The mammals preferably have had their HD catheter inserted at least two days prior to their treatment. The eligible mammals also preferably use the same catheter for at least four consecutive HD sessions on the same type and model of HD apparatus. The mammal being treated preferably is able to have fluids infused at the volume necessary to instill the tenecteplase into the HD catheter. The mammal may be an adult or a pediatric mammal (e.g., for a human less than 18 years of age), but is preferably an adult, i.e., for a human at least 18 years old.

A "therapeutic composition" or "composition," as used herein, is defined as comprising tenecteplase, sterile water for injection or bacteriostatic water for injection, as well as any optional pharmaceutically acceptable carrier(s), such as minerals, proteins, and other excipients known to one skilled in the art. Preferably, the tenecteplase is in the form of a lyophilized powder reconstituted in one of these types of waters.

As used herein, "solution" refers to a soluble mixture of ingredients, including complete solvation of the ingredients.

As used herein, the term "tenecteplase," also known as TNK-tPA or TNKASE™ brand of tissue-plasminogen activator variant, refers to a tPA variant designated T103N, N117Q, K296A, H297A, R298A, R299A available from Genentech, Inc. wherein Thr103 of wild-type tPA is changed to Asn (T103N), Asn117 of wild-type tPA is changed to Gln (N117Q), and Lys-His-Arg-Arg (SEQ ID NO:1) 296-299 of wild-type tPA is changed to Ala-Ala-Ala-Ala (SEQ ID NO:2) (KHRR296-299AAAA). See the background section herein and U.S. Pat. No. 5,612,029.

As used herein, "sterile water for injection" or "SWFI" refers to the same substance as defined by the United States Pharmacopeia (USP), which is a sterile, non-pyrogenic preparation of water for injection that contains no bacteriostat, antimicrobial agent, or added buffer and is supplied only in single-dose containers to dilute or dissolve drugs for injection.

"Normal saline" refers to an aqueous solution of water containing 0.9% sodium chloride. It is also known as 0.9% sodium chloride injection USP, non-heparinized normal saline. Such saline is generally used clinically as a diluent for drugs administered by injection and as a plasma substitute.

"Bacteriostatic water for injection" or "BWFI" refers to a mixture of water and varying amounts of benzyl alcohol with no other ingredients as defined by the United States Pharmacopeia (USP).

Modes for Carrying Out the Invention

In one aspect of the invention herein, a method is provided for restoring function in a dysfunctional hemodialysis catheter indwelling in a mammal, which catheter has a BFR of less than 300 mL/minute, which method comprises administering tenecteplase in a total dose of about 3 to 4 mg locally into all catheter lumens (there are typically two lumens in the catheter) and allowing the tenecteplase to dwell in the catheter for from about one hour to about 72 hours, such that the flow rate of the catheter is no longer obstructed.

Preferably, the tenecteplase dwells in the catheter until the BFR of the catheter is improved over the BFR before administration of tenecteplase and the improvement maintained for at least 48 hours. In other preferred aspects, the tenecteplase is instilled into the catheter for about one hour or as an extended dwell of from over about one hour to about 72 hours. Preferably, the dwell is from about 2 to about 48 hours. In another preferred aspect, the catheter is contacted with the solution for at least about five days to remove fibrin-bound blood clots. In further embodiments, the tenecteplase may be administered once or more than once, and preferably only after HD sessions. Preferably, the mammal is a human.

Generally, screening and the first administration of tenecteplase is at the first visit by the subject for tenecteplase treatment followed by HD. The subjects are generally screened for eligibility based on the inclusion and exclusion criteria. Eligible subjects, with a BFR of <300 mL/min (all BFR measurements are preferably based on a maximum negative arterial pressure of 250 mmHg) at the beginning of HD (typically within the first 30 minutes), receive tenecteplase. The BFR measurement obtained to determine study eligibility is the baseline BFR.

In one embodiment, human patients preferably receive a concentration of tenecteplase of about 1 mg/mL, wherein the dose is about 2 mg/2 mL per lumen with a total dose of about 4 mg. In other words, the patient preferably receives a dose of about 2 mg/2 mL of tenecteplase, typically instilled into each of the two lumens of the HD catheter. Preferably after a dwell time of about one hour, the tenecteplase instillation is discontinued and all subjects undergo full HD. BFR is then generally measured during the last 30 minutes of HD to assess catheter function. In this preferred mode, subjects with a BFR of ≥300 mL/min continuously sustained for at least the last 30 minutes and an increase from baseline BFR of ≥25 mL/min at the end of HD are considered a treatment success, and subjects with a BFR of ≥300 mL/min and an increase from baseline BFR of <25 mL/min and subjects with a BFR of <300 mL/min are considered to have had treatment failure.

In this situation, subjects with a BFR of ≥300 mL/min at the end of HD at the first visit are preferably not further treated. Subjects with a BFR of <300 mL/min at the end of HD at the first visit are preferably treated with 2 mL (2 mg) of tenecteplase at the beginning of the next HD session if their BFR is still <300 mL/min at that time. After a dwell time of one hour, preferably the tenecteplase is discontinued and subjects undergo full HD. BFR is again measured during the last 30 minutes of HD to assess catheter function.

In this one preferred embodiment, subjects with treatment success at the first or second HD visit are assessed for HD catheter patency by measuring BFR at the beginning of HD (within the first 30 minutes) at each of the two visits that follow final tenecteplase exposure (i.e., the second and third visits for subjects who receive one dose of tenecteplase and the third and fourth visits for subjects who receive two doses of tenecteplase).

In a second preferred embodiment, the human patients receive up to three doses of tenecteplase. Subjects will receive one or two doses during an initial treatment course, and eligible subjects who experience re-occlusion of their catheter within 21 days of the first visit will receive an additional dose as part of a retreatment course.

Specifically, the patients are screened and treated at the first visit of the initial treatment course. The patients are screened for eligibility based on the inclusion and exclusion criteria. Eligible subjects, with a BFR of <300 mL/min (all BFR measurements are based on a maximum negative arterial pressure of 250 mmHg) at the beginning of HD (within the first 30 minutes), are treated with tenecteplase. The baseline BFR is as defined above. The patients are dosed with 2 mL (2 mg) of tenecteplase instilled into each of the two lumens of the HD catheter. After a dwell time of one hour, the tenecteplase is withdrawn and all patients undergo full HD. BFR is measured during the last 30 minutes of HD to assess catheter function. Patients with a BFR of ≥300 mL/min continuously sustained for at least the last 30 minutes and an increase from baseline BFR of ≥25 mL/min at the end of HD are considered to have had treatment success. Subjects with a BFR of ≥300 mL/min and an increase from baseline BFR of <25 mL/min and subjects with a BFR of <300 mL/min are considered to have had treatment failure.

Subjects with a BFR of <200 mL/min at the end of HD at the first visit, or a BFR of ≥300 mL/min and an increase from baseline BFR of <25 mL/min, are no longer treated. Subjects with a BFR of ≥200 mL/min but <300 mL/min at the end of HD at the first visit have 2 mL (2 mg) of tenecteplase instilled into each lumen of their catheter as part of the initial treatment course. The dose is left to dwell for an extended time, until the second HD session at the second visit (up to about 72 hours later). Patients who receive the extended-dwell dose of tenecteplase have the dose withdrawn from their catheter at the beginning of the second visit and then have BFR measured at the beginning of HD (within the first 30 minutes). Subjects undergo full HD, and BFR is again measured during the last 30 minutes of HD.

Subjects who have treatment success at the first or second visit and have re-occlusion of their HD catheter (BFR of <300 mL/min) within 21 days of the first visit discontinue the initial treatment and enter a retreatment course during which they again have 2 mL (2 mg) of tenecteplase instilled into each lumen, followed by a one-hour dwell time (at retreatment Visit 1).

Subjects who have treatment success at the first or second visit, or Retreatment Visit 1 are assessed for HD catheter patency by measuring BFR at the beginning of HD (within the first 30 minutes) at each of the two visits that follow final tenecteplase exposure.

This second option is designed to assess the efficacy of serial administration of up to three doses of tenecteplase for restoration of function to dysfunctional HD catheters, whereas the first option assesses efficacy of serial administration of up to two doses.

Hence, the invention herein includes not only administering a first dose of tenecteplase to those subjects requiring restoring of function of their hemodialysis catheters, but also administering subsequent doses of tenecteplase, typically in the same amount, but the amounts can differ. This treatment with multiple doses or re-treatment can be done once or several times, for example, at the beginning of each HD session. It may be done as many times as needed to ensure catheter patency and successful HD. Preferably, the tenecteplase is dosed only once or twice (as an initial instill and/or as an extended-dwell dose), and most preferred only once.

The tenecteplase may be administered in the form of a stable solution comprising tenecteplase and an appropriate form of water, especially sterile water for injection or bacteriostatic water for injection, along with any optional ingredients such as normal saline. While the tenecteplase solution useful herein may be prepared in any way, it is preferably prepared by reconstituting a lyophilized powder of tenecteplase in sterile water for injection or bacteriostatic water for injection. The tenecteplase is preferably administered in a total dose of about 4 mg into all catheter lumens, preferably two lumens. Most preferably, the tenecteplase is in sterile water for injection.

The amount of tenecteplase provided is that which will effect lyse any clots that occlude the catheter and otherwise restore function in dysfunctional hemodialysis catheters in a clinical or medical setting (with clinical and technical endpoints such as those set forth above in the definition section), but will not exceed that which would be a dangerous level in vivo so as to cause complications. Examples of major adverse events include intracranial hemorrhages (ICHs), major bleeding, embolic events, thrombosis, catheter-related bloodstream infections (CRBSIs), and catheter-related complications, as well as any procedure-related adverse event requiring additional procedures. Examples of minor bleeding complications include an access site hematoma greater than 5 cm that did not require any specific treatments or bleeding at any site and/or that was managed conservatively without the need for transfusion, evacuation, or prolongation of hospital stay.

According to the invention herein, reconstituted tenecteplase is formulated in a concentration of about 0.75 to 1 mg/mL to provide a dose of about 1.5 mg/2 mL to 2 mg/ 2 mL per catheter lumen, preferably in one of the waters as noted herein and optionally with other ingredients. Most preferably, the tenecteplase is formulated at a concentration of about 1 mg/mL (to provide a dose of about 2 mL of 2 mg of tenecteplase per lumen).

Compositions particularly well suited for the clinical administration of the tenecteplase used to practice this invention include sterile aqueous solutions or sterile hydratable powders such as lyophilized protein. Preferably, this formulation is derived from a lyophilized powder of tenecteplase that is reconstituted in water, preferably sterile water for injection or bacteriostatic water for injection. A buffer such as arginine base in combination with phosphoric acid is also typically included at an appropriate concentration to maintain a suitable pH, generally from 5.5 to 7.5. In addition or alternatively, a compound such as glycerol may be included in the formulation to help maintain the shelf-life. The formulation preferably comprises arginine, phosphoric acid, and an emulsifying agent such as a polyoxyethylene sorbitan fatty ester such as POLYSORBATE 20™ polyoxyethylene 20 sorbitan monolaurate, POLYSORBATE 80™ polyethylene sorbitan monooleate, or POLYSORBATE 65™ polyoxyethylene 20 sorbitan tristearate, which, in some embodiments, accompany the tenecteplase that is lyophilized.

In a less preferred embodiment, an appropriate amount of a pharmaceutically acceptable salt is also used in the formulation to render the formulation isotonic. For example, a non-lyophilized sterile solution might optionally, but not preferably, contain normal saline.

Tenecteplase is commercially available as a sterile, preservative-free, lyophilized powder in a vial containing 52.5 mg of tenecteplase, 0.55 g of L-arginine, 0.17 g of phosphoric acid, 4.3 mg of POLYSORBATE 20™ polyoxyethylene 20 sorbitan monolaurate supplied with a 10-mL syringe of sterile water for injection USP. Alternatively, the tenecteplase can be supplied with a 10-mL syringe of bacteriostatic water for injection. The preferred water for injection herein is sterile water for injection.

As one example of an appropriate dosage form, a vial containing about 50 mg of tenecteplase, as well as arginine, phosphoric acid, and a POLYSORBATE™ emulsifier is reconstituted with 50 mL of sterile water for injection.

In another embodiment, to reconstitute the product, about 10 mL of preservative-free sterile water for injection USP is mixed with the tenecteplase powder under sterile conditions to produce a final concentration of about 1 mg/mL. Alternatively, tenecteplase is reconstituted to a concentration of about 1 mg/mL in BWFI (0.9%) with full viability of protein. Unused reconstituted tenecteplase may be stored at controlled room temperature (15-30° C.) for up to 8 hours or under refrigeration (2-8° C.) for 24 hours.

In a small-vial configuration, a vial may contain 2 mg of tenecteplase in 2 mL of the water for injection. Vials with weights and volumes in between about 1 mg and 4 mg and between about 1 mL and 4 mL, respectively, are also contemplated herein.

Since the procedures herein using tenecteplase involve total doses of about 2-3 mg for catheter clearance, the reconstituted tenecteplase may be readily frozen for later use. Many institutions are reconstituting and freezing smaller aliquots (2- and 5-mL syringes) of tenecteplase for future use to minimize waste and decrease costs.

Visual inspection of the solution for precipitates is recommended after dilution and before administration. Tenecteplase is preservative-free and is theoretically susceptible to bacterial contamination and biochemical degradation when left at room temperature for more than 8 hours. Although the manufacturer recommends changing the solution after 24 hours, the drug should be physically and chemically stable for 24 hours.

The tenecteplase may be instilled into the catheter for up to about one hour or for about one hour, or may be instilled longer as an extended dwell of from over about one hour to about 72 hours, preferably about 2 hours to 48 hours. More than about 72 hours may also be needed. Preferably, the amount is about one hour or up to about 24 hours. If fibrin-bound blood clots are being removed from a catheter, the catheter may be contacted with the solution herein for at least about 5 days, preferably about 6 to 15 days.

The tenecteplase solution herein may be instilled or infused into the catheter by any suitable technique. The skilled practitioner would be easily able to devise methods of administration of the solution herein based on the general knowledge in the literature on lytic administration.

The effects of administration of tenecteplase can be measured by a variety of assays known in the art, as noted in the definitions above, such as the percent improvement from baseline BFR at the end of HD at the first visit, the urea reduction ratio as assessed by pre- and post-HD BUN measurements, the success of HD treatment following the lytic indwelling, etc. Physicians should continue to use the catheter-based modality with which they are most comfortable.

Risk factors for adverse bleeding with tenecteplase are similar to those associated with alteplase, UK, and other plasminogen activators. Variables associated with adverse bleeding risks include increased tenecteplase dose, duration of infusion, adjunctive anti-thrombotic therapy (e.g., heparin, aspirin, or other anti-platelet agents as noted herein), hypertension, increasing age, severity of ischemia, and female gender. Physicians should be aware of these risk factors and use appropriate caution during treatment. If adverse bleeding occurs during infusion therapy, tenecteplase should be immediately terminated and blood products (fresh frozen plasma or cryoprecipitate) administered to reverse hypocoagulability.

The tenecteplase is preferably administered without any other active drug. However, the invention includes circumstances wherein an active drug other than tenecteplase is infused into the catheter. Examples of such co-agents include blood thinners such as heparin and heparin analogs including low-molecular-weight heparin such as tinzaparin, certoparin, parnaparin, nadroparin, ardeparin, enoxaparin (LOVENOX™, Aventis Pharma, Bridgewater, N.J.), reviparin, reviparin and dalteparin, warfarin (3-(alpha-acetonyl-benzyl)-4-hydroxycoumarin, or COUMADIN®), or aspirin; anti-coagulants such as tPA; tPA variants such as reteplase; urokinase; streptokinase; and alfimeprase.

Other drugs may be administered directly to the subject while undergoing HD treatment and administration of tenecteplase. However, it is preferable if no other thrombolytics are administered directly to the patient during this time.

These co-agents may be administered to the catheter by a route and in an amount commonly used therefor, contemporaneously or sequentially with the tenecteplase. When the tenecteplase is used contemporaneously with one or more other drugs, a pharmaceutical unit dosage form containing such other drugs in addition to the tenecteplase is preferred. Tenecteplase is incompatible and may precipitate when mixed directly with unfractionated heparin; concomitant heparin should be given by a separate means. An opaque diluent indicates precipitation of drug and may be associated with decreased efficacy. Such additional molecules are suitably present or administered in combination in amounts that are effective for the purpose intended, typically less than what is used if they are administered alone without the tenecteplase.

The invention also provides kits. In one embodiment, the kit comprises a container comprising a solution that contains at least tenecteplase (preferably in sterile water for injection or bacteriostatic water for injection), and instructions for using the solution to restore function in a dysfunctional hemodialysis catheter indwelling in a mammal, which catheter has a BFR of less than 300 mL/minute, which instructions direct the user to administer tenecteplase in a total dose of about 3 to 4 mg locally into all catheter lumens and allow the tenecteplase to dwell in the catheter for from about one hour to about 72 hours, such that the flow rate of the catheter is no longer obstructed. The preferred embodiments of the instruction guidelines are noted above for the method of restoration.

The kit may also comprise instructions for re-administration. It may also comprise a further container with a co-agent, as defined above, as active ingredient with instructions for co-administration thereof in an effective amount with the solution. A preferred such embodiment is a container comprising abciximab, eptifibatide, tirofiban hydrochloride, heparin, or warfarin with instructions for co-administration thereof in an effective amount with the diluted solution.

These further instructions included with the kit generally include information as to dosage, dosing schedule, and other guidance for the treatment of the HD catheter. The containers of tenecteplase may be unit doses, bulk packages (e.g., multi-dose packages), or sub-unit doses.

In the kit, tenecteplase may be packaged in any convenient, appropriate packaging. For example, if the tenecteplase is a freeze-dried formulation, an ampoule or vial with a resilient stopper is preferably used as the container, so that the drug may be easily reconstituted by injecting fluid through the resilient stopper. Ampoules with non-resilient, removable closures (e.g., sealed glass) or resilient stoppers are most conveniently used for solutions of tenecteplase ready for use in the catheter. In this latter case, the instructions preferably specify placing the contents of the vial in a catheter for immediate delivery.

Various features and aspects of the present invention are illustrated further in the examples that follow. While these examples are presented to show one skilled in the art how to operate within the scope of the invention, they are not intended in any way to serve as a limitation upon the scope of the invention. The disclosure of all citations herein is expressly incorporated herein by reference.

EXAMPLE 1

The goal of the study set forth in this Example is to examine the efficacy and safety of tenecteplase in the restoration of function to dysfunctional HD catheters, compared with a placebo control.

List of Abbreviations and Definition of Terms

| Abbreviation | Definition |
| --- | --- |
| AE | adverse event |
| AMI | acute myocardial infarction |
| BFR | Blood flow rate |
| BUN | Blood urea nitrogen |
| CRBSI | catheter-related blood stream infection |

-continued

| Abbreviation | Definition |
| --- | --- |
| CVA | central venous catheter |
| CRF | Case Report Form |
| DMC | Data Monitoring Committee |
| EC | Ethics Committee |
| FDA | Food and Drug Administration |
| GCP | Good Clinical Practice |
| HD | Hemodialysis |
| ICH | intracranial hemorrhage |
| IND | Investigational New Drug |
| IRB | Institutional Review Board |
| IVRS | interactive voice response system |
| KDOQI | Kidney Dialysis Outcome Quality Initiative |
| PCI | percutaneous coronary intervention |
| QLab | Quintiles Laboratories |
| RT | Retreatment |
| SAE | serious adverse event |
| SDV | source data verification |
| SWFI | Sterile Water for Injection |
| URR | urea reduction ratio |

Objectives of Study
    To evaluate the efficacy of tenecteplase compared with placebo in improving blood flow rate (BFR) in dysfunctional hemodialysis (HD) catheters following a one-hour dwell time
    To evaluate the safety of tenecteplase in the treatment of subjects with dysfunctional HD catheters
Study Design
    This is a Phase III, randomized, double-blind, placebo-controlled study conducted at approximately 40 centers in the United States. Approximately 150 subjects who require HD and have a dysfunctional HD catheter, defined as a BFR of <300 mL/min and at least 25 mL/min below the prescribed BFR at an arterial pressure of −250 mmHg (or at institutional guidelines for maximum negative arterial pressure, not to exceed 250 mmHg) during the first 30 minutes of HD, will be enrolled in the study. Subjects will be classified by baseline BFR into three strata: 0-199 mL/min, 200-274 mL/min, and 275-299 mL/min. Enrollment in the 0-199 mL/min and 275-299 mL/min strata will be limited to a maximum of 10% of subjects in each.

The study will consist of three to four visits that correspond to consecutive HD sessions based on each subject's regular HD schedule, as well as one follow-up visit. Subjects will received up to two treatments of study drug. After providing written informed consent (and children's informed assent, as applicable), subjects will be screened for eligibility based on the inclusion and exclusion criteria at a screening visit. The screening visit and Visit 1 may be combined at the discretion of the investigator. At Visit 1, eligible subjects, with a BFR that is <300 mL/min and at least 25 mL/min below the prescribed BFR at an arterial pressure of −250 mmHg (or at institutional guidelines for maximum negative arterial pressure, not to exceed 250 mmHg) at the beginning of HD (within the first 30 minutes), will be randomly assigned in a 1:1 ratio to receive either tenecteplase or placebo. The BFR measurement obtained at Visit 1 to determine study eligibility will be considered the baseline BFR. Subjects will have 2 mL of study drug (i.e., 2 mg of tenecteplase, or placebo equivalent) instilled into each of the two lumens of the HD catheter. After a dwell time of 1 hour, the study drug will be withdrawn, and all subjects will undergo HD as prescribed or to the extent possible. BFR will be measured at the beginning of HD, every 30 minutes thereafter, 30 minutes before the end of HD, and at the end of HD to assess catheter function and determine treatment outcome for Visit 1.

Subjects with a BFR of <300 mL/min at the beginning of Visit 2 will be treated with 2 mL (2 mg) of open-label tenecteplase (regardless of treatment outcome at Visit 1). After a dwell time of 1 hour, the study drug will be withdrawn and subjects will undergo HD as prescribed or to the extent possible. BFR will be measured at the beginning of HD, every 30 minutes thereafter, 30 minutes before the end of HD, and at the end of HD to assess catheter function and determine treatment outcome for Visit 2.

Follow-up assessments of HD catheter function will be performed by measuring BFR at the beginning of HD (within the first 30 minutes) at each of the two visits that follow final study drug exposure (i.e., Visits 2 and 3 for subjects who receive one treatment of study drug and Visits 3 and 4 for subjects who receive two treatments of study drug). For these assessments, study personnel will increase the BFR in an effort to achieve the prescribed BFR within the first 30 minutes.

If at any time the HD catheter is removed for any reason, no further treatments will be given and no additional efficacy assessments (i.e., BFR measurements or blood urea nitrogen [BUN] analysis) will be performed. However, subjects will continue to undergo safety assessments (i.e., recording of adverse events and concomitant medications and antibody testing). Subjects with symptomatic hypotension may not receive study drug.

Adverse events will be recorded for all subjects from treatment initiation through completion of the second visit following final study drug exposure (i.e., Visit 3 for subjects who receive one treatment of study drug and Visit 4 for subjects who receive two treatments of study drug). All subjects will undergo antibody testing 30-36 days after Visit 1 or upon early termination from the study.

Efficacy Outcome Measures

Treatment success for this study will be defined as follows:
BFR of ≥300 mL/min and an increase from baseline BFR of ≥25 mL/min (without reversal of lines) at an arterial pressure in the range of 0 to −250 mmHg, at the end of HD and 30 (±10) minutes prior to the end of HD. Subjects with a BFR of ≥300 mL/min and an increase from baseline BFR of <25 mL/min, subjects with a BFR of <300 mL/min, and subjects for whom the catheter lines are reversed will be considered to have had treatment failure.

If an investigator determines that a subject has become hemodynamically unstable (decrease in blood pressure or change in heart rate) and requires his or her BFR to be decreased as a result, a BFR measurement must be recorded prior to decreasing the BFR. The BFR over the 30 minutes prior to development of hemodynamic instability will be used to determine treatment outcome.

For subjects who have treatment success at Visits 1 or 2, maintenance of catheter function at subsequent visits is defined as a BFR of ≥300 mL/min and an increase from baseline BFR of ≥25 mL/min (without reversal of lines) at an arterial pressure in the range of 0 to −250 mmHg at the beginning of that HD session (within the first 30 minutes). For these assessments, study personnel will increase the BFR in an effort to achieve the prescribed BFR within the first 30 minutes.

The primary efficacy outcome measure is as follows:
Percentage of subjects who have treatment success with respect to BFR at Visit 1 (as defined above).

The secondary efficacy outcome measures are as follows:
For subjects who have treatment success at Visit 1, the percentage of subjects who maintain catheter function at Visits 2 and 3 (as defined above)

Percentage of subjects with a urea reduction ratio (URR) of ≥65% as assessed by pretreatment and post-HD BUN measurements at Visit 1

For subjects who do not receive open-label tenecteplase at Visit 2, the percentage of subjects with a URR of ≥65% as assessed by pre- and post-HD BUN measurements at Visit 2

Change in BFR from baseline to the end of HD at Visit 1

Percentage of subjects who fall into each of the following categories defined by change in BFR from baseline to the end of HD at Visit 1: <0 mL/min, 0-24 mL/min, 25-49 mL/min, 50-99 mL/min, 100-149 mL/min, and ≥150 mL/min For subjects treated with open-label tenecteplase at Visit 2, secondary efficacy outcome measures also include the following:

Percentage of subjects who have treatment success with respect to BFR at Visit 2 (as defined above)

For subjects who have treatment success at Visit 2, the percentage of subjects who maintain catheter function at Visits 3 and 4 (as defined above)

Change in BFR from baseline to the end of HD at Visit 2

Percentage of subjects with a URR of ≥65% as assessed by pre- and post-HD BUN measurements at Visit 2

Percentage of subjects with a URR of ≥65% as assessed by pre- and post-HD BUN measurements at Visit 3

Percentage of subjects who fall into each of the following categories defined by change in BFR from baseline to the end of HD at Visit 2: <0 mL/min, 0-24 mL/min, 25-49 mL/min, 50-99 mL/min, 100-149 mL/min, and ≥150 mL/min Safety Outcome Measures The primary safety outcome measure is as follows:
Incidence of targeted adverse events (intracranial hemorrhages, major bleeding, embolic events, thrombosis, catheter-related blood stream infections, and catheter-related complications) from initial study drug administration through the start of Visit 2

The secondary safety outcome measures are as follows:
For subjects who do not receive tenecteplase at Visit 2, the incidence of targeted adverse events (as listed above) from the start of Visit 2 through the completion of Visit 3

For subjects who do receive tenecteplase at Visit 2, the incidence of targeted adverse events (as listed above) from the start of Visit 2 through the completion of Visit 4

Incidence of serious adverse events and incidence of all adverse events from initial study drug administration through the start of Visit 2

For subjects who do not receive tenecteplase at Visit 2, the incidence of serious adverse events and the incidence of all adverse events from the start of Visit 2 through the completion of Visit 3

For subjects who do receive tenecteplase at Visit 2, the incidence of serious adverse events and the incidence of all adverse events from the start of Visit 2 through the completion of Visit 4

Incidence of positive anti-tenecteplase antibody tests in subjects who tested negative at baseline Safety Plan Tenecteplase is approved for use in the reduction of mortality associated with acute myocardial infarction (AMI). The adverse events associated with systemic use of tenecteplase at doses of 30-50 mg for treatment of AMI are well described and consist primarily of bleeding complications, including major bleeding events and intracranial hemorrhages. Another adverse event that could be associated with use of thrombolytics for treatment of dysfunctional catheters thrombolysis is embolization of a catheter-related thrombus. Based on the clinical experience with tenecteplase for treatment of AMI and CATHFLO® ACTIVASE® (alteplase) for treatment of dysfunctional CVA catheters, it is anticipated that any potential bleeding or embolic events attributable to tenecteplase are most likely to occur within 24 hours of treatment. All adverse events will be recorded from initiation of study treatment through completion of the second visit following final study drug exposure.

Study Treatment

Subjects will receive up to two treatments of study drug, depending on restoration of HD catheter function, as described above (see "Study Design"). The first treatment, either tenecteplase or placebo, will be given to all subjects at Visit 1, and the second treatment, open-label tenecteplase, will be given to eligible subjects at Visit 2. At each administration, subjects will have 2 mL of study drug (i.e., 2 mg of tenecteplase, or placebo equivalent) instilled into each lumen of their HD catheter.

Concomitant Therapy and Clinical Practice

The use of fibrinolytic agents (other than study drug), warfarin (except for low-dose warfarin used for prophylaxis), and unfractionated or low molecular weight heparin (except for heparin used only during HD or for prophylaxis) is prohibited from Visit 1 through completion of the second visit following final study drug exposure. Subjects who are taking Plavix® (clopidogrel bisulfate) may not increase their dose from Visit 1 through completion of the second visit following final study drug exposure. Subjects may continue to receive other medications and standard treatments administered for their conditions at the discretion of the treating physician.

The use of fibrinolytic agents (other than study drug) is prohibited during the course of the study (through completion of the second visit following final study drug exposure), but subjects may continue to receive medications and standard treatments administered for their conditions at the discretion of the treating physician.

Statistical Methods

Primary Efficacy Analysis

The percentage of subjects who achieve treatment success will be computed, and 95% confidence intervals based on exact method will be provided. This percentage will be compared between treatment arms using a Cochran-Mantel-Haenszel test (stratified by baseline BFR: 0-199 mL/min, 200-274 mL/min, and 275-299 mL/min).

Missing Data

For the purpose of analysis, subjects who discontinue from the study for any reason without having achieved treatment success (as defined above) will be considered to have had treatment failure.

Determination of Sample Size

A sample size of 150 subjects will give >90% power to detect a tenecteplase response rate of 25% against a placebo response rate of 5% utilizing a two-sided $\chi^2$ test at the 0.05 level of significance.

Interim Analysis

A Data Monitoring Committee (DMC) will perform periodic reviews of accumulating safety data during the study.

Detailed Study Design

This is a Phase III, randomized, double-blind, placebo-controlled study that will be conducted at multiple centers. Approximately 150 subjects, ≥16 years of age, who require HD and have dysfunctional HD catheters will be enrolled in the study. Subjects will be classified by baseline BFR into three strata: 0-199 mL/min, 200-274 mL/min, and 275-299 mL/min. Enrollment in the 0-199 mL/min and 275-299 mL/min strata will be limited to a maximum of 10% of subjects in each.

The study will consist of three to four visits for each subject that correspond to consecutive HD sessions based on each subject's regular HD schedule, as well as one follow-up visit. Subjects will receive up to two treatments of study drug. The first treatment, either tenecteplase or placebo, will be given to all subjects at Visit 1, and the second treatment, open-label tenecteplase, will be given to eligible subjects at Visit 2.

After providing written informed consent (and children's informed assent, as applicable), subjects will be screened for eligibility based on the inclusion and exclusion criteria at a screening visit. The screening visit and Visit 1 may be combined at the discretion of the investigator. At Visit 1, eligible subjects, with a BFR that is <300 mL/min and at least 25 mL/min below the prescribed BFR at an arterial pressure of −250 mmHg (or at institutional guidelines for maximum negative arterial pressure, not to exceed 250 mmHg) at the beginning of HD (within the first 30 minutes), will be randomly assigned in a 1:1 ratio to receive either tenecteplase or placebo. The BFR measurement obtained at Visit 1 to determine study eligibility will be considered the baseline BFR. Subjects will have 2 mL of study drug (i.e., 2 mg of tenecteplase, or placebo equivalent) instilled into each of the two lumens of the HD catheter. After a dwell time of 1 hour, the study drug will be withdrawn, and all subjects will undergo HD as prescribed or to the extent possible. BFR will be measured at the beginning of HD, every 30 minutes thereafter, 30 minutes before the end of HD, and at the end of HD to assess catheter function and determine treatment outcome for Visit 1 (as defined above).

Subjects with a BFR of <300 mL/min at the beginning of Visit 2 will be treated with 2 mL (2 mg) of open-label tenecteplase (regardless of treatment outcome at Visit 1). After a dwell time of 1 hour, the study drug will be withdrawn and subjects will undergo HD as prescribed or to the extent possible. BFR will be measured at the beginning of HD, every 30 minutes thereafter, 30 minutes before the end of HD, and at the end of HD to assess catheter function and determine treatment outcome for Visit 2.

Follow-up assessments of HD catheter function will be performed by measuring BFR at the beginning of HD (within the first 30 minutes) at each of the two visits that follow final study drug exposure (i.e., Visits 2 and 3 for subjects who receive one treatment of study drug and Visits 3 and 4 for subjects who receive two treatments of study drug). For these assessments, study personnel will increase the BFR in an effort to achieve the prescribed BFR within the first 30 minutes.

If at any time the HD catheter is removed for any reason, no further treatments will be given and no additional efficacy assessments (i.e., BFR measurements or blood urea nitrogen [BUN] analysis) will be performed. However, subjects will continue to undergo safety assessments (i.e., recording of adverse events and concomitant medications and antibody testing). Subjects with symptomatic hypotension may not receive study drug.

Adverse events will be recorded for all subjects from treatment initiation through completion of the second visit following final study drug exposure (i.e., Visit 3 for subjects who receive one treatment of study drug and Visit 4 for subjects who receive two treatments of study drug). All subjects will undergo antibody testing 30-36 days after Visit 1 or upon early termination from the study.

This double-blind, placebo-controlled clinical trial is designed to assess the efficacy and safety of tenecteplase versus placebo for restoration of function to dysfunctional HD catheters, and is based, at least in part, on the approved dose of CATHFLO®ACTIVASE® (alteplase) and experience with alteplase in CVA and HD catheters.

CATHFLO®ACTIVASE> (alteplase) is currently approved for treatment of dysfunctional CVA devices. In clinical trials, up to two 2-mg doses of alteplase (with smaller doses for subjects weighing <30 kg), each followed by a dwell time of 120 minutes, were effective and safe in restoring function to dysfunctional CVA devices.

Initial studies performed by Refino et al., *Thromb Haemost* 69(6):841 (1993)) using human plasma demonstrated that tenecteplase had equivalent relative potency to tPA (alteplase). In addition, Keyt et al. *Proc Natl Acad Sci. USA* 91:3670-4 (1994)) demonstrated that tenecteplase was 82% as active as wild-type tPA with respect to plasma clot lysis in an in vitro system. These results suggest that tenecteplase may be 82%-100% as active as alteplase in its ability to lysis clots; therefore, the dose of tenecteplase in the current study is 2 mg (2 mL) for each lumen, with withdrawal after a one-hour dwell time. Of note, the 2-mg dose is 15-25 times lower than the approved systemic dose of tenecteplase for treatment of AMI.

There will be no systemic administration in this study. However, in cases where the catheter lumen size is unknown or smaller than the specified dose of tenecteplase in this study (2 mL), the possibility exists for a portion of the administered dose (i.e., the difference between 2 mL and the catheter lumen volume) to enter the systemic circulation. This dosing regimen is not significantly different from the dosing regimen in the Cathflo Activase clinical trials (A2055g, A2065g, and A2404g), in which pediatric subjects weighing <30 kg were administered a dose equivalent to 110% of the catheter lumen volume. In a scenario in which the entire 2-mg dose was inadvertently given as an intravenous bolus, this would result in an expected maximum plasma concentration of 0.25 µg/mL. To put this in perspective, the maximum predicted concentration for 2 mg of alteplase is 0.58 µg/mL. In comparison, the 30-mg dose of tenecteplase commonly used in AMI would result in maximum plasma concentrations in the range of 5.9 to 7.5 µg/mL (mean data from the TIMI 10A and 10B trials) (Cannon et al. 1997, 1998). Similarly, patients given 100 mg of alteplase via the accelerated infusion regimen were predicted by Tanswell et al. (1992) to achieve a maximum concentration of approximately 4 µg/mL. In comparison, the level of endogenously produced tissue plasminogen activator has been reported to be in the range of 0.002 to 0.021 µg/mL.

The rationale for limiting enrollment to subjects with a BFR of <300 mL/min at an arterial pressure of −250 mmHg is based on recommendations in the KDOQI guidelines on vascular access for HD, which suggest that a BFR of ≥300 mL/min is needed to provide adequate dialysis without lengthening the time of HD prohibitively. Since the BFR is directly related to the negative arterial pressure, an arterial pressure in the range of 0 to −250 mmHg was set for this study to maintain consistent conditions for the BFR determinations. In addition, KDOQI guidelines suggest measuring BFR at an arterial pressure of −250 mmHg to determine catheter dysfunction.

Efficacy Outcome Measures

The primary efficacy outcome measure is as follows:
Percentage of subjects who have treatment success with respect to BFR at Visit 1 (as defined above).

The secondary efficacy outcome measures are as follows:
For subjects who have treatment success at Visit 1, the percentage of subjects who maintain catheter function at Visits 2 and 3 (as defined above)
Percentage of subjects with a urea reduction ratio (URR) of ≥65% as assessed by pretreatment and post-HD BUN measurements at Visit 1
For subjects who do not receive open-label tenecteplase at Visit 2, the percentage of subjects with a URR of ≥65% as assessed by pre- and post-HD BUN measurements at Visit 2
Change in BFR from baseline to the end of HD at Visit 1
Percentage of subjects who fall into each of the following categories defined by change in BFR from baseline to the end of HD at Visit 1: <0 mL/min, 0-24 mL/min, 25-49 mL/min, 50-99 mL/min, 100-149 mL/min, and ≥150 mL/min For subjects treated with open-label tenecteplase at Visit 2, secondary efficacy outcome measures also include the following:
Percentage of subjects who have treatment success with respect to BFR at Visit 2 (as defined above)
For subjects who have treatment success at Visit 2, the percentage of subjects who maintain catheter function at Visits 3 and 4 (as defined above)
Change in BFR from baseline to the end of HD at Visit 2
Percentage of subjects with a URR of ≥65% as assessed by pre- and post-HD BUN measurements at Visit 2
Percentage of subjects with a URR of ≥65% as assessed by pre- and post-HD BUN measurements at Visit 3
Percentage of subjects who fall into each of the following categories defined by change in BFR from baseline to the end of HD at Visit 2: <0 mL/min, 0-24 mL/min, 25-49 mL/min, 50-99 mL/min, 100-149 mL/min, and ≥150 mL/min Safety Outcome Measures The primary safety outcome measure is as follows:
Incidence of targeted adverse events (ICHs, major bleeding, embolic events, thrombosis, catheter-related bloodstream infections [CRBSIs], and catheter-related complications) from initial study drug administration through the start of Visit 2

The secondary safety outcome measures are as follows:
For subjects who do not receive tenecteplase at Visit 2, the incidence of targeted adverse events (as listed above) from the start of Visit 2 through the completion of Visit 3
For subjects who do receive tenecteplase at Visit 2, the incidence of targeted adverse events (as listed above) from the start of Visit 2 through the completion of Visit 4
Incidence of serious adverse events and incidence of all adverse events from initial study drug administration through the start of Visit 2
For subjects who do not receive tenecteplase at Visit 2, the incidence of serious adverse events and the incidence of all adverse events from the start of Visit 2 through the completion of Visit 3
For subjects who do receive tenecteplase at Visit 2, the incidence of serious adverse events and the incidence of all adverse events from the start of Visit 2 through the completion of Visit 4
Incidence of positive anti-tenecteplase antibody tests in subjects who tested negative at baseline Safety Plan Tenecteplase is approved for use in the reduction of mortality associated with AMI. The adverse events associated with systemic use of tenecteplase at doses of 30-50 mg for treatment of AMI are well described and consist primarily of bleeding complications, including major bleeding events and ICHs. The elimination of tenecteplase from the plasma is biphasic, with a mean initial half-life of 20-24 minutes and a mean terminal half-life of 90-130 minutes (Modi et al. Journal of Clinical Pharmacology, 40: 508-515 (2000). Although the incidence of bleeding complications in subjects with AMI treated with tenecteplase has been quantified, data on the incidence of bleeding complications associated with the lower doses of tenecteplase used in this study are limited. The incidence of ICH and major bleeding attributed to tenecteplase is anticipated to be relatively low in this study because of the low proposed dose, minimal systemic exposure to tenecteplase, and the clinical trial experience to date with CATHFLO®ACTIVASE® (alteplase), which indicates that no ICHs have been reported and only 3 of 1432 subjects have experienced major bleeding.

Another adverse event that could be associated with use of thrombolytics for treatment of dysfunction catheters is embolization of a catheter-related thrombus. Such an event could result in a pulmonary embolus, which could be life-threatening, depending on the size of the pulmonary embolus. The incidence of clinically significant embolic events associated with the use of tenecteplase for catheter clearance is expected to be low based on the extensive experience with both urokinase and CATHFLO®ACTIVASE® (alteplase) in CVA catheters.

Based on the clinical experience with tenecteplase for treatment of AMI and Cathflo Activase for treatment of dysfunctional CVA catheters, it is anticipated that any potential bleeding or embolic events attributable to tenecteplase are most likely to occur within 24 hours of treatment.

All adverse events will be recorded from initiation of study treatment through completion of the second visit following final study drug exposure. All serious adverse events will be reported to Genentech within 48 hours, regardless of causality or treatment pathway.

A DMC will review cumulative safety data for the tenecteplase catheter-clearance program, at predetermined intervals and will be responsible for making recommendations to the sponsor regarding the continuing safety of the study, based on the results of this data review process.

Subjects with dysfunctional HD catheters are eligible for this study and will be screened using criteria provided herein. Subjects who are randomized to receive placebo will serve as the comparison group in evaluating the efficacy and safety of a single intra-luminal instillation of tenecteplase in the restoration of function to dysfunctional HD catheters. The study will be conducted as a randomized, double-blind, and placebo-controlled clinical trial to minimize any bias.

This study will be conducted according to the U.S. FDA, the International Conference on Harmonisation E6 Guideline for Good Clinical Practice (GCP), and any national requirements.

Materials and Methods
Subject Selection

Subjects with a dysfunctional HD catheter, based on BFR during the first 30 minutes of HD (as defined above), are eligible for this study. Approximately 150 subjects at multiple study sites will be enrolled. Subjects will be screened using the inclusion and exclusion criteria listed below.

Inclusion Criteria

Subjects must meet all of the following criteria to be eligible for inclusion in the study:

Able to provide written informed consent and comply with the study assessments for the full duration of the study Age ≥16 years Clinically stable, in the opinion of the investigator Use of a cuffed tunneled HD catheter with a BFR of <300 mL/min at a maximum negative arterial pressure of 250 mmHg, but with a demonstrated BFR of ≥300 mL/min in at least one HD session in the 7 days prior to Visit 1

HD prescribed at a BFR of ≥300 mL/min

Baseline BFR (during the first 30 minutes of HD) of <300 mL/min (using catheter lines in the customary direction, prior to any reversal of lines; see Section 3.1.2.a) at an arterial pressure of −250 mmHg (or at institutional guidelines for maximum negative arterial pressure, not to exceed 250 mmHg)

Baseline BFR (during the first 30 minutes of HD) at least 25 mL/min below the prescribed BFR For example, subjects with HD prescribed at a BFR of 300 mL/min must have a BFR of ≤275 mL/min to enter the study.

Demonstrated BFR of ≥300 mL/min (using catheter lines in the customary direction) at an arterial pressure in the range of 0 to −250 mmHg in at least one HD session in the 7 days prior to Visit 1

Anticipated use of the same catheter for at least four consecutive HD sessions, on the same type and model of HD apparatus Able to have fluids infused at the volume necessary to instill study drug into the HD catheter (see Dosage, Administration and Storage section below)

Exclusion Criteria

Subjects who meet any of the following criteria will be excluded from the study:

HD catheter with sustainable BFR of ≥300 mL/min following subject repositioning

HD catheter inserted <2 days prior to screening

Evidence of a mechanical, non-thrombotic cause of HD catheter dysfunction (e.g., kink in the catheter or suture constricting the catheter), or dysfunction caused by known fibrin sheath Use of an implantable port HD catheter implanted in the subclavian vein Anticipated use of catheter for any other type of diagnostic or therapeutic procedure (i.e., other than HD) during the course of the study Previously treated in this study or any tenecteplase catheter clearance trial Use of any investigational drug or therapy within 28 days prior to screening Use of a fibrinolytic agent (e.g., alteplase, tenecteplase, reteplase, or urokinase) within 7 days prior to Visit 1

Known to be pregnant or breastfeeding at screening

HD catheter with known or suspected infection

History of any intracranial hemorrhage, aneurysm, or arteriovenous malformation

Use of any heparin (unfractionated or low molecular weight) within 24 hours prior to Visit 1, except for heparin used only during HD or for prophylaxis (e.g., heparin lock)

Use of warfarin within 7 days prior to Visit 1, except for low-dose warfarin used for prophylaxis Initiation of or increase in dose of Plavix® (clopidogrel bisulfate) within 7 days prior to Visit 1

Hemoglobin ≥13.5 g/dL if on erythropoietin

A laboratory test to confirm hemoglobin levels must have been performed within 30 days prior to screening.

Platelet count <75,000/μL
  A laboratory test to confirm platelet count must have been performed within 30 days prior to screening.
At high risk for bleeding events or embolic complications (i.e., recent pulmonary embolus, deep vein thrombosis, endarterectomy, or clinically significant right-to-left shunt) in the opinion of the investigator, or with known condition for which bleeding constitutes a significant hazard
BFR of <300 mL/min because of symptomatic hypotension
Uncontrolled hypertension in the opinion of the investigator (e.g., systolic pressure >185 mmHg and diastolic pressure >110 mmHg)
Known hypersensitivity to tenecteplase or any component of the formulation Method of Treatment Assignment and Blinding This is a double-blind, placebo-controlled study. Subjects will be classified by baseline BFR into three strata: 0-199 mL/min, 200-274 mL/min, and 275-299 mL/min. Enrollment in the 0-199 mL/min and 275-299 mL/min strata will be limited to a maximum 10% of subjects in each. Within each stratum, subjects will be randomized to the tenecteplase group or placebo group in a 1:1 ratio using a hierarchical, dynamic algorithm, implemented through an interactive voice response system (IVRS).

Formulation

Both tenecteplase and placebo are supplied in single-use, 6-cc glass vials with DAIKYO™ stoppers and flip-off aluminum caps. Tenecteplase is provided as a sterile, lyophilized formulation containing 2 mg of protein, with specifications for the following excipients: 104.4 mg of L-arginine, 32 mg of phosphoric acid, and 0.8 mg of polysorbate 20. Placebo is provided as a sterile, lyophilized formulation that has the same excipients as tenecteplase without the active ingredient. Diluent is Sterile Water for Injection, USP/EP (SWFI).

Dosage, Administration, and Storage

Subjects will receive up to two treatments of study drug, depending on restoration of HD catheter function, as described in Section 3.1. At each treatment, subjects will have 2 mL of study drug (i.e., 2 mg of tenecteplase, or placebo equivalent) instilled into each lumen of their HD catheter. If at any time the HD catheter is removed for any reason, no further treatments will be given. Subjects with symptomatic hypotension may not receive study drug.

Reconstitute each vial of lyophilized tenecteplase or placebo immediately before use with 2.2 mL of SWFI. Direct the flow of SWFI directly into the lyophilized cake of study drug using aseptic technique, and gently swirl the vial until the contents are dissolved. Do not shake. The concentration of tenecteplase in the resulting solution will be 1 mg/mL. Slight foaming upon reconstitution is not unusual; any large bubbles will dissipate if the vial is allowed to stand undisturbed for several minutes. If the reconstituted study drug is not used immediately, the solution must be stored at 2° C.-8° C. (36° F.-46° F.) and used within 8 hours of reconstitution. Discard any unused solution.

Just prior to administering study drug, withdraw any fluid in the HD catheter lumen and attempt to flush with saline. To administer the dose, 2 mL of reconstituted study drug should be drawn into a single 10-mL syringe using aseptic technique. The solution should then be instilled into one HD catheter lumen according to the institution's guidelines. The remaining volume of the catheter should be backfilled with normal saline. Repeat for the second lumen.

Store vials of study drug under refrigeration at 2° C.-8° C. (36° F.-46° F.). Do not store the unused portion of any vial for future use. Do not use study drug beyond the expiration date on the vial or expiration extension documentation provided by Genentech. Partially used vials, empty vials, and unreconstituted vials will be returned to Genentech.

Dosage Modification

No dose modifications are allowed.

Concomitant and Excluded Therapies

Subjects will not be allowed to receive any intravenous therapy or provide blood samples through the HD catheter while study drug is in the catheter. Intravenous therapy or procurement of blood samples is acceptable only through use of a separate route. The use of fibrinolytic agents (other than study drug), warfarin (except for low-dose warfarin used for prophylaxis), and unfractionated or low molecular weight heparin (except for heparin used only during HD or for prophylaxis) is prohibited from Visit 1 through completion of the second visit following final study drug exposure (i.e., Visit 3 for subjects who receive one treatment of study drug and Visit 4 for subjects who receive two treatments of study drug). Subjects who are taking clopidogrel bisulfate may not increase their dose from Visit 1 through completion of the second visit following final study drug exposure. Subjects may continue to receive other medications and standard treatments administered for their conditions at the discretion of the treating physician.

Study Assessments

The study will consist of visits that correspond to consecutive HD sessions for each subject, as well as one follow-up visit. The screening visit and Visit 1 may be combined at the discretion of the investigator. Subjects will receive up to two treatments of study drug. The first treatment, either tenecteplase or placebo, will be given to all subjects at Visit 1, and the second treatment, open-label tenecteplase, will be given to eligible subjects at Visit 2. Subjects who receive one treatment of study drug will undergo follow-up assessments of HD catheter function at Visits 2 and 3. Subjects who receive two treatments of study drug will undergo follow-up assessments of HD catheter function at Visits 3 and 4. All subjects will return for a follow-up visit 30 (up to 36) days after Visit 1 or upon early termination from the study.

If at any time the HD catheter is removed for any reason, no further treatments will be given and no additional efficacy assessments (i.e., BFR measurements or BUN analysis) will be performed. However, subjects will continue to undergo safety assessments (i.e., recording of adverse events and concomitant medications and antibody testing).

Laboratory kits and instructions for collection of BUN and anti-tenecteplase antibody samples will be provided by a central laboratory, Quintiles Laboratories (QLab). All samples will be processed at the site and shipped to QLab. QLab will perform BUN analysis, calculate URR, and ship the antibody samples to Genentech for testing.

Screening Visit

Any or all of the screening assessments may be performed at Visit 1 (before randomization) at the discretion of the investigator. Written informed consent/assent MUST be obtained before any study-specific assessments or procedures are performed.

The following screening assessments and procedures will be performed:
  Written informed consent/assent
  Review of inclusion and exclusion criteria
  Demographic data, including the subject's birth date, sex, and race/ethnicity
  Physical examination and medical history, including the two most recent URR values (historical baseline)

If a physical examination is not medically indicated at the screening visit, a historical physical examination may be used, as long as it was performed within 7 days prior to screening.

Vital signs, including blood pressure, respiratory rate, temperature, and pulse (specify if pre- or post-HD)

Weight (specify if pre- or post-HD)

Blood sample to determine hemoglobin level (if subject is on erythropoietin) and platelet count, if laboratory tests confirming eligibility were not performed within 30 days prior to screening Concomitant medications HD catheter history and information Information on the date of HD catheter insertion and the date the HD catheter was last known to have function (BFR of ≥300 mL/min) will be recorded. HD catheter lumen size, type, volume, brand (if known), and placement location will also be recorded.

HD prescription

Visit 1

Visit 1 must be performed within 7 days after screening (as stated above, the screening visit and Visit 1 may be combined at the discretion of the investigator). At the beginning of Visit 1, the following should be performed to verify eligibility:

Review of inclusion and exclusion criteria

Review of concomitant medication and medical history (to ensure no changes since screening), including use of fibrinolytics, warfarin, and clopidogrel bisulfate within 7 days prior to Visit 1 and use of heparin within 24 hours prior to Visit 1 (see Section 4.1.3)

HD prescription

HD, initiated as prescribed

Baseline BFR, measured at the beginning of HD (within the first 30 minutes) to confirm HD catheter dysfunction Subjects with a BFR that is <300 mL/min and at least 25 mL/min below the prescribed BFR (using catheter lines in the customary direction) at an arterial pressure of −250 mmHg (or at institutional guidelines for maximum negative arterial pressure, not to exceed 250 mmHg) are eligible for the study; all other subjects are ineligible. Baseline BFR will be recorded at the time it is first determined that a subject is eligible for the study (i.e., when arterial pressure reaches −250 mmHg).

If an attempt has been made to dialyze with the lines reversed (i.e., before opting for study drug treatment), BFR must be recorded prior to line reversal and will be used as the baseline value.

Subjects whose BFR cannot be measured because of total occlusion (i.e., no blood withdrawal function) should be considered to have a baseline BFR of 0 mL/min.

Eligible subjects will have their HD interrupted. Ineligible subjects may complete their prescribed HD session and should be registered as having failed screening.

Once eligibility has been verified, the subject will be randomized and assigned a blinded study drug kit using the IVRS. The following assessments and procedures will also be performed at Visit 1:

Blood sample for serum anti-tenecteplase antibody testing, collected prior to treatment with study drug Blood sample for BUN analysis, collected prior to treatment with study drug Blinded study drug administration, prior to resuming HD Study drug will be administered as described in Section 4.3.2 and will be left to dwell, undisturbed, in the subject's HD catheter (both lumens) for 1 hour. After the 1-hour dwell, study drug will be withdrawn.

Subjects with symptomatic hypotension may not receive study drug.

HD, resumed and performed as prescribed or to the extent possible

BFR, measured at the beginning of HD, every 30 minutes thereafter, 30 minutes before the end of HD, and at the end of HD to determine treatment outcome (as defined in Section 3.1.2.b)

If it becomes necessary to dialyze with the catheter lines reversed, a BFR measurement will be recorded prior to reversal and no additional BFR measurements will be recorded during this HD session.

If an investigator determines that a subject requires his or her BFR to be decreased because of hemodynamic instability, a BFR measurement will be recorded prior to decreasing the BFR. Subsequent BFRs will continue to be recorded as scheduled.

Blood sample for BUN analysis, collected upon completion of HD

If the catheter lines have been reversed, no blood sample will be taken.

Adverse events and changes in concomitant medications during this visit

Monitoring of adverse events will begin upon initiation of study treatment.

Visit 2

The following assessments and procedures will be performed at Visit 2:

Adverse events and changes in concomitant medications since the last visit

HD prescription

Blood sample for BUN analysis, collected prior to HD

HD, initiated as prescribed

BFR, measured at the beginning of HD (within the first 30 minutes) to assess HD catheter function For these assessments, study personnel will increase the BFR in an effort to achieve the prescribed BFR within the first 30 minutes.

Subjects with a BFR of ≥300 mL/min at the beginning of HD will complete their prescribed HD session. Subjects with a BFR of <300 mL/min will have their HD interrupted and the following assessments and procedures performed:

Open-label tenecteplase administration

Tenecteplase will be administered as described in Section 4.3.2 and will be left to dwell, undisturbed, in the subject's HD catheter (both lumens) for 1 hour. After the 1-hour dwell, tenecteplase will be withdrawn.

Subjects with symptomatic hypotension may not receive study drug.

HD, resumed and performed as prescribed or to the extent possible

BFR, measured at the beginning of HD, every 30 minutes thereafter, 30 minutes before the end of HD, and at the end of HD to determine treatment outcome (as defined in Section 3.1.2.b)

If it becomes necessary to dialyze with the catheter lines reversed, a BFR measurement will be recorded prior to reversal and no additional BFR measurements will be recorded during this HD session.

If an investigator determines that a subject requires his or her BFR to be decreased because of hemodynamic instability, a BFR measurement will be recorded prior to decreasing the BFR. Subsequent BFRs will continue to be recorded as scheduled.

All subjects (regardless of whether they received open-label tenecteplase) will have the following assessments and procedures performed upon completion of HD:
  Blood sample for BUN analysis
    If the catheter lines have been reversed, no blood sample will be taken.
  Adverse events and changes in concomitant medications during this visit
Visit 3
The following assessments and procedures will be performed at Visit 3:
  Adverse events and changes in concomitant medications since the last visit
  HD prescription
  For subjects who received open-label tenecteplase at Visit 2 only: Blood sample for BUN analysis, collected prior to HD
  HD, performed as prescribed or to the extent possible
  BFR, measured at the beginning of HD (within the first 30 minutes) to assess HD catheter function
    For these assessments, study personnel will increase the BFR in an effort to achieve the prescribed BFR within the first 30 minutes.
  For subjects who received open-label tenecteplase at Visit 2 only: Blood sample for BUN analysis, collected upon completion of HD
    If the catheter lines have been reversed, no blood sample will be taken.
  Adverse events and changes in concomitant medications during this visit
Visit 4
Visit 4 is required only for subjects who received open-label tenecteplase at Visit 2. Those subjects will have the following study assessments and procedures performed:
  Adverse events and changes in concomitant medications since the last visit
  For subjects who had treatment success at Visit 2 only: BFR, measured at the beginning of HD (within the first 30 minutes) to assess HD catheter function
  HD prescription
  HD, performed as prescribed or to the e extent possible
  BFR, measured at the beginning of HD (within the first 30 minutes) to assess HD catheter function. For these assessments, study personnel will increased the BFR in an effort to achieve the prescribed CFR changes within the first 30 minutes.
  Adverse events and changes in concomitant medications during this visit
Follow-Up at 30 Days/Early Termination
All subjects will have blood drawn for anti-tenecteplase antibody testing at 30 days (up to 36 days) after Visit 1 or upon early termination from the study. Information on catheter status will also be collected at this visit. Adverse events will be recorded at early termination if this occurs prior to the second visit following the last administration of study treatment.
Subject Discontinuation
Subjects have the right to withdraw from the study at any time.
The investigator has the right to withdraw a subject for any reason that is in the best interest of the subject, including intercurrent illness, adverse events, or worsening condition. Genentech reserves the right to request withdrawal of a subject because of a protocol violation, administrative reasons, a decision to limit or terminate the study for any reason, or any other valid and ethical reason.

Study Discontinuation
Genentech has the right to terminate this study at any time. Reasons for terminating the study may include, but are not limited to, the following:
  The incidence or severity of adverse events in this or other studies indicates a potential health hazard to subjects.
  Subject enrollment is unsatisfactory.
  Data recording is inaccurate or incomplete.
Statistical Methods
All subjects randomized and treated with study drug will be included in the efficacy and safety analyses. Efficacy analyses will be based on a subject's assigned treatment, while safety analyses will be based on a subject's actual treatment received. All hypothesis tests will be conducted at the 0.05 level of significance with no adjustment for multiple endpoints. Full details of the statistical analysis methods will be included in the Statistical Analysis Plan.
Analysis of the Conduct of the Study
Enrollment, number of tenecteplase administrations, major protocol violations, discontinuations from the study, and reasons for discontinuation will be summarized by treatment arm. Subject disposition will be tabulated by treatment group at each study visit.
Analysis of Treatment Group Comparability
Demographics and baseline characteristics, such as age, sex, race, weight, catheter type, and baseline BFR, will be summarized by treatment arm using means and standard deviations or medians and ranges for continuous variables, and proportions for categorical variables. Statistical testing for significant differences between treatment arms will not be performed.
Efficacy Analyses
a. Primary Efficacy Outcome Measure
The primary efficacy outcome measure is the percentage of subjects who have treatment success with respect to BFR at Visit 1 (as defined earlier). Subjects who discontinue from the study before completing HD, or are otherwise not evaluable for the primary outcome measure, will be considered to have had treatment failure with respect to the primary outcome measure. The percentage of subjects who achieve treatment success will be computed, and 95% confidence intervals based on exact method will be provided. This percentage will be compared between treatment arms using a Cochran-Mantel-Haenszel test (stratified by baseline BFR: 0-199 mL/min, 200-274 mL/min, and 275-299 mL/min). Sensitivity analyses will be conducted to evaluate robustness of the primary results to alternative missing data methods, including complete case analysis and last observation carried forward (LOCF) imputation.
b. Secondary Efficacy Outcome Measures
For subjects who have treatment success at Visit 1, an analysis similar to that for the primary efficacy outcome measure will be conducted for the percentage of subjects who maintain catheter function at Visits 2 and 3 (as defined earlier). The percentage of subjects who maintain catheter function at each visit will be computed, and 95% confidence intervals based on exact method will be provided. Subjects with treatment success at Visit 1 who discontinue from the study prior to completing Visits 2 and 3, or are not evaluable for BFR at those visits, will be considered to have had treatment failure with respect to the secondary outcome measures.
At Visit 1, the URR is calculated as follows:

$$\frac{(\text{pre-treatment BUN}) - (\text{post-HD BUN})}{(\text{pre-treatment BUN})}$$

At all other visits, the URR is calculated as follows:

$$\frac{(\text{pre-HD BUN})-(\text{post-HD BUN})}{(\text{pre-HD BUN})}$$

At each of Visits 1, 2, and 3, the percentage of subjects with a URR of ≥65% will be computed, and 95% exact confidence intervals will be provided. At Visit 1, the percentage of subjects with a URR of ≥65% will be compared between treatment groups using a Cochran-Mantel-Haenszel test stratified by dialysis timepoint and duration of dialysis. Subjects who discontinue prematurely from the study or are not evaluable for URR will be considered to have a URR of <65% for this outcome.

The mean change in BFR from baseline to the end of HD at Visit 1 will be summarized by treatment group, and 95% exact confidence intervals will be provided. Treatment comparison will be made by using a Cochran-Mantel-Haenszel test stratified by baseline BFR. Change in BFR from baseline to the end of HD at Visit 1 will also be analyzed using the following categories of change: <0 mL/min, 0-24 mL/min, 25-49 mL/min, 50-99 mL/min, 100-149 mL/min, and ≥150 mL/min. For these outcomes, subjects with missing BFR data will have values imputed using the LOCF approach. Alternative imputation methods (described in the Statistical Analysis Plan) will be used to evaluate robustness of the results.

Analyses similar to those for the above-mentioned primary and secondary outcome measures will be performed for the outcome measures pertaining to open-label administration of tenecteplase at Visit 2 (see Section 3.3.2). For these analyses, no treatment group comparison will be available, as all treated subjects will receive open-label tenecteplase.

c. Subgroup Analyses

Estimates and confidence intervals for the primary and secondary efficacy outcome measures and summaries of key safety outcomes will be presented for the following subgroups:

Age: <18, 18-65, >65 years
Sex: male, female
Baseline BFR: 0-199 mL/min, 200-274 mL/min, 275-299 mL/min Safety Analyses Verbatim descriptions of treatment-emergent adverse events will be mapped to preferred terms and body system terms using the MedDRA dictionary.

Targeted adverse events occurring from initial study drug administration up to the start of Visit 2 will be summarized by treatment group and targeted adverse event class. Similar summaries of all adverse events and serious adverse events by body system, high-level term, and preferred term will be generated over this same interval. These summaries will provide a controlled comparison of safety between tenecteplase- and placebo-treated subjects.

For subjects who go on to receive tenecteplase at Visit 2, targeted adverse events occurring from the start of Visit 2 through completion of Visit 4 will be summarized by targeted adverse event class. Similar summaries of all adverse events and serious adverse events by body system, high-level term, and preferred term will be generated for these subjects over this same interval.

For subjects not treated with tenecteplase at Visit 2, targeted adverse events occurring from the start of Visit 2 through completion of Visit 3 will be summarized by targeted adverse events class. Similar summaries of all adverse events and serious adverse events by body system, high-level term, and preferred term will be generated for these subjects over this same interval.

The results of anti-tenecteplase antibody testing during follow-up will be tabulated by baseline antibody status and tenecteplase exposure status.

Missing Data

For the purpose of analysis, subjects who discontinue from the study for any reason without having achieved treatment success (as defined above) and an increase from baseline BFR of ≥25 mL/min will be considered to have had treatment failure.

Determination of Sample Size

The primary efficacy outcome measure is the percentage of subjects who have treatment success (as defined above). Approximately 150 subjects will be enrolled and randomized in a 1:1 ratio to the tenecteplase group or placebo group. This sample size will give >90% power to detect a tenecteplase treatment success rate of 25% against a placebo success rate of 5% utilizing a two-sided $\chi^2$ test at the 0.05 level of significance.

Interim Analysis

A DMC will be formed and charged with performing periodic reviews of accumulating safety data during the study. The DMC will operate independently of the Sponsor and of Quintiles and will consist of clinicians with relevant therapeutic expertise and a biostatistician. The DMC will review cumulative safety data for the tenecteplase catheter clearance program, which includes studies of dysfunctional CVA and HD catheters (Studies N3698g, N3699g, N3700g, and N3701g), at predetermined intervals and will be responsible for making recommendations to the Sponsor regarding the continuing safety of the study, based on the results of this data review process. The specific guidelines and operating procedures for the DMC will be outlined in the DMC Charter.

Assessment of Safety

Safety assessments will consist of monitoring and recording adverse events (AEs) and serious adverse events (SAEs), including targeted AEs.

Adverse Events

An AE is any unfavorable and unintended sign, symptom, or disease temporally associated with the use of an investigational (medicinal) product or other protocol-imposed intervention, regardless of attribution.

This includes the following:
AEs not previously observed in the subject that emerge during the protocol-specified AE reporting period
Complications that occur as a result of protocol-mandated interventions (e.g., invasive procedures such as biopsies)
Preexisting medical conditions (other than the condition being studied) judged by the investigator to have worsened in severity or frequency or changed in character during the protocol-specified AE reporting period Serious Adverse Events An AE should be classified as an SAE if it meets the following criteria:
It results in death (i.e., the AE actually causes or leads to death).
It is life threatening (i.e., the AE, in the view of the investigator, places the subject at immediate risk of death. It does not include an AE that, had it occurred in a more severe form, might have caused death.).
It requires or prolongs inpatient hospitalization.
It results in persistent or significant disability/incapacity (i.e., the AE results in substantial disruption of the subject's ability to conduct normal life functions).
It results in a congenital anomaly/birth defect in a neonate/infant born to a mother exposed to the study drug.

It is considered a significant medical event by the investigator based on medical judgment (e.g., may jeopardize the subject or may require medical/surgical intervention to prevent one of the outcomes listed above).

All AEs that do not meet any of the criteria for serious should be regarded as non-serious AEs.

The terms "severe" and "serious" are not synonymous. Severity (or intensity) refers to the grade of a specific AE, e.g., mild (Grade 1), moderate (Grade 2), or severe (Grade 3) myocardial infarction. "Serious" is a regulatory definition (see previous definition) and is based on subject or event outcome or action criteria usually associated with events that pose a threat to a subject's life or functioning. Seriousness (not severity) serves as the guide for defining regulatory reporting obligations from the Sponsor to applicable regulatory authorities.

Severity and seriousness should be independently assessed when recording AEs and SAEs on the CRF.

Targeted Adverse Events

Events of particular interest (targeted AEs) will be specifically elicited and include the following:

ICH documented by computed tomography or magnetic resonance imaging

Major bleeding, defined as severe blood loss (>5 mL/kg), blood loss requiring transfusion, or blood loss causing hypotension Embolism, defined as any "serious" embolic event, including pulmonary events, arterial events (e.g., stroke, peripheral embolism, or major organ embolism), or cholesterol plaque Thrombosis, including catheter-related venous thrombosis, defined as thrombus identified by radiological imaging (e.g., ultrasound, angiogram, or magnetic resonance) in the upper or lower extremity arteries or veins that leads to pain, swelling, and/or ischemia of the limb CRBSI, further classified as follows:

Definite: the same organism from a semiquantitative culture of the catheter tip (>15 colony-forming units per catheter segment) and from a peripheral or catheter blood sample in a symptomatic subject with no other apparent source of infection Probable: defervescence of symptoms after antibiotic treatment, with or without removal of catheter, in the setting in which blood cultures confirm infection but catheter tip does not (or catheter tip does, but blood cultures do not) in a symptomatic subject with no other apparent source of infection Possible: defervescence of symptoms after antibiotic treatment or after removal of catheter in the absence of laboratory confirmation of bloodstream infection in a symptomatic subject with no other apparent source of infection Catheter-related complication, defined as rupture of the catheter during the flushing or instillation of drug, perforation of the indwelling vein, or bleeding at the catheter insertion site that would require surgical intervention (e.g., sutures or packing with gauze).

A targeted AE should be classified as an SAE if it meets the criteria described above for serious adverse effects, and should be reported.

Adverse Event Reporting Period

The study period during which all AEs and SAEs must be recorded begins at initiation of study treatment and ends upon completion of the second visit following the last administration of study treatment (i.e., Visit 3 for subjects who receive one treatment of study drug and Visit 4 for subjects who receive two treatments of study drug) or at subject discontinuation from the study, whichever is earlier.

Assessment of Adverse Events

The occurrence of AEs and SAEs will be assessed by the investigator at each subject evaluation timepoint during the study except at the follow-up visit at 30 days. All AEs and SAEs, whether volunteered by the subject, discovered by study personnel during questioning, or detected through physical examination, laboratory test, or other means, will be recorded in the subject's medical record and on the appropriate AE or SAE CRF page.

Each recorded AE or SAE will be described by its duration (i.e., start and end dates), severity (see Table 1), regulatory seriousness criteria if applicable, suspected relationship to study drug (see following guidance), and actions taken.

TABLE 1

Adverse Event Grading (Severity) Scale

| Severity | Description |
| --- | --- |
| Mild | Transient or mild discomfort (<48 hours); no interference with the subject's daily activities; no medical intervention/therapy required |
| Moderate | Mild to moderate interference with the subject's daily activities; no or minimal medical intervention/therapy required |
| Severe | Considerable interference with the subject's daily activities; medical intervention/therapy required; hospitalization possible |

Note:
Regardless of severity, some events may also meet regulatory seriousness criteria. Refer to definitions of an SAE herein.

To ensure consistency of AE and SAE causality assessments, investigators should apply the following general guideline:

Yes

There is a plausible temporal relationship between the onset of the AE and administration of the study drug, and the AE cannot be readily explained by the subject's clinical state, intercurrent illness, or concomitant therapies; and/or the AE follows a known pattern of response to the study drug; and/or the AE abates or resolves upon discontinuation of the study drug or dose reduction and, if applicable, reappears upon re-challenge.

No

Evidence exists that the AE has an etiology other than the study drug (e.g., preexisting medical condition, underlying disease, intercurrent illness, or concomitant medication); and/or the AE has no plausible temporal relationship to administration of the study drug (e.g., cancer diagnosed 2 days after first dose of study drug).

Note: The investigator's assessment of causality for individual AE reports is part of the study documentation process. Regardless of the "Yes" or "No" causality assessment for individual AE reports, the Sponsor will promptly evaluate all reported SAEs against cumulative product experience to identify and expeditiously communicate possible new safety findings to investigators and applicable regulatory authorities.

Eliciting Adverse Events

A consistent methodology of non-directive questioning for eliciting AEs at all subject evaluation timepoints should be adopted. Examples of non-directive questions include the following:

"How have you felt since your last clinical visit?"

"Have you had any new or changed health problems since you were last here?"

Specific Instructions for Recording Adverse Events on the CRF

Investigators should use correct medical terminology/concepts when recording AEs or SAEs on the CRF. Avoid colloquialisms and abbreviations.

All AEs should be recorded on an AE CRF page. There is designated space on this page to indicate if the event is serious (Y/N). For SAEs, an SAE CRF page must also be completed.

Only one medical concept should be recorded in the event field on the AE and SAE CRF pages.

a. Diagnosis versus Signs and Symptoms

If known at the time of reporting, a diagnosis should be recorded on the CRF rather than individual signs and symptoms (e.g., record only liver failure or hepatitis rather than jaundice, asterixis, and elevated transaminases). However, if a constellation of signs and/or symptoms cannot be medically characterized as a single diagnosis or syndrome at the time of reporting, each individual event should be recorded as an AE CRF page. If a diagnosis is subsequently established, it should be reported as follow-up information.

b. Adverse Events Occurring Secondary to Other Events

In general, AEs occurring secondary to other events (e.g., cascade events or clinical sequelae) should be identified by their primary cause. For example, if severe diarrhea is known to have resulted in dehydration, it is sufficient to record only diarrhea as an AE CRF page. However, if a medically significant secondary AE is separated in time from the initiating event, both should be recorded as independent events. For example, if a severe gastrointestinal hemorrhage leads to renal failure, both events should be recorded separate AE CRF pages.

c. Persistent or Recurrent Adverse Events

A persistent AE is one that extends continuously, without resolution, between subject evaluation timepoints. Such events should only be recorded once in the CRF unless their severity increases. If a persistent AE becomes more severe, it should be recorded again on an AE CRF page.

A recurrent AE is one that occurs, resolves, and subsequently recurs. All recurrent AEs should be recorded on an AE CRF page.

d. Clinical Laboratory Abnormalities

Individual laboratory abnormalities will generally not be recorded as AEs on the CRF. Only clinically significant laboratory abnormalities that result in study withdrawal, meet seriousness criteria, are themselves associated with clinical signs or symptoms, or require medical intervention (e.g., low hemoglobin requiring transfusion) will be recorded on an AE CRF page.

If the clinically significant laboratory abnormality is a sign of a disease or syndrome (e.g., alkaline phosphatase and bilirubin 5×the upper limit of normal associated with cholecystitis), only the diagnosis (e.g., cholecystitis) needs to be recorded on an AE CRF page.

If the clinically significant laboratory abnormality is not a sign of a disease or syndrome, the abnormality itself should be recorded on an AE CRF page. If the laboratory abnormality can be conveyed as a clinical diagnosis, the diagnosis should be recorded as the AE or SAE. For example, an elevated serum potassium level of 7.0 mEq/L should be recorded as "hyperkalemia."

Observations of the same clinically significant laboratory abnormality from visit to visit should not be repeatedly recorded on an AE CRF page, unless their severity, seriousness, or etiology changes.

e. Preexisting Medical Conditions

A preexisting medical condition is one that is present at the start of the study. Such conditions should be recorded on the Medical and Surgical History CRF page.

A preexisting medical condition should be re-assessed throughout the trial and recorded as an AE or SAE only if the frequency, severity, or character of the condition worsens during the study. When recording such events on an AE CRF page, it is important to convey the concept that the preexisting condition has changed by including applicable descriptors (e.g., "more frequent headaches").

f. Deaths

All deaths that occur during the protocol-specified AE reporting period, regardless of attribution, will be recorded on an AE CRF page and expeditiously reported to the Sponsor.

When recording a death, the event or condition that caused or contributed to the fatal outcome should be recorded as the single medical concept on an AE CRF page. If the cause of death is unknown and cannot be ascertained at the time of reporting, record "Unexplained Death" on an AE CRF page. The site should then make every attempt to urgently identify the cause of death (e.g., via primary care physician, autopsy report, hospital records) and expeditiously report the cause of death to the Sponsor.

g. Hospitalizations for Medical or Surgical Procedures

Any AE that results in hospitalization or prolonged hospitalization should be documented and reported as an SAE.

If a subject is hospitalized to undergo a medical or surgical procedure as a result of an AE, the event responsible for the procedure, not the procedure itself, should be recorded as the SAE. For example, if a subject is hospitalized to undergo coronary bypass surgery, record the heart condition that necessitated the bypass as the SAE.

Hospitalizations for the following reasons will not be recorded as SAEs on the CRF:

Hospitalization or prolonged hospitalization for diagnostic or elective surgical procedures for preexisting conditions that have not worsened in intensity or frequency and that are recorded on the Medical and Surgical History CRF Hospitalization or prolonged hospitalization required to allow efficacy measurement for the study Hospitalization or prolonged hospitalization for scheduled therapy of the target disease of the study

EXAMPLE 2

The goal of the study set forth in this Example is to examine the efficacy and safety of tenecteplase in the restoration of function to dysfunctional HD catheters, with no placebo control.

Objectives

The objectives of this study are as follows:

To evaluate the safety of tenecteplase in the treatment of subjects with dysfunctional HD catheters To evaluate the efficacy of tenecteplase in improving BFR in dysfunctional HD catheters Study Design This is a Phase III, open-label study that will be conducted at approximately 60 centers in the United States and Canada. Approximately 225 subjects ≥16 years of age who require HD and have a dysfunctional HD catheter, defined as a BFR that is <300 mL/min and at least 25 mL/min below the prescribed BFR at an arterial pressure of −250 mmHg (or at institutional guidelines for maximum negative arterial pressure, not to exceed 250 mmHg) during the first 30 minutes of HD, will be enrolled in the study.

The study will consist of visits that correspond to HD sessions for each subject, as well as one follow-up visit. Subjects will receive up to three treatments of open-label tenecteplase: one or two treatments as part of an initial treatment course and one additional treatment as part of a retreatment course (if indicated). At Visit 1, all subjects will have the first treatment of tenecteplase instilled into each lumen of the HD catheter. After a dwell time of 1 hour, subjects will undergo HD as prescribed or to the extent possible. BFR will be measured at the beginning of HD, every 30 minutes thereafter, 30 minutes before the end of HD, and at the end of HD to assess catheter function and determine treatment outcome. Subjects with a BFR of <300 mL/min at the end of HD at Visit 1 will have a second treatment instilled for an extended dwell time, until the start of Visit 2 (up to 72 hours). The extended-dwell tenecteplase will be withdrawn from the catheter at the beginning of Visit 2, and subjects will undergo HD as prescribed or to the extent possible. BFR will be measured at the beginning of HD, every 30 minutes thereafter, 30 minutes before the end of HD, and at the end of HD. Subjects who have treatment success at Visit 1 or Visit 2 (defined as a BFR of ≥300 mL/min and an increase from baseline BFR of □≥25 mL/min at an arterial pressure in the range of 0 to −250 mmHg, at the end of HD and 30 [±10] minutes prior to the end of HD) and have recurrent catheter dysfunction (BFR during the first 30 minutes of HD that is <300 mL/min and at least 25 mL/min below the prescribed BFR at an arterial pressure of −250 mmHg [or at institutional guidelines for maximum negative arterial pressure, not to exceed 250 mmHg]) within 21 days of Visit 1 will exit the initial treatment course and enter a retreatment course during which qualified subjects will receive another treatment of tenecteplase (at Retreatment [RT] Visit 1). After a dwell time of 1 hour, subjects will undergo HD as prescribed or to the extent possible. BFR will be measured at the beginning of HD, every 30 minutes thereafter, 30 minutes before the end of HD, and at the end of HD. All subjects will undergo follow-up assessments of HD catheter function at each of the two visits that follow final study drug exposure. Adverse events will be recorded for all subjects from treatment initiation through completion of the second visit following final study drug exposure. All subjects will undergo antibody testing 30-36 days after Visit 1 or upon early termination from the study.

Outcome Measures

Safety Outcome Measure

The primary safety outcome measure is as follows:
For subjects who do not receive extended-dwell tenecteplase at Visit 1, the incidence of targeted adverse events (intracranial hemorrhages, major bleeding, embolic events, thrombosis,
catheter-related bloodstream infections, and catheter-related complications) from initial study drug administration through the start of Visit 2

The secondary safety outcome measures are as follows:
For subjects who do not receive extended-dwell tenecteplase at Visit 1, the incidence of targeted adverse events (as listed above) from the start of Visit 2 through the completion of Visit 3
For subjects who receive extended-dwell tenecteplase at Visit 1, the incidence of targeted adverse events (as listed above) from the installation of extended-dwell tenecteplase through the completion of Visit 4
For subjects who enter the retreatment course, the incidence of targeted adverse events (as listed above) from the instillation of RT tenecteplase through the completion of RT Visit 3
For subjects who do not receive extended-dwell tenecteplase at Visit 1, the incidence of serious adverse events and the incidence of all adverse events from initial study drug administration through the start of Visit 2
For subjects who do not receive extended-dwell tenecteplase at Visit 1, the incidence of serious adverse events and the incidence of all adverse events from the start of Visit 2 through the completion of Visit 3
For subjects who receive extended-dwell tenecteplase at Visit 1, the incidence of serious adverse events and the incidence of all adverse events from the instillation of extended-dwell tenecteplase through the completion of Visit 4
For subjects who enter the retreatment course, the incidence of serious adverse events and the incidence of all adverse events from the instillation of RT tenecteplase through the completion of RT Visit 3
Incidence of positive anti-tenecteplase antibody tests in subjects who tested negative at baseline Efficacy Outcome Measures The primary efficacy outcome measure is as follows:
Percentage of subjects who have treatment success with respect to BFR at Visit 1 (as defined above; see "Study Design").

The secondary efficacy outcome measures are as follows:
For subjects who have treatment success at Visit 1 (as defined above), the percentage of subjects who maintain catheter function at Visits 2 and 3, defined as a BFR of ≥300 mL/min and an increase from baseline BFR of ≥25 mL/min at an arterial pressure in the range of 0 to −250 mmHg at the beginning of that HD session (within the first 30 minutes)
Percentage of subjects with a urea reduction ratio (URR) of ≥65% as assessed by pretreatment and post-HD blood urea nitrogen (BUN) measurements at Visit 1
For subjects who do not receive extended-dwell tenecteplase at Visit 1, the percentage of subjects with a URR of ≥65% as assessed by pre- and post-HD BUN measurements at Visit 2
Change in BFR from baseline to the end of HD at Visit 1
Percentage of subjects who fall into each of the following categories defined by change in BFR from baseline to the end of HD at Visit 1: <0 mL/min, 0-24 mL/min, 25-49 mL/min, 50-99 mL/min, 100-149 mL/min, and ≥150 mL/min For subjects treated with extended-dwell tenecteplase at Visit 1, secondary efficacy outcome measures also include the following:
Percentage of subjects who have treatment success with respect to BFR at Visit 2 (as defined above)
Percentage of subjects with a URR of ≥65% as assessed by pre- and post-HD BUN measurements at Visit 2
Percentage of subjects with a URR of 65% as assessed by pre- and post-HD BUN measurements at Visit 3
For subjects who have treatment success at Visit 2, the percentage of subjects who maintain catheter function at Visits 3 and 4 (as defined above)
Change in BFR from baseline to the end of HD at Visit 2
Percentage of subjects who fall into each of the following categories defined by change in BFR from baseline to the end of HD at Visit 2: <0 mL/min, 0-24 mL/min, 25-49 mL/min, 50-99 mL/min, 100-149 mL/min, and ≥150 mL/min For subjects who enter the retreatment course, secondary efficacy outcome measures also include the following:
Percentage of subjects who have treatment success with respect to BFR at RT Visit 1 (as defined above)

Percentage of subjects with a URR of ≥65% as assessed by pretreatment and post-HD BUN measurements at RT Visit 1

Percentage of subjects with a URR of ≥65% as assessed by pre- and post-HD BUN measurements at RT Visit 2

For subjects who have treatment success at RT Visit 1, the percentage of subjects who maintain catheter function at RT Visits 2 and 3 (as defined above)

Change in BFR from baseline to the end of HD at RT Visit 1

Percentage of subjects who fall into each of the following categories defined by change in BFR from baseline to the end of HD at RT Visit 1: <0 mL/min, 0-24 mL/min, 25-49 mL/min, 50-99 mL/min, 100-149 mL/min, and ≥150 mL/min.

Safety Plan

Tenecteplase is approved for use in the reduction of mortality associated with acute myocardial infarction (AMI). The adverse events associated with systemic use of tenecteplase at doses of 30-50 mg for treatment of AMI are well described and consist primarily of bleeding complications, including major bleeding events and intracranial hemorrhages. Another adverse event that could be associated with use of thrombolytics for treatment of dysfunctional catheters is embolization of a catheter-related thrombus. Based on the clinical experience with tenecteplase for treatment of AMI and CATHFLO® ACTIVASE® (alteplase) for treatment of dysfunctional central venous access catheters, it is anticipated that any potential bleeding or embolic events attributable to tenecteplase are most likely to occur within 24 hours of treatment. All adverse events will be recorded from initiation of study treatment through completion of the second visit following final study drug exposure.

Study Treatment

Subjects will receive up to three doses of open-label tenecteplase, depending on restoration of HD catheter function, as described above (see "Study Design"). At each administration, subjects will have 2 mL (2 mg) of tenecteplase instilled into each lumen of their HD catheter.

Concomitant Therapy and Clinical Practice

The use of fibrinolytic agents (other than study drug), warfarin (except for low-dose warfarin used for prophylaxis), and unfractionated or low molecular weight heparin (except for heparin used only during HD or for prophylaxis) is prohibited from Visit 1 through completion of the second visit following final study drug exposure. Subjects who are taking Plavix® (clopidogrel bisulfate) may not increase their dose from Visit 1 through completion of the second visit following final study drug exposure. Subjects may continue to receive other medications and standard treatments administered for their conditions at the discretion of the treating physician.

Statistical Methods

Primary Safety Analysis

The incidence of targeted adverse events from the time of initial study drug administration through the start of Visit 2 among subjects who do not receive the extended-dwell dose of tenecteplase will be summarized by body system, high-level term, and preferred term.

Missing Data

For the purpose of analysis, subjects who discontinue from the study for any reason without having achieved a BFR of ≥300 mL/min and an increase from baseline BFR of ≥25 mL/min will be considered to have had treatment failure.

Determination of Sample Size

The sample size of 225 subjects is considered to be large enough to estimate incidence rates of relatively common adverse events with adequate precision.

Interim Analysis

A DMC will perform periodic reviews of accumulating safety data during the study.

The abbreviations used in this study are the same as those noted above in Example 1.

Detailed Study Design

This is a Phase III, open-label study that will be conducted at approximately 60 centers in the United States and Canada. Approximately 225 subjects ≥16 years of age who require HD and have a dysfunctional HD catheter will be enrolled in the study. Subjects will be classified by baseline BFR into three strata: 0-199 mL/min, 200-274 mL/min, and 275-299 mL/min. Enrollment in the 0-199 mL/min and 275-299 mL/min strata will be limited to a maximum of 10% of subjects in each.

The study will consist of visits that correspond to HD sessions for each subject, as well as one follow-up visit. Subjects will receive up to three treatments of open-label tenecteplase during the study. Subjects will receive one or two treatments during an initial treatment course, and eligible subjects whose catheter becomes dysfunctional again within 21 days of the first visit will receive an additional treatment as part of a retreatment course.

After providing written informed consent (and children's informed assent, as applicable), subjects will be screened for eligibility based on the study inclusion and exclusion criteria (see Sections 4.1.2 and 4.1.3) at a screening visit. The screening visit and Visit 1 may be combined at the discretion of the investigator. At Visit 1, eligible subjects, with a BFR that is <300 mL/min and at least 25 mL/min below the prescribed BFR at an arterial pressure of −250 mmHg (or at institutional guidelines for maximum negative arterial pressure, not to exceed 250 mmHg) at the beginning of HD (within the first 30 minutes), will be treated with tenecteplase. The BFR measurement obtained at Visit 1 to determine study eligibility will be considered the baseline BFR. Subjects will have 2 mL (2 mg) of tenecteplase instilled into each of the two lumens of the HD catheter. After a dwell time of 1 hour, the study drug will be withdrawn and all subjects will undergo HD as prescribed or to the extent possible. BFR will be measured at the beginning of HD, every 30 minutes thereafter, 30 minutes before the end of HD, and at the end of HD to assess catheter function and determine treatment outcome for Visit 1 (see above).

Subjects with a BFR of <300 mL/min at the end of HD at Visit 1 will have 2 mL (2 mg) of tenecteplase instilled into each lumen of their catheter as part of the initial treatment course. The treatment will be left to dwell for an extended time, until the second HD session at Visit 2 (up to 72 hours later).

Subjects who receive the extended-dwell tenecteplase will have the treatment withdrawn from their catheter at the beginning of Visit 2. Subjects will undergo HD as prescribed or to the extent possible. BFR will be measured at the beginning of HD, every 30 minutes thereafter, 30 minutes before the end of HD, and at the end of HD to assess catheter function and determine treatment outcome for Visit 2.

Subjects who have treatment success at Visit 1 or Visit 2 and have recurrent catheter dysfunction (see Section 3.1.2.b below) within 21 days of Visit 1 will exit the initial treatment course and enter the retreatment course during which they will be screened for eligibility based on the retreatment inclusion and exclusion criteria (see Sections 4.1.4 and 4.1.5) and have 2 mL (2 mg) of tenecteplase instilled into each lumen, followed by a 1-hour dwell time (at Retreatment [RT] Visit 1). The BFR measurement used to determine eligibility for retreatment will be considered the RT baseline BFR. BFR will be measured at the beginning of HD, every 30 minutes thereafter, 30 minutes before the end of HD, and at the end of HD to assess catheter function and determine treatment outcome for RT Visit 1.

Follow-up assessments of HD catheter function will be performed by measuring BFR at the beginning of HD (within the first 30 minutes) at each of the two visits that follow final study drug exposure. For these assessments, study personnel will increase the BFR in an effort to achieve the prescribed BFR within the first 30 minutes.

If at any time the HD catheter is removed for any reason, no further treatments will be given and no additional efficacy assessments (i.e., BFR measurements or blood urea nitrogen [BUN] analysis) will be performed. However, subjects will continue to undergo safety assessments (i.e., recording of adverse events and concomitant medications and antibody testing). Subjects with symptomatic hypotension may not receive study drug.

Adverse events will be recorded for all subjects from treatment initiation through completion of the second visit following final study drug exposure. All subjects will undergo antibody testing 30-36 days after Visit 1 or upon early termination from the study.

BFR Assessments

All measurements of BFR in this study will be performed at an arterial pressure in the range of 0 to −250 mmHg. During each HD session, the BFR should be increased until the prescribed BFR is achieved. However, the BFR should not be increased to the point where the corresponding arterial pressure goes beyond −250 mmHg (e.g., −260 mmHg).

Each subject must be dialyzed on the same type and model of HD apparatus at Visits 1-4 to maintain consistency of data collected during HD. For subjects who enter the retreatment course, the same type and model of HD apparatus must be used for RT Visits 1-3; the apparatus may, however, be different than that used by the subject during the initial treatment course.

To be eligible for the study, subjects must have a baseline BFR that is <300 mL/min and at least 25 mL/min below the prescribed BFR at an arterial pressure of −250 mmHg (or at institutional guidelines for maximum negative arterial pressure, not to exceed 250 mmHg) during the first 30 minutes of HD. Subjects whose BFR cannot be measured because of total occlusion (i.e., no blood withdrawal function) should be considered to have a BFR of 0 mL/min.

HD Catheter Line Reversal

During this study, all BFR data must be collected using the catheter lines in the customary direction, that is, with the arterial (red, outlet) line of the HD catheter used for blood removal and the venous (blue, inlet) line used for blood return. If the investigator determines that line reversal is necessary to achieve fluid removal or electrolyte control, a BFR measurement must be recorded prior to reversal.

Determination of Treatment Outcome, Maintenance of Catheter Function, and Recurrent Catheter Dysfunction Treatment success for this study will be defined as follows: BFR of ≥300 mL/min and an increase from baseline BFR of ≥25 mL/min (without reversal of lines) at an arterial pressure in the range of 0 to −250 mmHg, at the end of HD and 30 (±10) minutes prior to the end of HD. Subjects with a BFR of ≥300 mL/min and an increase from baseline BFR of <25 mL/min, subjects with a BFR of <300 mL/min, and subjects for whom the catheter lines are reversed will be considered to have had treatment failure.

If an investigator determines that a subject has become hemodynamically unstable (decrease in blood pressure or change in heart rate) and requires his or her BFR to be decreased as a result, a BFR measurement must be recorded prior to decreasing the BFR. The BFR over the 30 minutes prior to development of hemodynamic instability will be used to determine treatment outcome.

For subjects who have treatment success at Visit 1 or Visit 2, maintenance of catheter function at subsequent visits is defined as a BFR of ≥300 mL/min and an increase from baseline BFR of ≥25 mL/min (without reversal of lines) at an arterial pressure in the range of 0 to −250 mmHg at the beginning of that HD session (within the first 30 minutes). For these assessments, study personnel will increase the BFR in an effort to achieve the prescribed BFR within the first 30 minutes.

Recurrent catheter dysfunction is defined as a BFR during the first 30 minutes of HD that is <300 mL/min and at least 25 mL/min below the prescribed BFR (using catheter lines in the customary direction) at an arterial pressure of −250 mmHg (or at institutional guidelines for maximum negative arterial pressure, not to exceed 250 mmHg).

This open-label clinical trial is designed to assess the safety and efficacy of tenecteplase for restoration of function to dysfunctional HD catheters. The rationale for the selected dose of tenecteplase is based on the approved dose of Cathflo Activase and experience with alteplase in CVA and HD catheters reported in the literature.

Cathflo Activase is currently approved for treatment of dysfunctional CVA devices. In clinical trials, up to two 2-mg doses of alteplase (with smaller doses for subjects weighing <30 kg), each followed by a dwell time of up to 120 minutes, were effective and safe in restoring function to dysfunctional CVA devices.

There will be no systemic administration in this study. However, in cases where the catheter lumen size is unknown or smaller than the specified dose of tenecteplase in this study (2 mL), the possibility exists for a portion of the administered dose (i.e., the difference between 2 mL and the catheter lumen volume) to enter the systemic circulation. This dosing regimen is not significantly different from the dosing regimen in the Cathflo Activase clinical trials (A2055g, A2065g, and A2404g), in which pediatric subjects weighing <30 kg were administered a dose equivalent to 110% of the catheter lumen volume. In a scenario in which the entire 2-mg dose was inadvertently given as an intravenous bolus, this would result in an expected maximum plasma concentration of 0.25 μg/mL. To put this in perspective, the maximum predicted concentration for 2 mg of alteplase is 0.58 μg/mL. In comparison, the 30-mg dose of tenecteplase commonly used in AMI would result in maximum plasma concentrations in the range of 5.9 to 7.5 μg/mL (mean data from the TIMI 10A and 10B trials) (Cannon et al. Circulation 1998; 98:2805-141 Cannon et al., Circulation 1997; 95:351-356). Similarly, patients given 100 mg of alteplase via the accelerated infusion regimen were predicted by Tanswell et al. (J Am Coll Cardiol. 1992 April; 19(5):1071-5) to achieve a maximum concentration of approximately 4 μg/mL. In comparison, the level of endogenously produced tissue plasminogen activator has been reported to be in the range of 0.002 to 0.021 μg/mL.

The rationale for limiting enrollment to subjects with a BFR of <300 mL/min at an arterial pressure of −250 mmHg is based on recommendations in the KDOQI guidelines on vascular access for HD, which suggest that a BFR of ≥300 mL/min is needed to provide adequate dialysis without lengthening the time of HD prohibitively. Since the BFR is directly related to the negative arterial pressure, an arterial pressure in the range of 0 to −250 mmHg was set for this study to maintain consistent conditions for the BFR determinations.

In addition, KDOQI guidelines suggest measuring BFR at an arterial pressure of −250 mmHg to determine catheter dysfunction.

Safety Outcome Measures

The primary safety outcome measure is as follows:

For subjects who do not receive extended-dwell tenecteplase at Visit 1, the incidence of targeted adverse events (ICHs, major bleeding, embolic events, thrombosis, catheter-related bloodstream infections [CRBSIs], and catheter-related complications) from initial study drug administration through the start of Visit 2

The secondary safety outcome measures are as follows:

For subjects who do not receive extended-dwell tenecteplase at Visit 1, the incidence of targeted adverse events (as listed above) from the start of Visit 2 through the completion of Visit 3

For subjects who receive extended-dwell tenecteplase at Visit 1, the incidence of targeted adverse events (as listed above) from the instillation of extended-dwell tenecteplase through the completion of Visit 4

For subjects who enter the retreatment course, the incidence of targeted adverse events (as listed above) from the instillation of RT tenecteplase through the completion of RT Visit 3

For subjects who do not receive extended-dwell tenecteplase at Visit 1, the incidence of serious adverse events and the incidence of all adverse events from initial study drug administration through the start of Visit 2

For subjects who do not receive extended-dwell tenecteplase at Visit 1, the incidence of serious adverse events and the incidence of all adverse events from the start of Visit 2 through the completion of Visit 3

For subjects who receive extended-dwell tenecteplase at Visit 1, the incidence of serious adverse events and the incidence of all adverse events from the instillation of extended-dwell tenecteplase through the completion of Visit 4

For subjects who enter the retreatment course, the incidence of serious adverse events and the incidence of all adverse events from the instillation of RT tenecteplase through the completion of RT Visit 3

Incidence of positive anti-tenecteplase antibody tests in subjects who tested negative at baseline Efficacy Outcome Measures The primary efficacy outcome measure is as follows:

Percentage of subjects who have treatment success with respect to BFR at Visit 1 (as defined above).

The secondary efficacy outcome measures are as follows:

For subjects who have treatment success at Visit 1, the percentage of subjects who maintain catheter function at Visits 2 and 3 (as defined above)

Percentage of subjects with a urea reduction ratio (URR) of 65% as assessed by pretreatment and post-HD BUN measurements at Visit 1

For subjects who do not receive extended-dwell tenecteplase at Visit 1, the percentage of subjects with a URR of ≥65% as assessed by pre- and post-HD BUN measurements at Visit 2

Change in BFR from baseline to the end of HD at Visit 1

Percentage of subjects who fall into each of the following categories defined by change in BFR from baseline to the end of HD at Visit 1: <0 mL/min, 0-24 mL/min, 25-49 mL/min, 50-99 mL/min, 100-149 mL/min, and ≥150 mL/min For subjects treated with extended-dwell tenecteplase at Visit 1, secondary efficacy outcome measures also include the following:

Percentage of subjects who have treatment success with respect to BFR at Visit 2 (as defined above)

Percentage of subjects with a URR of ≥65% as assessed by pre- and post-HD BUN measurements at Visit 2

Percentage of subjects with a URR of ≥65% as assessed by pre- and post-HD BUN measurements at Visit 3

For subjects who have treatment success at Visit 2, the percentage of subjects who maintain catheter function at Visits 3 and 4 (as defined above)

Change in BFR from baseline to the end of HD at Visit 2

Percentage of subjects who fall into each of the following categories defined by change in BFR from baseline to the end of HD at Visit 2: <0 mL/min, 0-24 mL/min, 25-49 mL/min, 50-99 mL/min, 100-149 mL/min, and ≥150 mL/min For subjects who enter the retreatment course, secondary efficacy outcome measures also include the following:

Percentage of subjects who have treatment success with respect to BFR at RT Visit 1 (as defined above)

Percentage of subjects with a URR of ≥65% as assessed by pretreatment and post-HD BUN measurements at RT Visit 1

Percentage of subjects with a URR of ≥65% as assessed by pre- and post-HD BUN measurements at RT Visit 2

For subjects who have treatment success at RT Visit 1, the percentage of subjects who maintain catheter function at RT Visits 2 and 3 (as defined above)

Change in BFR from baseline to the end of HD at RT Visit 1

Percentage of subjects who fall into each of the following categories defined by change in BFR from baseline to the end of HD at RT Visit 1: <0 mL/min, 0-24 mL/min, 25-49 mL/min, 50-99 mL/min, 100-149 mL/min, and ≥150 mL/min Safety Plan Tenecteplase is approved for use in the reduction of mortality associated with AML The adverse events associated with systemic use of tenecteplase at doses of 30-50 mg for treatment of AMI are well described and consist primarily of bleeding complications, including major bleeding events and ICHs. The elimination of tenecteplase from the plasma is biphasic, with a mean initial half-life of 20-24 minutes and a mean terminal half-life of 90-130 minutes (Modi et al., supra). Although the incidence of bleeding complications in subjects with AMI treated with tenecteplase has been quantified, data on the incidence of bleeding complications associated with the lower doses of tenecteplase used in this study are limited. The incidence of ICH and major bleeding attributed to tenecteplase is anticipated to be relatively low in this study because of the low proposed dose, minimal systemic exposure to tenecteplase, and the clinical trial experience to date with CATHFLO®ACTIVASE® (alteplase), which indicates that no ICHs have been reported and only 3 of 1432 subjects have experienced major bleeding.

Another adverse event that could be associated with use of thrombolytics for treatment of dysfunctional catheters is embolization of a catheter-related thrombus. Such an event could result in a pulmonary embolus, which could be life-threatening, depending on the size of the pulmonary embolus. The incidence of clinically significant embolic events associated with the use of tenecteplase for catheter clearance is expected to be low based on the extensive experience with both urokinase and Cathflo Activase in CVA catheters.

Based on the clinical experience with tenecteplase for treatment of AMI and Cathflo Activase for treatment of dysfunctional CVA catheters, it is anticipated that any potential bleeding or embolic events attributable to tenecteplase are most likely to occur within 24 hours of treatment.

All adverse events will be recorded from initiation of study treatment through completion of the second visit following final study drug exposure. All serious adverse events will be reported to Genentech within 48 hours, regardless of causality or treatment pathway. See Section 5 for complete details of the safety evaluation for this study.

A Data Monitoring Committee (DMC) will review cumulative safety data for the tenecteplase catheter clearance program, which includes studies of dysfunctional CVA and HD catheters (Studies N3698g, N3699g, N3700g, and N3701g), at predetermined intervals and will be responsible for making recommendations to the Sponsor regarding the continuing safety of the study, based on the results of this data review process.

Study Subjects and Analysis Groups

Subjects with dysfunctional HD catheters are eligible for this study and will be screened using criteria provided herein. There is no control group in this study.

Compliance with Laws and Regulations

This study will be conducted according to the U.S. FDA, the International Conference on Harmonisation E6 Guideline for Good Clinical Practice (GCP), and any national requirements.

Materials and Methods

Subject Selection for the Study

Subjects with a dysfunctional HD catheter, based on BFR during the first 30 minutes of HD (as defined above), are eligible for this study. Approximately 225 subjects from approximately 60 study sites in the United States and Canada will be enrolled. Subjects will be classified by baseline BFR into three strata: 0-199 mL/min, 200-274 mL/min, and 275-299 mL/min. Enrollment in the 0-199 mL/min and 275-299 mL/min strata will be limited to a maximum 10% of subjects in each. Subjects will be screened using the inclusion and exclusion criteria listed below.

Inclusion Criteria

Subjects must meet all of the following criteria to be eligible for inclusion in the study:
- Able to provide written informed consent and comply with the study assessments for the full duration of the study
- Age ≥16 years
- Clinically stable, in the opinion of the investigator
- Use of a cuffed tunneled HD catheter with a BFR of <300 mL/min at a maximum negative arterial pressure of 250 mmHg, but with a demonstrated BFR of ≥300 mL/min in at least one HD session in the 7 days prior to Visit 1
- HD prescribed at a BFR of ≥300 mL/min
- Baseline BFR (during the first 30 minutes of HD) of <300 mL/min (using catheter lines in the customary direction, prior to any reversal of lines; see Section 3.1.2.a) at an arterial pressure of −250 mmHg (or at institutional guidelines for maximum negative arterial pressure, not to exceed 250 mmHg)
- Baseline BFR (during the first 30 minutes of HD) at least 25 mL/min below the prescribed BFR
- For example, subjects with HD prescribed at a BFR of 300 mL/min must have a BFR of ≤275 mL/min to enter the study.
- Demonstrated BFR of ≥300 mL/min (using catheter lines in the customary direction) at an arterial pressure in the range of 0 to −250 mmHg in at least one HD session in the 7 days prior to Visit 1
- Anticipated use of the same catheter for at least the next 30 days, on the same type and model of HD apparatus
- Able to have fluids infused at the volume necessary to instill study drug into the HD catheter Exclusion Criteria for the Study Subjects who meet any of the following criteria will be excluded from the study:
- HD catheter with sustainable BFR of ≥300 mL/min following subject repositioning
- HD catheter inserted <2 days prior to screening
- Evidence of mechanical, non-thrombotic cause of HD catheter dysfunction (e.g., kink in the catheter or suture constricting the catheter), or dysfunction caused by known fibrin sheath
- Use of an implantable port
- HD catheter not implanted in the subclavian vein
- Anticipated use of catheter for any other type of diagnostic or therapeutic procedure (i.e., other than HD) during the course of the study
- Previously treated in this study or any tenecteplase catheter clearance trial
- Use of any investigational drug or therapy within 28 days prior to screening
- Use of a fibrinolytic agent (e.g. alteplase, tenecteplase, reteplase, or urokinase) within 7 days prior to Visit 1
- Known to be pregnant or lactating at screening
- HD catheter with known or suspected infection
- History of any intracranial hemorrhage, aneurysm, or arteriovenous malformation
- Use of any heparin (unfractionated or low molecular weight) within 24 hours prior to Visit 1, except for heparin used only during HD or for prophylaxis (e.g., heparin lock)
- Use of warfarin within 7 days prior to Visit 1, except for low-dose warfarin used for prophylaxis
- Initiation of or increase in dose of Plavix (clopidogrel bisulfate) within 7 days prior to Visit 1
- Hemoglobin ≥13.5 g/dL if on erythropoietin
  - A laboratory test to confirm hemoglobin levels must have been performed within 30 days prior to screening.
- Platelet count <75,000/μL
  - A laboratory test to confirm platelet count must have been performed within 30 days prior to screening.
- At high risk for bleeding events or embolic complications (i.e., recent pulmonary embolus, deep vein thrombosis, endarterectomy, or clinically significant right-to-left shunt) in the opinion of the investigator, or with known condition for which bleeding constitutes a significant hazard
- BFR of <300 mL/min because of symptomatic hypotension
- Uncontrolled hypertension in the opinion of the investigator (e.g., systolic pressure >185 mmHg and diastolic pressure >110 mmHg)
- Known hypersensitivity to tenecteplase or any component of the formulation Inclusion Criteria for the Retreatment Course Subjects must meet all of the following criteria to be eligible for inclusion in the retreatment course of the study:
- Treatment success at Visit 1 or Visit 2 (as defined above)
- Clinically stable, in the opinion of the investigator
- Continued use of the same cuffed, tunneled HD catheter (i.e., the catheter the subject had in place during the initial treatment course)
- HD prescribed at a BFR of ≥300 mL/min
- RT baseline BFR of <300 mL/min (using catheter lines in the customary direction, prior to any reversal of lines; see Section 3.1.2.a) at an arterial pressure of −250 mmHg (or at institutional guidelines for maximum negative arterial pressure, not to exceed 250 mmHg)

RT baseline BFR at least 25 mL/min below the prescribed BFR
    For example, subjects with HD prescribed at a BFR of 300 mL/min must have a BFR of ≤275 mL/min to enter the retreatment course.
Anticipated use of the same catheter for at least three consecutive HD sessions, on the same type and model of HD apparatus
Able to have fluids infused at the volume necessary to instill study drug into the HD catheter Exclusion Criteria for the Retreatment Course Subjects who meet any of the following criteria will be excluded from the retreatment course of the study:

HD catheter with sustainable BFR of ≥300 mL/min following subject repositioning
Evidence of a mechanical, non-thrombotic cause of HD catheter dysfunction (e.g., kink in the catheter or suture constricting the catheter), or dysfunction caused by known fibrin sheath
Anticipated use of catheter for any other type of diagnostic or therapeutic procedure (i.e., other than HD) during the retreatment course of the study
Use of any investigational drug or therapy other than tenecteplase within 21 days prior to RT Visit 1
Use of a fibrinolytic agent other than tenecteplase in this study (e.g. alteplase, reteplase, or urokinase) within 7 days prior to RT Visit 1
Known to be pregnant or lactating at RT Visit 1
HD catheter with known or suspected infection
History of any intracranial hemorrhage, aneurysm, or arteriovenous malformation
Use of any heparin (unfractionated or low molecular weight) within 24 hours prior to RT Visit 1, except for heparin used only during HD or for prophylaxis (e.g., heparin lock)
Use of warfarin within 7 days prior to RT Visit 1, except for low-dose warfarin used for prophylaxis
Initiation of or increase in dose of clopidogrel bisulfate within 7 days prior to RT Visit 1
Known hemoglobin ≥13.5 g/dL between initial treatment course and RT Visit 1 if on erythropoietin
Known platelet count <75,000/μL between initial treatment course and RT Visit 1
At high risk for bleeding events or embolic complications (i.e., recent pulmonary embolus, deep vein thrombosis, endarterectomy, or clinically significant right-to-left shunt) in the opinion of the investigator, or with known condition for which bleeding constitutes a significant hazard
BFR of <300 mL/min because of symptomatic hypotension
Uncontrolled hypertension in the opinion of the investigator (e.g., systolic pressure >185 mmHg and diastolic pressure >110 mmHg)
Known hypersensitivity to tenecteplase or any component of the formulation Formulation Tenecteplase is supplied in single-use, 6-cc glass vials with DAIKYO™ stoppers and flip-off aluminum caps. Tenecteplase is provided as a sterile, lyophilized formulation containing 2 mg of protein, with specifications for the following excipients: 104.4 mg of L-arginine, 32 mg of phosphoric acid, and 0.8 mg of polysorbate 20. The diluent used is Sterile Water for Injection, USP/EP (SWFI).

Dosage, Administration, and Storage

Subjects will receive up to three treatments of tenecteplase, depending on restoration of HD catheter function. At each treatment, subjects will have 2 mL (2 mg) of tenecteplase instilled into each lumen of their HD catheter. If at any time the HD catheter is removed for any reason, no further treatments will be given. Subjects with symptomatic hypotension may not receive study drug.

Reconstitute each vial of lyophilized tenecteplase immediately before use with 2.2 mL of BWFI. Direct the flow of BWFI directly into the lyophilized cake of study drug using aseptic technique, and gently swirl the vial until the contents are dissolved. Do not shake. The concentration of tenecteplase in the resulting solution will be 1 mg/mL. Slight foaming upon reconstitution is not unusual; any large bubbles will dissipate if the vial is allowed to stand undisturbed for several minutes. If the reconstituted study drug is not used immediately, the solution must be stored at 2° C.-8° C. (36° F46° F.) and used within 8 hours of reconstitution. Discard any unused solution.

Just prior to administering study drug, withdraw any fluid in the HD catheter lumen and attempt to flush with saline. To administer the dose, 2 mL of reconstituted study drug should be drawn into a single 10-mL syringe using aseptic technique. The solution should then be instilled into one HD catheter lumen according to the institution's guidelines. The remaining volume of the catheter should be backfilled with normal saline. Repeat for the second lumen.

Store vials of study drug under refrigeration at 2° C.-8° C. (36° F.-46° F.). Do not store the unused portion of any vial for future use. Do not use study drug beyond the expiration date on the vial or expiration extension documentation provided by Genentech. Partially used vials, empty vials, and unreconstituted vials will be returned to Genentech.

Dosage Modification

No dose modifications are allowed.

Concomitant and Excluded Therapies

Subjects will not be allowed to receive any intravenous therapy or provide blood samples through the HD catheter while study drug is in the catheter. Intravenous therapy or procurement of blood samples is acceptable only through use of a separate route. The use of fibrinolytic agents (other than study drug), warfarin, (except for low-dose warfarin used for prophylaxis), and unfractionated or low molecular weight heparin (except for heparin used only during HD or for prophylaxis) is prohibited from Visit 1 through completion of the second visit following final study drug exposure. Subjects who are taking clopidogrel bisulfate may not increase their dose from Visit 1 through completion of the second visit following final study drug exposure. Subjects may continue to receive other medications and standard treatments administered for their conditions at the discretion of the treating physician.

Study Assessments

The study will consist of visits that correspond to consecutive HD sessions based on each subject's regular HD schedule, as well as one follow-up visit. The screening visit and Visit 1 may be combined at the discretion of the investigator. Subjects will receive up to three treatments of tenecteplase, the first two treatments as part of the initial treatment course and one additional treatment as part of the retreatment course. The first treatment, followed by a 1-hour dwell time, will be given to all subjects at Visit 1. At the end of HD at Visit 1, eligible subjects will have a second treatment instilled for an extended dwell time, until the start of Visit 2 (up to 72 hours). Subjects who have treatment success at Visit 1 or Visit 2 and have recurrent catheter dysfunction (as hereinabove defined) within 21 days of Visit 1 will exit the initial treatment course and enter the retreatment course, during which qualified subjects will receive another dose of tenecteplase followed by a 1-hour dwell time (at Retreatment Visit 1). All subjects will undergo follow-up assessments of HD catheter function at each of the two visits that follow final study drug exposure. The assessments performed at each visit will vary by subject, depending on the individual response to each study drug treatment. All subjects will return for a follow-up visit 30 (up to 36) days after Visit 1 or upon early termination from the study.

If at any time the HD catheter is removed for any reason, no further treatments will be given and no additional efficacy assessments (i.e., BFR measurements or BUN analysis) will be performed. However, subjects will continue to undergo safety assessments (i.e., recording of adverse events and concomitant medications and antibody testing).

Laboratory kits and instructions for collection of BUN and anti-tenecteplase antibody samples will be provided by a central laboratory, Quintiles Laboratories (QLab). All samples will be processed at the site and shipped to QLab. QLab will perform BUN analysis, calculate URR and will ship the antibody samples to Genentech for testing.

Screening Visit

Any or all of the screening assessments may be performed at Visit 1 (before enrollment) at the discretion of the investigator. Written informed consent/assent MUST be obtained before any study-specific assessments or procedures are performed.

The following screening assessments and procedures will be performed:
  Written informed consent/assent
  Review of study inclusion and exclusion criteria (see Sections 4.1.2 and 4.1.3)
  Demographic data, including the subject's birth date, sex, and race/ethnicity
  Physical examination and medical history, including the two most recent URR values (historical baseline)
    If a physical examination is not medically indicated at the screening visit, a historical physical examination may be used, as long as it was performed within 7 days prior to screening.
  Vital signs, including blood pressure, respiratory rate, temperature, and pulse (specify if pre- or post-HD)
  Weight (specify if pre- or post-HD)
  Blood sample to determine hemoglobin level (if subject is on erythropoietin) and platelet count, if laboratory tests confirming eligibility were not performed within 30 days prior to screening
  Concomitant medications
  HD catheter history and information
    Information on the date of HD catheter insertion and the date the HD catheter was last known to have function (BFR of ≥300 mL/min) will be recorded. HD catheter lumen size, type, volume, brand (if known), and placement location will also be recorded.
  HD prescription Visit 1

Visit 1 must be performed within 7 days after screening (as stated above, the screening visit and Visit 1 may be combined at the discretion of the investigator). At the beginning of Visit 1, the following should be performed to verify eligibility:
  Review of study inclusion and exclusion criteria (see Sections 4.1.2 and 4.1.3)
  Review of concomitant medication and medical history (to ensure no changes since screening), including use of fibrinolytics, warfarin, and clopidogrel bisulfate within 7 days prior to Visit 1 and use of heparin within 24 hours prior to Visit 1 (see Section 4.1.3)
  HD prescription
  HD, initiated as prescribed
  Baseline BFR, measured at the beginning of HD (within the first 30 minutes) to confirm HD catheter dysfunction
    Subjects with a BFR that is <300 mL/min and at least 25 mL/min below the prescribed BFR (using catheter lines in the customary direction) at an arterial pressure of −250 mmHg (or at institutional guidelines for maximum negative arterial pressure, not to exceed 250 mmHg) are eligible for the study; all other subjects are ineligible. Baseline BFR will be recorded at the time it is first determined that a subject is eligible for the study (i.e., when arterial pressure reaches −250 mmHg).
    If an attempt has been made to dialyze with the lines reversed (i.e., before opting for study drug treatment), BFR must be recorded prior to line reversal and will be used as the baseline value.
    Subjects whose BFR cannot be measured because of total occlusion (i.e., no blood withdrawal function) should be considered to have a baseline BFR of 0 mL/min.

Eligible subjects will have their HD interrupted. Ineligible subjects may complete their prescribed HD session and should be registered as having failed screening.

Once eligibility has been verified, the subject will be enrolled using an interactive voice response system (IVRS). The following assessments and procedures will also be performed at Visit 1:
  Blood sample for serum anti-tenecteplase antibody testing, collected prior to treatment with tenecteplase
  Blood sample for BUN analysis, collected prior to treatment with tenecteplase
  Tenecteplase administration, prior to resuming HD
    Tenecteplase will be administered as described in Section 4.3.2 and will be left to dwell, undisturbed, in the subject's HD catheter (both lumens) for 1 hour. After the 1-hour dwell, tenecteplase will be withdrawn.
    Subjects with symptomatic hypotension may not receive study drug.
  HD, resumed and performed as prescribed or to the extent possible
  BFR, measured at the beginning of HD, every 30 minutes thereafter, 30 minutes before the end of HD, and at the end of HD to determine treatment outcome (as defined in Section 3.1.2.b)
    If it becomes necessary to dialyze with the catheter lines reversed, a BFR measurement will be recorded prior to reversal and no additional BFR measurements will be recorded during this HD session.
    If an investigator determines that a subject requires his or her BFR to be decreased because of hemodynamic instability, a BFR measurement will be recorded prior to decreasing the BFR. Subsequent BFRs will continue to be recorded as scheduled.
  Blood sample for BUN analysis, collected upon completion of HD
    If the catheter lines have been reversed, no blood sample will be taken.
  Adverse events and changes in concomitant medications during this visit
    Monitoring of adverse events will begin upon initiation of study treatment.
    Subjects with a BFR of <300 mL/min at the end of HD will be treated with a second treatment of tenecteplase as described in Section 4.3.2. Study drug will be left to dwell, undisturbed, in the subject's HD catheter (both lumens) until the second HD session at Visit 2 (up to 72 hours). Subjects with symptomatic hypotension may not receive study drug.

Visit 2

The following assessments and procedures will be performed at Visit 2:

Adverse events and changes in concomitant medications since the last visit

For subjects who received extended-dwell tenecteplase at Visit 1 only: Removal of extended-dwell tenecteplase from HD catheter (within 72 hours after instillation), prior to HD HD prescription Blood sample for BUN analysis, collected prior to HD
Discard this blood sample if subject becomes eligible for retreatment based on initial BFR (see below).

HD, initiated as prescribed

BFR, measured at the beginning of HD (within the first 30 minutes) to assess HD catheter function
For these assessments, study personnel will increase the BFR in an effort to achieve the prescribed BFR within the first 30 minutes.

Subjects who had treatment success at Visit 1 but have recurrent catheter dysfunction (as defined in Section 3.1.2.b) and qualify for retreatment at the beginning of Visit 2 will have their HD interrupted, exit the initial treatment course, and enter the retreatment course (see Section 4.5.6). All other subjects will continue their prescribed HD session to the extent possible and have the following assessments and procedures performed:

For subjects who received extended-dwell tenecteplase at Visit 1 only: BFR, measured at the beginning of HD, every 30 minutes thereafter, 30 minutes before the end of HD, and at the end of HD to determine treatment outcome (as defined in Section 3.1.2.b)
If it becomes necessary to dialyze with the catheter lines reversed, a BFR measurement will be recorded prior to reversal and no additional BFR measurements will be recorded during this HD session.
If an investigator determines that a subject requires his or her BFR to be decreased because of hemodynamic instability, a BFR measurement will be recorded prior to decreasing the BFR. Subsequent BFRs will continue to be recorded as scheduled.

Blood sample for BUN analysis, collected upon completion of HD
If the catheter lines have been reversed, no blood sample will be taken.

Adverse events and changes in concomitant medications during this visit

Visit 3

The following assessments and procedures will be performed at Visit 3:

Adverse events and changes in concomitant medications since the last visit

HD prescription

For subjects who received extended-dwell tenecteplase at Visit 1 only: Blood sample for BUN analysis, collected prior to HD
Discard this blood sample if subject becomes eligible for retreatment based on initial BFR (see below).

HD, performed as prescribed or to the extent possible

BFR, measured at the beginning of HD (within the first 30 minutes) to assess HD catheter function
For these assessments, study personnel will increase the BFR in an effort to achieve the prescribed BFR within the first 30 minutes.

Subjects who had treatment success at Visit 1 or Visit 2 but have recurrent catheter dysfunction (as defined in Section 3.1.2.b) and qualify for retreatment at the beginning of Visit 3 will have their HD interrupted, exit the initial treatment course, and enter the retreatment course (see Section 4.5.6). All other subjects will continue their prescribed HD session and have the following assessments and procedures performed:

For subjects who received extended-dwell tenecteplase at Visit 1 only: Blood sample for BUN analysis, collected upon completion of HD
If the catheter lines have been reversed, no blood sample will be taken. Adverse events and changes in concomitant medications during this visit Visit 4

Visit 4 is required only for subjects who received extended-dwell tenecteplase at Visit 1. Those subjects will have the following study assessments and procedures performed:

Adverse events and changes in concomitant medications since the last visit

HD prescription

HD, performed as prescribed or to the extent possible

BFR, measured at the beginning of HD (within the first 30 minutes) to assess HD catheter function
For these assessments, study personnel will increase the BFR in an effort to achieve the prescribed BFR within the first 30 minutes.

Subjects who had treatment success at Visit 1 or Visit 2 but have recurrent catheter dysfunction (as defined in Section 3.1.2.b) and qualify for retreatment at the beginning of Visit 4 will have their HD interrupted, exit the initial treatment course, and enter the retreatment course (see Section 4.5.6). All other subjects will continue their prescribed HD session and have the following assessments and procedures performed: Adverse events and changes in concomitant medications during this visit Retreatment Course Subjects who have treatment success at Visit 1 or Visit 2 and have recurrent catheter dysfunction (as hereinabove defined) within 21 days of Visit 1 will exit the initial treatment course and enter a retreatment course during which they will be screened for eligibility based on retreatment inclusion and exclusion criteria (see description before) and receive another treatment of tenecteplase followed by a 1-hour dwell time. Th same type and model of HD apparatus should be used for HD at all three retreatment visits. The retreatment course will consist of three visits, as described herein.

Subjects who enter the retreatment course before completing any or all of Visits 2, 3, or 4 (as applicable) will skip all subsequent visits associated with the initial treatment course and will instead complete the three retreatment (RT) visits only. For example, a subject who has treatment success at Visit 1 and is found to have recurrent catheter dysfuction at the beginning of Visit 2 will then undergo assessments and procedures for RT Visit 1 rather than Visit 2. Thus, during the course of this study, the subject will have undergone assessments and procedures outlined for Visit 1, RT Visits 1-3, and a follow-up visit 30 days after Visit 1.

a. RT Visit 1

Subjects who qualify for retreatment will be enrolled using the IVRS. Subjects will have the following assessments and procedures performed at RT Visit 1:

BFR that qualified subject for retreatment (RT baseline BFR)

Review of retreatment inclusion and exclusion criteria (see Sections 4.1.4 and 4.1.5)

Subjects who do not meet these criteria will continue to be followed according to the schedule outlined for the initial treatment course.

Updated concomitant medication and medical history

HD prescription

Blood sample for BUN analysis, collected prior to treatment with tenecteplase

Tenecteplase administration, prior to resuming HD
  Tenecteplase will be administered as described in Section 4.3.2 and will be left to dwell, undisturbed, in the subject's HD catheter (both lumens) for 1 hour. After the 1-hour dwell, tenecteplase will be withdrawn.
  Subjects with symptomatic hypotension may not receive study drug.

HD, resumed and performed as prescribed or to the extent possible

BFR, measured at the beginning of HD, every 30 minutes thereafter, 30 minutes before the end of HD, and at the end of HD to determine treatment outcome (as defined in Section 3.1.2.b)
  If it becomes necessary to dialyze with the catheter lines reversed, a BFR measurement will be recorded prior to reversal and no additional BFR measurements will be recorded during this HD session.
  If an investigator determines that a subject requires his or her BFR to be decreased because of hemodynamic instability, a BFR measurement will be recorded prior to decreasing the BFR. Subsequent BFRs will continue to be recorded as scheduled.

Blood sample for BUN analysis, collected upon completion of HD
  If the catheter lines have been reversed, no blood sample will be taken. Adverse events and changes in concomitant medications during this visit b. RT Visits 2 and 3

The following assessments and procedures will be performed at RT Visits 2 and 3:

Adverse events and changes in concomitant medications since the last visit

HD prescription

RT Visit 2 only: Blood sample for BUN analysis, collected prior to HD

HD, performed as prescribed or to the extent possible

BFR, measured at the beginning of HD (within the first 30 minutes) to assess HD catheter function
  For these assessments, study personnel will increase the BFR in an effort to achieve the prescribed BFR within the first 30 minutes.

RT Visit 2 only: Blood sample for BUN analysis, collected upon completion of HD
  If the catheter lines have been reversed, no blood sample will be taken. Adverse events and changes in concomitant medications during this visit Follow-Up at 30 days or Early Termination All subjects will have blood drawn for anti-tenecteplase antibody testing at 30 days (up to 36 days) after Visit 1 or upon early termination from the study. Information on catheter status will also be collected at this visit. Adverse events will be recorded at early termination if this occurs prior to the second visit following the last administration of study treatment.

Subject Discontinuation

Subjects have the right to withdraw from the study at any time.

The investigator has the right to withdraw a subject for any reason that is in the best interest of the subject, including intercurrent illness, adverse events, or worsening condition. Genentech reserves the right to request withdrawal of a subject because of a protocol violation, administrative reasons, a decision to limit or terminate the study for any reason, or any other valid and ethical reason.

Study Discontinuation

Genentech has the right to terminate this study at any time. Reasons for terminating the study may include, but are not limited to, the following:
  The incidence or severity of adverse events in this or other studies indicates a potential health hazard to subjects.
  Subject enrollment is unsatisfactory.
  Data recording is inaccurate or incomplete.

Statistical Methods

This is an open-label, single-arm study. All subjects enrolled and treated with tenecteplase will be included in the safety and efficacy analyses.

Analysis of the Conduct of the Study

Enrollment, number of tenecteplase administrations, major protocol violations, discontinuations from the study, and reasons for discontinuation will be summarized.

Safety Analyses

Verbatim descriptions of treatment-emergent adverse events will be mapped to preferred terms and body system terms using the MedDRA dictionary.

The primary safety outcome measure is the incidence of targeted adverse events from time of initial study drug administration through the start of Visit 2 among subjects who do not receive the extended-dwell dose of tenecteplase. Targeted adverse events will be summarized by targeted advserse event class. Similar summaries of all adverse events and serious adverse events by body system, high-level term, and preferred term will be generated over this same interval. Similar summaries will be generated for targeted adverse events, all adverse events, and serious adverse events occurring from the start of Visit 2 through the end of Visit 3.

For those subjects who receive the extended-dwell dose of tenecteplase, targeted adverse events occurring from administration of the extended-dwell dose through the end of Visit 4 will be summarized by targeted adverse event class. Similar summaries of all adverse events and serious adverse events by body system, high-level term and preferred term will be generated for these subjects over this same interval. For subjects who receive extended-dwell tenecteplase, summaries of targeted adverse events, serious adverse events, and all adverse events occurring from initial tenecteplase administration through initiation of extended-dwell tenecteplase will be generated.

For subjects re-treated with tenecteplase because of recurrent catheter dysfunction, targeted adverse events occurring from the administration of RT tenecteplase through the end of RT Visit 3 will be summarized by targeted adverse event class. Similar summaries of all adverse events and serious adverse events by body system, high-level term, and preferred term will be generated for these subjects over this same interval.

Efficacy Analyses a. Primary Efficacy Outcome Measure

The primary efficacy outcome measure is the percentage of subjects who have treatment success with respect to BFR at Visit 1 (as defined hereinbefore). Subjects who discontinue from the study before completing HD, or are otherwise not evaluable for the primary outcome measure, will be considered to have had treatment failure with respect to the primary outcome measure. The percentage of subjects who achieve treatment success will be computed, and 95% confidence intervals based on exact method will be provided. Sensitivity analyses will be conducted to evaluate robustness of the primary results to alternative missing data methods, including complete case analysis and last observation carried forward (LOCF) imputation.

b. Secondary Efficacy Outcome Measures

For subjects who have treatment success at Visit 1, an analysis similar to that for the primary efficacy outcome measure will be conducted for the percentage of subjects who maintain catheter function at Visits 2 and 3 (as defined hereinbefore). The percentage of subjects who maintain catheter function at each visit will be computed, and 95% confidence intervals based on exact method will be provided. Subjects with treatment success at Visit 1 who discontinue from the study prior to completing Visits 2 and 3, or are not evaluable for BFR at those visits, will be considered to have had treatment failure with respect to this secondary outcome measure.

At Visit 1 and RT Visit 1, the URR is calculated as follows:

$$\frac{(\text{pre-treatment BUN}) - (\text{post-HD BUN})}{(\text{pre-treatment BUN})}$$

At all other visits, the URR is calculated as follows:

$$\frac{(\text{pre-HD BUN}) - (\text{post-HD BUN})}{(\text{pre-HD BUN})}$$

At Visits 1-3 and RT Visits 1 and 2, the percentage of subjects with a URR of ≥65% will be computed, and 95% exact confidence intervals will be provided. Subjects who discontinue prematurely from the study or are not evaluable for URR will be considered to have a URR of <65% for this outcome.

The mean change in BFR from baseline to the end of HD at Visit 1 will be summarized, and 95% exact confidence intervals will be provided. Change in BFR from baseline to the end of HD at Visit 1 will be analyzed using the following categories of change: <0 mL/min, 0-24 mL/min, 25-49 mL/min, 50-99 mL/min, 100-149 mL/min, and ≥150 mL/min. For these outcomes, subjects with missing BFR data will have values imputed using the LOCF approach. Alternative imputation methods will be used to evaluate robustness of the results.

Analyses similar to those for the above-mentioned primary and secondary outcome measures will be performed for the outcome measures pertaining to administration of extended-dwell tenecteplase and tenecteplase retreatment.

c. Subgroup Analyses

Estimates and confidence intervals for the primary and secondary efficacy outcome measures and summaries of key safety outcomes will be presented for the following subgroups:

Age: <18, 18-65, >65 years
Sex: male, female
Baseline BFR: 0-199 mL/min, 200-274 mL/min, 275-299 mL/min Missing Data For the purpose of analysis, subjects who discontinue from the study for any reason without having achieved treatment success (as defined herein) will be considered to have had treatment failure.

Determination of Sample Size

Approximately 225 subjects will be enrolled. This sample size is considered to be large enough to estimate incidence rates of relatively common adverse events with adequate precision.

Interim Analysis

A DMC will be formed and charged with performing periodic reviews of accumulating safety data during the study. The DMC will operate independently of the Sponsor and of Quintiles and will consist of clinicians with relevant therapeutic expertise and a biostatistician. The DMC will review cumulative safety data for the tenecteplase catheter clearance program, which includes studies of dysfunctional CVA and HD catheters (Studies N3698g, N3699g, N3700g, and N3701g), at predetermined intervals and will be responsible for making recommendations to the Sponsor regarding the continuing safety of the study, based on the results of this data review process. The specific guidelines and operating procedures for the DMC will be outlined in the DMC Charter.

Data Quality Assurance

Quintiles will supply Case Report Forms (CRFs) for this study. Quintiles will be responsible for data management of this trial, including double data entry and quality checking of the data. In the event of discrepant data, Quintiles will send requests for data clarification to the sites for resolution. Quintiles will produce a Data Quality Plan that describes the quality checking to be performed on the CRF data. CRFs and correction documentation will be indexed and imaged. System backups for data stored at Quintiles and records retention for the study data will be consistent with Quintiles's standard procedures. Laboratory data will be sent directly to Quintiles, using Quintiles's standard procedures to handle and process the electronic transfer of these data.

Genentech will perform oversight of the data management of this trial, including approval of Quintiles's Data Management and Data Quality Plans. Data will be periodically transferred electronically from Quintiles to Genentech, and Genentech's standard procedures will be used to handle and process the electronic transfer of this data.

Assessment of Safety

Safety assessments will consist of monitoring and recording adverse events (AEs) and serious adverse events (SAEs), including targeted AEs.

Adverse Events

An AE is any unfavorable and unintended sign, symptom, or disease temporally associated with the use of an investigational (medicinal) product or other protocol-imposed intervention, regardless of attribution. This includes the following:

AEs not previously observed in the subject that emerge during the protocol-specified AE reporting period Complications that occur as a result of protocol-mandated interventions (e.g., invasive procedures such as biopsies)

Preexisting medical conditions (other than the condition being studied) judged by the investigator to have worsened in severity or frequency or changed in character during the protocol-specified AE reporting period Serious Adverse Events An AE should be classified as an SAE if it meets the following criteria:

It results in death (i.e., the AE actually causes or leads to death).

It is life threatening (i.e., the AE, in the view of the investigator, places the subject at immediate risk of death. It does not include an AE that, had it occurred in a more severe form, might have caused death.).

It requires or prolongs inpatient hospitalization.

It results in persistent or significant disability/incapacity (i.e., the AE results in substantial disruption of the subject's ability to conduct normal life functions).

It results in a congenital anomaly/birth defect in a neonate/infant born to a mother exposed to the study drug.

It is considered a significant medical event by the investigator based on medical judgment (e.g., may jeopardize the subject or may require medical/surgical intervention to prevent one of the outcomes listed above).

All AEs that do not meet any of the criteria for serious should be regarded as non-serious AEs.

The terms "severe" and "serious" are not synonymous. Severity (or intensity) refers to the grade of a specific AE, e.g., mild (Grade 1), moderate (Grade 2), or severe (Grade 3) myocardial infarction. "Serious" is a regulatory definition (see previous definition) and is based on subject or event outcome or action criteria usually associated with events that pose a threat to a subject's life or functioning. Seriousness (not severity) serves as the guide for defining regulatory reporting obligations from the Sponsor to applicable regulatory authorities.

Severity and seriousness should be independently assessed when recording AEs and SAEs on the CRF.

Targeted Adverse Events

Events of particular interest (targeted AEs) will be specifically elicited and include the following:
  ICH documented by computed tomography or magnetic resonance imaging
  Major bleeding, defined as severe blood loss (>5 mL/kg), blood loss requiring transfusion, or blood loss causing hypotension
  Embolism, defined as any "serious" embolic event, including pulmonary events, arterial events (e.g., stroke, peripheral embolism, or major organ embolism), or cholesterol plaque
  Thrombosis, including catheter-related venous thrombosis, defined as thrombus identified by radiological imaging (e.g., ultrasound, angiogram, or magnetic resonance) in the upper or lower extremity arteries or veins that leads to pain, swelling, and/or ischemia of the limb
  CRBSI, further classified as follows:
    Definite: the same organism from a semiquantitative culture of the catheter tip (>15 colony-forming units per catheter segment) and from a peripheral or catheter blood sample in a symptomatic subject with no other apparent source of infection
    Probable: defervescence of symptoms after antibiotic treatment, with or without removal of catheter, in the setting in which blood cultures confirm infection but catheter tip does not (or catheter tip does, but blood cultures do not) in a symptomatic subject with no other apparent source of infection
    Possible: defervescence of symptoms after antibiotic treatment or after removal of catheter in the absence of laboratory confirmation of bloodstream infection in a symptomatic subject with no other apparent source of infection
  Catheter-related complication, defined as rupture of the catheter during the flushing or instillation of drug, perforation of the indwelling vein, or bleeding at the catheter insertion site that would require surgical intervention (e.g., sutures or packing with gauze).

A targeted AE should be classified as an SAE if it meets the criteria outlined in Section 5.1.2, and should be reported as described in Section 5.4.

Methods and Timing for Assessing and Recording Safety Variables

The investigator is responsible for ensuring that all AEs and SAEs that are observed or reported during the study.

Adverse Event Reporting Period

The study period during which all AEs and SAEs must be recorded begins at initiation of study treatment and ends upon completion of the second visit following the last administration of study treatment or at subject discontinuation from the study, whichever is earlier.

Assessment of Adverse Events

The occurrence of AEs and SAEs will be assessed by the investigator at each subject evaluation timepoint during the study except at the follow-up visit at 30 days. All AEs and SAEs, whether volunteered by the subject, discovered by study personnel during questioning, or detected through physical examination, laboratory test, or other means, will be recorded in the subject's medical record and on the appropriate AE or SAE CRF page.

Each recorded AE or SAE will be described by its duration (i.e., start and end dates), severity (see Table 1), regulatory seriousness criteria if applicable, suspected relationship to study drug (see following guidance), and actions taken.

TABLE 1

Adverse Event Grading (Severity) Scale

| Severity | Description |
| --- | --- |
| Mild | Transient or mild discomfort (<48 hours); no interference with the subject's daily activities; no medical intervention/therapy required |
| Moderate | Mild to moderate interference with the subject's daily activities; no or minimal medical intervention/therapy required |
| Severe | Considerable interference with the subject's daily activities; medical intervention/therapy required; hospitalization possible |

Note:
Regardless of severity, some events may also meet regulatory seriousness criteria. Refer to definitions of an SAE (see Section 5.1.2).

To ensure consistency of AE and SAE causality assessments, investigators should apply the following general guideline:

Yes
  There is a plausible temporal relationship between the onset of the AE and administration of the study drug, and the AE cannot be readily explained by the subject's clinical state, intercurrent illness, or concomitant therapies; and/or the AE follows a known pattern of response to the study drug; and/or the AE abates or resolves upon discontinuation of the study drug or dose reduction and, if applicable, reappears upon rechallenge.

No
  Evidence exists that the AE has an etiology other than the study drug (e.g., preexisting medical condition, underlying disease, intercurrent illness, or concomitant medication); and/or the AE has no plausible temporal relationship to administration of the study drug (e.g., cancer diagnosed 2 days after first dose of study drug).

Note: The investigator's assessment of causality for individual AE reports is part of the study documentation process. Regardless of the "Yes" or "No" causality assessment for individual AE reports, the Sponsor will promptly evaluate all reported SAEs against cumulative product experience to identify and expeditiously communicate possible new safety findings to investigators and applicable regulatory authorities.

Eliciting Adverse Events

A consistent methodology of non-directive questioning for eliciting AEs at all subject evaluation timepoints should be adopted. Examples of non-directive questions include the following:

"How have you felt since your last clinical visit?"
"Have you had any new or changed health problems since you were last here?"

Specific Instructions for Recording Adverse Events on the CRF

Investigators should use correct medical terminology/concepts when recording AEs or SAEs on the CRF. Avoid colloquialisms and abbreviations.

All AEs should be recorded on an AE CRF page. There is designated space on this page to indicate if the event is serious (Y/N). For SAEs, an SAE CRF page must also be completed.

Only one medical concept should be recorded in the event field on the AE and SAE CRF pages.

a. Diagnosis versus Signs and Symptoms

If known at the time of reporting, a diagnosis should be recorded on the CRF rather than individual signs and symptoms (e.g., record only liver failure or hepatitis rather than jaundice, asterixis, and elevated transaminases). However, if a constellation of signs and/or symptoms cannot be medically characterized as a single diagnosis or syndrome at the time of reporting, each individual event should be recorded as an AE CRF page. If a diagnosis is subsequently established, it should be reported as follow-up information.

b. Adverse Events Occurring Secondary to Other Events

In general, AEs occurring secondary to other events (e.g., cascade events or clinical sequelae) should be identified by their primary cause. For example, if severe diarrhea is known to have resulted in dehydration, it is sufficient to record only diarrhea as an AE CRF page. However, if a medically significant secondary AE is separated in time from the initiating event, both should be recorded as independent events. For example, if a severe gastrointestinal hemorrhage leads to renal failure, both events should be recorded separate AE CRF pages.

c. Persistent or Recurrent Adverse Events

A persistent AE is one that extends continuously, without resolution, between subject evaluation timepoints. Such events should only be recorded once in the CRF unless their severity increases. If a persistent AE becomes more severe, it should be recorded again on an AE CRF page.

A recurrent AE is one that occurs, resolves, and subsequently recurs. All recurrent AEs should be recorded on an AE CRF page.

d. Clinical Laboratory Abnormalities

Individual laboratory abnormalities will generally not be recorded as AEs on the CRF. Only clinically significant laboratory abnormalities that result in study withdrawal, meet seriousness criteria, are themselves associated with clinical signs or symptoms, or require medical intervention (e.g., low hemoglobin requiring transfusion) will be recorded on an AE CRF page.

If the clinically significant laboratory abnormality is a sign of a disease or syndrome (e.g., alkaline phosphatase and bilirubin 5×the upper limit of normal associated with cholecystitis), only the diagnosis (e.g., cholecystitis) needs to be recorded on an AE CRF page.

If the clinically significant laboratory abnormality is not a sign of a disease or syndrome, the abnormality itself should be recorded on an AE CRF page. If the laboratory abnormality can be conveyed as a clinical diagnosis, the diagnosis should be recorded as the AE or SAE. For example, an elevated serum potassium level of 7.0 mEq/L should be recorded as "hyperkalemia."

Observations of the same clinically significant laboratory abnormality from visit to visit should not be repeatedly recorded on an AE CRF page, unless their severity, seriousness, or etiology changes.

e. Preexisting Medical Conditions

A preexisting medical condition is one that is present at the start of the study. Such conditions should be recorded on the Medical and Surgical History CRF page.

A preexisting medical condition should be re-assessed throughout the trial and recorded as an AE or SAE only if the frequency, severity, or character of the condition worsens during the study. When recording such events on an AE CRF page, it is important to convey the concept that the preexisting condition has changed by including applicable descriptors (e.g., "more frequent headaches").

f. Deaths

All deaths that occur during the protocol-specified AE reporting period, regardless of attribution, will be recorded on an AE CRF page and expeditiously reported to the Sponsor.

When recording a death, the event or condition that caused or contributed to the fatal outcome should be recorded as the single medical concept on an AE CRF page. If the cause of death is unknown and cannot be ascertained at the time of reporting, record "Unexplained Death" on an AE CRF page. This site should then make every attempt to urgently identify the cause of death (e.g., via primary care physician, autopsy report, hospital record) and expeditiously report the cause of death to Sponsor.

g. Hospitalizations for Medical or Surgical Procedures

Any AE that results in hospitalization or prolonged hospitalization should be documented and reported as an SAE.

If a subject is hospitalized to undergo a medical or surgical procedure as a result of an AE, the event responsible for the procedure, not the procedure itself, should be recorded as the SAE. For example, if a subject is hospitalized to undergo coronary bypass surgery, record the heart condition that necessitated the bypass as the SAE.

Hospitalizations for the following reasons will not be recorded as SAEs on the CRF:

Hospitalization or prolonged hospitalization for diagnostic or elective surgical procedures for preexisting conditions recorded on the Medical and Surgical History CRF Hospitalization or prolonged hospitalization required to allow efficacy measurement for the study Hospitalization or prolonged hospitalization for scheduled therapy of the target disease of the study.

h. Pregnancy

If a female subject becomes pregnant while receiving study drug or within 90 days after the last dose of study drug, a Pregnancy Report CRF should be completed and expeditiously submitted to the Sponsor to facilitate outcome follow-up.

Abortion, whether accidental, therapeutic, or spontaneous, should always be classified as serious, recorded as an SAE, and expeditiously reported to the Sponsor. Similarly, any congenital anomaly/birth defect in a child born to a female subject exposed to the study drug should be recorded and reported as an SAE.

i. Poststudy Adverse Events

The investigator should expeditiously notify the Medical Monitor by telephone of any SAE that occurs after a subject has completed or discontinued from study participation if attributed to prior study drug exposure.

The Medical Monitor should also be notified if the investigator becomes aware of the development of cancer or a congenital anomaly in a subsequently conceived offspring of a female subject who participated in the study.

What is claimed is:

1. A method for restoring function in a dysfunctional hemodialysis catheter indwelling in a mammal, which catheter has a blood flow rate (BFR) of less than 300 mL/minute, which method comprises administering tenecteplase in a total dose of about 2 to 4 mg locally into all catheter lumens and allowing the tenecteplase to dwell in the catheter for from about one hour to about 72 hours, such that the BFR of the catheter is equal to or greater than 300 mL/minute, wherein the catheter is not an implantable port.

2. The method of claim 1 wherein the dysfunctional hemodialysis catheter additionally has a BFR at least 25 mL/minute below the prescribed BFR at an arterial pressure of −250 mmHg during the first 30 minutes of the hemodialysis.

3. The method of claim 1 wherein the tenecteplase is in a solution of sterile water for injection or bacteriostatic water for injection.

4. The method of claim 1 wherein the tenecteplase dwells in the catheter until the BFR of the catheter is improved over the BFR before administration of tenecteplase and the improvement maintained for at least 48 hours.

5. The method of claim 1 wherein the tenecteplase is in sterile water for injection.

6. The method of claim 1 wherein the total dose of tenecteplase is about 4 mg.

7. The method of claim 1 wherein the tenecteplase is instilled into the catheter for about one hour.

8. The method of claim 1 wherein the tenecteplase is instilled into the catheter and allowed to dwell for a period of from over about one hour to about 72 hours.

9. The method of claim 8 wherein the period the tenecteplase is allowed to dwell is from about 2 to about 48 hours.

10. The method of claim 1 wherein the tenecteplase is administered more than once.

11. The method of claim 10 wherein the tenecteplase is administered at each hemodialysis session that the mammal undergoes.

12. The method of claim 1 wherein the tenecteplase is administered once or twice.

13. The method of claim 12 wherein the tenecteplase is administered once.

14. The method of claim 1 wherein the mammal undergoes hemodialysis after administration of the tenecteplase.

15. The method of any one of claims 1-6 and 14 wherein the mammal is a human.

* * * * *